(12) United States Patent
Lowenthal et al.

(10) Patent No.: US 6,642,032 B2
(45) Date of Patent: Nov. 4, 2003

(54) USES OF AVIAN INTERFERON GAMMA (IFN-γ)

(75) Inventors: John W. Lowenthal, Belmont (AU); Michael A. Johnson, Thornbury (AU); Terri E. O'Neil, Highton (AU); Jennifer J. York, Clifton Hill (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 0 days.

(21) Appl. No.: 09/443,218

(22) Filed: Nov. 19, 1999

(65) Prior Publication Data

US 2003/0099610 A1 May 29, 2003

Related U.S. Application Data

(63) Continuation-in-part of application No. 08/765,381, filed as application No. PCT/AU96/00114 on Mar. 5, 1996, now Pat. No. 6,083,724, application No. 09/443,218, which is a continuation-in-part of application No. 09/272,032, filed on Mar. 18, 1999, now Pat. No. 6,296,852, which is a continuation-in-part of application No. 08/448,617, filed as application No. PCT/AU94/00189 on Apr. 14, 1994, now abandoned.

(30) Foreign Application Priority Data

Apr. 14, 1993 (AU) ............................................. PL 8297
Mar. 6, 1995 (AU) ......................................... PN 1542/95

(51) Int. Cl.[7] ........................ C12P 19/34; C12N 15/00
(52) U.S. Cl. ................ 435/91.1; 435/91.33; 435/320.1; 536/23.72
(58) Field of Search ......................... 435/320.1, 235.1, 435/91.1, 91.33, 5; 536/23.72

(56) References Cited

U.S. PATENT DOCUMENTS

| 4,456,748 A | 6/1984 | Goeddel |
| 4,935,233 A | 6/1990 | Bell et al. |
| 5,641,656 A | 6/1997 | Sekellick et al. |

FOREIGN PATENT DOCUMENTS

| DE | 4036855 | 5/1992 |
| EP | 0 088 540 A | 9/1983 |
| EP | 0492179 A2 * | 11/1991 |

OTHER PUBLICATIONS

Digby, et al., (1995) "Cloning and Expression of the chicken Interferon–gamma gene," *Journal of Interferon and Cytokine Research*, 15:939–945.

Fredericksen, et al. (1987) "Purification of Avian T Cell Growth Factor and Immune Interferon Using Gel Filtration High Resolution Chromatography," *UCLA Symposia on Molecular and Cellular Biology*: 1:145–156.

Gray, et al., (1982) "Expression of human immune interferon cDNA in *E. coli* and monkey cells," *Nature*, 295:503–508.

Lillehoj, et al., (1993) "Avian Interleukin–2 and Interferon," *Colloques De L'Inra* (*Avian Immunology In* Progress), 62:105–111.

Lillehoj, et al., (1993) "Biochemical and functional characterizations of avian gamma–Interferon and Interleukin–2," *Colloques De L'Inra* (*Avian Immunology In Progess*), 62:131–136.

Lowenthal, et al., (1995) "Production of Interferon–gamma by chicken T cells," *Journal of Interferon and Cytokine Research*, 15:933–938.

Schultz, et al. (1995) "Recombinant Chicken Interferon: A Potent Antiviral Agent that Lacks Intrinsic Macrophage Activating Factor Activity", *Eur. J. Immunol.*, 25:847–851.

Schultz, et al. (1995) "Recombinant Chicken Interferon from *Escherichia coli* and Transfected COS Cells is Biologically Active", *Eur. J. Immunol.*, 229:73–76.

Sekkellick, et al., (1994) "Chicken Interferon gene: Cloning, expression and analysis," *Journal of Interferon Research*, 14:71–79.

Weinig, et al, (1996) "Biological properties of recombinant chicken Interferon–gamma," *European Journal of Immunology*, 26:2440–2447.

Weiler, H., et al. (1987) *Avian Pathol* 16:439–452.

* cited by examiner

*Primary Examiner*—Ali R. Salimi
(74) *Attorney, Agent, or Firm*—Greenlee, Winner and Sullivan, P.C.

(57) ABSTRACT

The present invention provides compositions comprising recombinant avian IFN-γ polypeptides and methods using said recombinant avian IFN-γ polypeptides and compositions to enhance the immune responses of birds, and to enhance growth and/or prevent weight loss in birds. The present invention is particularly useful in the prophylactic and therapeutic treatment of birds against coccidiosis and the causative agent thereof.

6 Claims, 38 Drawing Sheets

USES OF AVIAN INTERFERON GAMMA (IFN-γ)

CROSS REFERENCE TO RELATED APPLICATIONS

The present application is a continuation-in-part of U.S. Ser. No. 08/765,381, filed Apr. 25, 1997, now U.S. Pat. No. 6,083,724, issued Jul. 4, 2000, and U.S. Ser. No. 09/272,032 filed Mar. 18, 1999, now U.S. Pat. No. 6,296,852B1, issued Oct. 2, 2001. U.S. Ser. No. 08/765,381 is the United States national phase application of International application No. PCT/AU96/00114 filed on Mar. 5, 1996, which claims priority from Australian Patent Application No. PN 154295, filed Mar. 6, 1995. U.S. Ser. No. 09/272,032 is a continuation-in-part application of U.S. Ser. No. 08/448,617, filed Sep. 8, 1995, now abandoned, which is the United States national phase application of International application No. PCT AU94/00189 filed Apr. 14, 1994, which claims priority from Australian Patent Application No. PL 8297 filed Apr. 14, 1993.

STATEMENT REGARDING FEDERALLY SPONSORED RESEARCH OR DEVELOPMENT

Not Applicable

FIELD OF THE INVENTION

The present invention relates generally to recombinant avian interferon polypeptides and genetic sequences encoding same, and uses therefor. In particular, the present invention is directed to the use of recombinant avian IFN-γ polypeptides as an immune response modulator and as a growth enhancing agent in avian species. The present invention is particularly useful in the prophylactic and therapeutic treatment of birds against coccidiosis and the causative agent thereof.

BACKGROUND OF THE INVENTION

1. Field of the Invention

The rapidly increasing sophistication of recombinant DNA technology is greatly facilitating research into the medical and veterinary fields. Cytokine research is of particular importance, especially as these molecules regulate the proliferation, differentiation and function of a great variety of cells, such as cells involved in mediating an immune response. Administration of recombinant cytokines or regulating cytokine function and/or synthesis is becoming, increasingly, the focus of medical research into the treatment of a range of disease conditions in humans and animals. The present invention seeks to provide novel reagents and methods that employ recombinant cytokine polypeptides, for the treatment of disease conditions in birds.

2. Description of Related Art Including Information Disclosed Under 37 C.F.R. 1.97 and 1.98

In mammals, interferons (IFN) represent a family of cytokines that share the capacity to inhibit viral replication and to exert effects on immune function. There are two distinct types of IFN. Type I IFN is produced by a variety of cell types in response to viral infection and includes IFN-α and -β. Typically, IFN-α is produced by leukocytes such as monocytes and macrophages while fibroblasts and epithelial cells are the major source of IFN-β. Type I IFNs share a high degree of amino acid homology, bind to the same cell surface receptor and there biological functions are resistant to heat and low pH treatment. (Weissmann and Weber, 1986).

In contrast, the production of IFN-γ in mammals is restricted to activated T cells and NK cells and is encoded by a gene that is unrelated to those which express IFN-α or IFN-β. Features that distinguish IFN-γ from -α/β include their binding to different cell surface receptors and that the former is exquisitely sensitive to heat and low pH treatment (Weissmann and Weber, 1986). Another distinction is the ability of IFN-γ, but not IFN-α or IFN-β, to stimulate macrophages to produce reactive nitrogen intermediates such as nitric oxide, nitrate and nitrite (Fast et al, 1993; Huang et al, 1993).

Chicken T cells produce IFN following stimulation with antigen or mitogen (Prowse and Pallister, 1989; Lowenthal et al, 1993; Pusztai et al, 1986; Weiler and von Bulow, 1987; Dijkmans et al, 1990) as measured by the ability to protect chick embryonic fibroblasts (CEF) from virus-mediated lysis. There has been controversy as to whether this IFN activity is the Type I interferon, or alternatively, an avian equivalent of mammalian IFN-γ (Lillehoj et al, 1992).

The gene for chicken Type I IFN (ChIFN-α) has recently been cloned (Sekellick et al, 1994) and when the protein was compared to mammalian IFNs it was shown to have 20–24% amino acid sequence identity to Type I IFNs, whereas it was unrelated to known mammalian IFN-γ polypeptides. Furthermore, recombinant ChIFN-α was shown to have antiviral activity, but lacked macrophage activating function in that it was unable to induce nitrite secretion in monocytes (Schultz et al, 1995), consistent with the properties of mammalian Type I IFN.

U.S. Ser. No. 08/765,381, which is incorporated herein by way of reference, teaches genetic sequences encoding avian IFN-γ from chicken reticuloendotheliosis virus (REV)-transformed spleen cell cultures (Lowenthal et al, 1995 a, b). That specification further teaches the isolation of homologous IFN-γ-encoding genetic sequences from species other than chickens, gene constructs and viral vectors comprising said genetic sequences, methods for the production of recombinant avian IFN-γ using the said gene constructs and viral vectors, and methods of prophylaxis and treatment using the recombinant polypeptides. The avian and mammalian IFN-γ polypeptides are only 30% identical, as determined using the ClustalW programme and the algorithm of Thompson et al., 1994), or alternatively, 32% identical as determined using the ClustalV programme.

Birds suffer from a variety of diseases that represent a considerable cost to the poultry industry, including diseases that are produced by bacteria and viruses, such as, for example, infectious bronchitis virus, avian infectious laryngeotracheitis virus, infectious bronchitis virus, Newcastle disease virus, Marek's Disease virus, chicken anemia virus, avian influenza virus, E. coli, Salmonella ssp., Eimeria ssp. and Mycoplasma ssp., amongst others.

For example, the causative agent of coccidiosis in birds, Eimeria ssp., in particular E. acervulina, is capable of infecting birds at any period in their life cycle. Coccidiosis represents a considerable cost in terms of reduced productivity, because the disease in birds prevents digestion for about 4–5 days, thereby leading to a considerable weight loss, costing the industry approximately $700 million per annum. Current treatments for coccidiosis include the use of chemicals in feed stocks.

SUMMARY OF THE INVENTION

This application is a continuation-in-part application of U.S. Ser. No. 08/765,381, the entire contents of which are incorporated herein by way of reference.

Bibliographic details of the publications referred to in this specification by author are collected at the end of the description.

Sequence Identity Numbers (SEQ ID NOs.) for the nucleotide and amino acid sequences referred to in the specification appear after the claims.

Throughout this specification and the claims that follow, unless the context requires otherwise, the word "comprise", or variations such as "comprises" or "comprising" will be understood to imply the inclusion of a stated element or integer or group of elements or integers, but not the exclusion of any other element or integer or group of elements or integers.

Those skilled in the art will appreciate that the invention described herein is susceptible to variations and modifications other than those specifically described. It is to be understood that the invention includes all such variations and modifications. the invention also includes all of the steps, features, compositions and compounds referred to or indicated in this specification, individually or collectively, and any and all combinations or any two or more of said steps or features.

In work leading up to the present invention, the inventors sought to produce improved methods for the prophylactic and therapeutic treatment of a wide range of diseases in birds, and, in particular, the prophylactic and therapeutic treatment of coccidiosis.

The inventors cloned avian IFN-γ cDNAs and genes and produced recombinant gene constructs comprising same for the expression of recombinant IFN-γ polypeptides therefrom, as described in U.S. Ser. No. 08/765,381 which is incorporated herein by way of reference.

Immunoreactive molecules, in particular polyclonal and monoclonal antibodies have been produced to the recombinant avian IFN-γ polypeptide of the invention.

Additionally, the inventors have discovered that avian IFN-γ administered to birds is capable of promoting the growth of birds, as well as preventing weight loss associated with pathogenic infections when administered thereto as a prophylactic or therapeutic reagent by any means. The present invention clearly encompasses the use of avian IFN-γ as an immunomodulatory molecule both in homologous species and across species boundaries.

Accordingly, one aspect of the present invention provides a method of treatment or prophylaxis of birds exposed to or infected with a pathogenic organism, said method comprising administering thereto an immunoresponsive effective amount of an avian IFN-γ cytokine polypeptide for a time and under conditions sufficient to maintain, stimulate or enhance the immmunoresponsiveness of said bird, wherein said avian IFN-γ cytokine polypeptide is selected from the group consisting of:
  (a) a polypeptide having the amino acid sequence set forth in any one of SEQ ID NOs: 2–7;
  (b) a polypeptide having the amino acid sequence set forth as the mature protein region of any one of SEQ ID NOs: 2–7;
  (c) a polypeptide encoded by DNA present in an avian DNA library, wherein said DNA hybridizes under conditions of at least moderate stringency with a probe having a sequence complementary to at least 50 contiguous nucleotides of SEQ ID NO: 1;
  (d) a polypeptide encoded by a nucleotide sequence that is degenerate with a DNA molecule according to (c); and
  (e) a polypeptide comprising at least 10 contiguous amino acids of any one of SEQ ID NOs: 2–7, wherein said polypeptide has immunomodulatory activity.

Because of the maintenance, stimulation or enhancement of the immmunoresponsiveness of birds administered with the subject cytokine polypeptide, this aspect of the invention relates further to the enhancement and/or stimulation of an immune response to one or more antigens in a bird, wherein an immunomodulatingly effective amount of an avian IFN-γ cytokine polypeptide is optionally administered with an antigen or pathogenic agent against which an immune response is desired. In such an embodiment of the invention, the administered avian IFN-γ cytokine polypeptide acts essentially as an adjuvant, such as, for example, may be used in a vaccine composition.

A second aspect of the invention provides a method of enhancing the growth performance of a healthy or diseased bird, said method comprising administering to said bird an avian IFN-γ cytokine polypeptide for a time and under conditions sufficient to induce weight gain in said healthy or diseased bird or to prevent weight loss in said diseased bird, wherein said avian IFN-γ cytokine polypeptide is selected from the group consisting of:
  (a) a polypeptide having the amino acid sequence set forth in any one of SEQ ID NOs: 2–7;
  (b) a polypeptide having the amino acid sequence set forth as the mature protein region of any one of SEQ ID NOs: 2–7;
  (c) a polypeptide encoded by DNA present in an avian DNA library, wherein said DNA hybridizes under conditions of at least moderate stringency with a probe having a sequence complementary to at least 50 contiguous nucleotides of SEQ ID NO: 1;
  (d) a polypeptide encoded by a nucleotide sequence that is degenerate with a DNA molecule according to (c); and
  (e) a polypeptide comprising at least 10 contiguous amino acids of any one of SEQ ID NOs: 2–7, wherein said polypeptide has immunomodulatory activity.

This aspect of the invention particularly relates to the prevention of weight loss associated with coccidiosis of birds, wherein said avian IFN-γ cytokine polypeptide is administered to a bird selected from the group consisting of:
  (i) healthy birds that are susceptible to infection by Eimeria spp.;
  (ii) asymptomatic birds infected with Eimeria spp.; and
  (iii) birds suffering from coccidiosis.

According to this embodiment, it is preferred to administer a composition comprising the avian IFN-γ cytokine polypeptide for a time and under conditions sufficient to induce weight gain in said healthy or infected bird or to prevent weight loss in said infected bird.

The present invention clearly extends to compositions for use in performing the inventive methods supra, such as, for example, those compositions of matter comprising avian IFN-γ cytokine polypeptides and antibodies capable of binding thereto in combination with one or more suitable carriers and/or excipients and/or diluents, in particular those carriers and/or excipients and/or diluents suitable for veterinary use.

Accordingly, a third aspect of the invention provides an antibody molecule that is capable of binding to an avian IFN-γ cytokine polypeptide as described supra, in particular antibodies that bind to chicken IFN-γ.

A fourth aspect of the invention provides a composition for enhancing the growth performance of a bird comprising a carrier, excipient or diluent in combination with an amount of a recombinant avian IFN-γ cytokine polypeptide selected from the group consisting of:

(a) a polypeptide having the amino acid sequence set forth in any one of SEQ ID NOs: 2–7;

(b) a polypeptide having the amino acid sequence set forth as the mature protein region of any one of SEQ ID NOs: 2–7;

(c) a polypeptide encoded by DNA present in an avian DNA library, wherein said DNA hybridizes under conditions of at least moderate stringency with a probe having a sequence complementary to at least 50 contiguous nucleotides of SEQ ID NO: 1;

(d) a polypeptide encoded by a nucleotide sequence that is degenerate with a DNA molecule according to (c); and (e) a polypeptide comprising at least 10 contiguous amino acids of any one of SEQ ID NOs: 2–7, wherein said polypeptide has immunomodulatory activity.

The invention also provides a vaccine composition for the prophylactic treatment of a bird against a pathogenic organism comprising an antigen in combination with an amount of a recombinant avian IFN-γ cytokine polypeptide selected from the group consisting of:

(a) a polypeptide having the amino acid sequence set forth in any one of SEQ ID NOs: 2–7;

(b) a polypeptide having the amino acid sequence set forth as the mature protein region of any one of SEQ ID NOs: 2–7;

(c) a polypeptide encoded by DNA present in an avian DNA library, wherein said DNA hybridizes under conditions of at least moderate stringency with a probe having a sequence complementary to at least 50 contiguous nucleotides of SEQ ID NO: 1;

(d) a polypeptide encoded by a nucleotide sequence that is degenerate with a DNA molecule according to (c); and (e) a polypeptide comprising at least 10 contiguous amino acids of any one of SEQ ID NOs: 2–7, wherein said polypeptide has immunomodulatory activity.

In particularly preferred embodiments of the present invention, the inventive compositions described herein utilize recombinant chicken IFN-γ, or cells infected with recombinant FAV expressing chicken IFN-γ, or alternatively, recombinant FAV expressing chicken IFN-γ, or nucleic acid encoding chicken IFN-γ.

BRIEF DESCRIPTION OF THE DRAWINGS

FIG. 1 shows graphical representations comparing the efficacies of the nitrite-release bioassay and ELISA using Mab 80.9 to measure recombinant avian IFN-γ produced in a variety of cell types. ChIFN-γ was produced in COS cells (o), Concanavalin A-activated chicken T cells (CS cells; ▲), E. coli (■), or CK cells infected with recombinant FAV expressing ChIFN-γ (X), and either used as an active non-denatured protein (unbroken lines), or alternatively, following heat-denaturation at 65° C. for 15 min in order to reduce the biological activity of ChIFN-γ (broken lines).

FIG. 4 provides diagrammatic representations of polyacrylamide gels showing expression of recombinant ChIFN-γ in E. coli and subsequent purification.

In FIG. 5A the capacity of purified recombinant ChIFN-γ (ED: dialyzed to remove imidazole; E: non-dialyzed), to induce nitrite secretion by HD11 chicken macrophages is shown. In FIG. 5B; the capacity of purified recombinant ChIFN-γ (ED: dialyzed; E: non-dialyzed) and chicken spleen cell conditioned media (CM) to protect CEFs from virus mediated lysis is shown. In FIG. 5C, the capacity of purified recombinant ChIFN-γ (ED: dialyzed; E: non-dialyzed) and recombinant ChIFN-α to protect TEFs from virus mediated lysis is shown.

FIG. 10 provides graphical representations showing the induction of MHC class II antigen Cla expression on HD11 cells by recombinant ChIFN-γ protein.

Figure 10A:
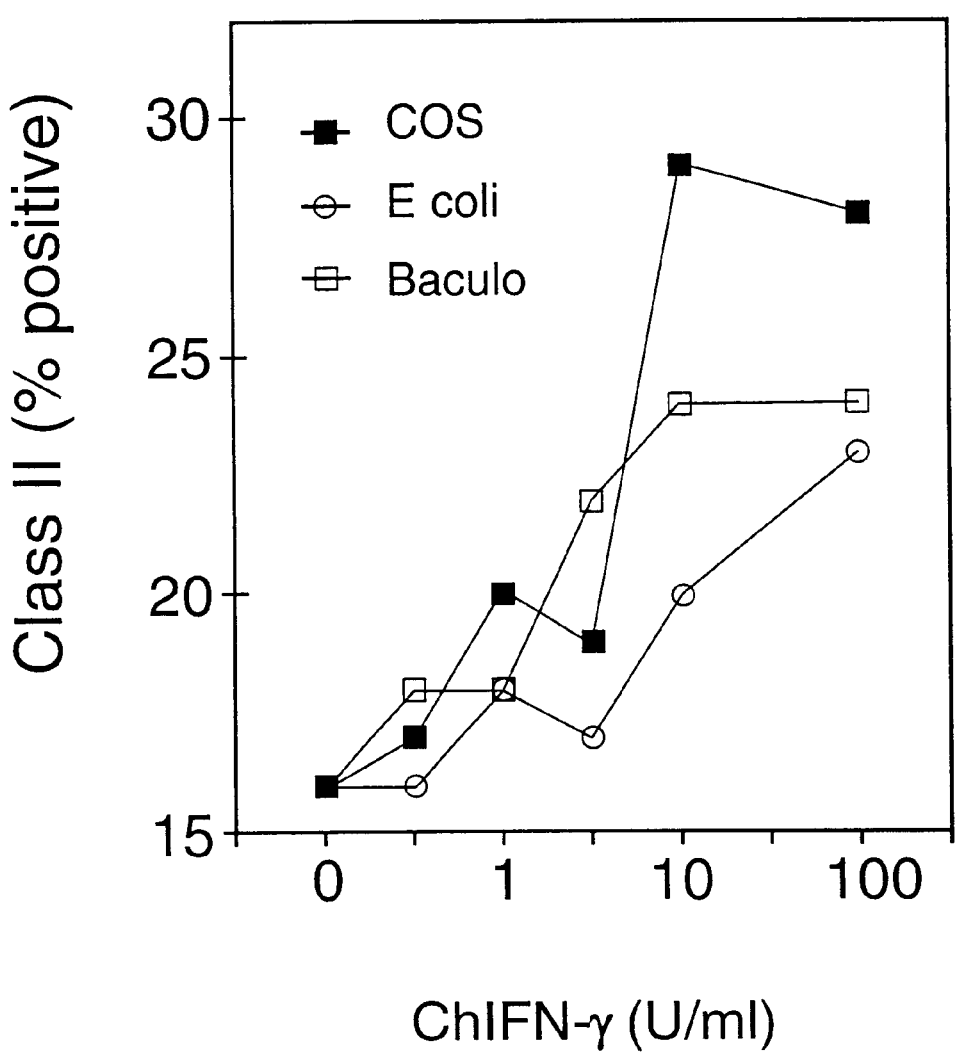

In FIG. 10A, there is provided a graphical representation showing the dosage-dependent increase in Cla on the surface of HD11 cells that were cultured for 24 h in the presence of rChIFN-γ produced by COS cells, *E. coli,* or in a baculovirus system.

Figure 10B:
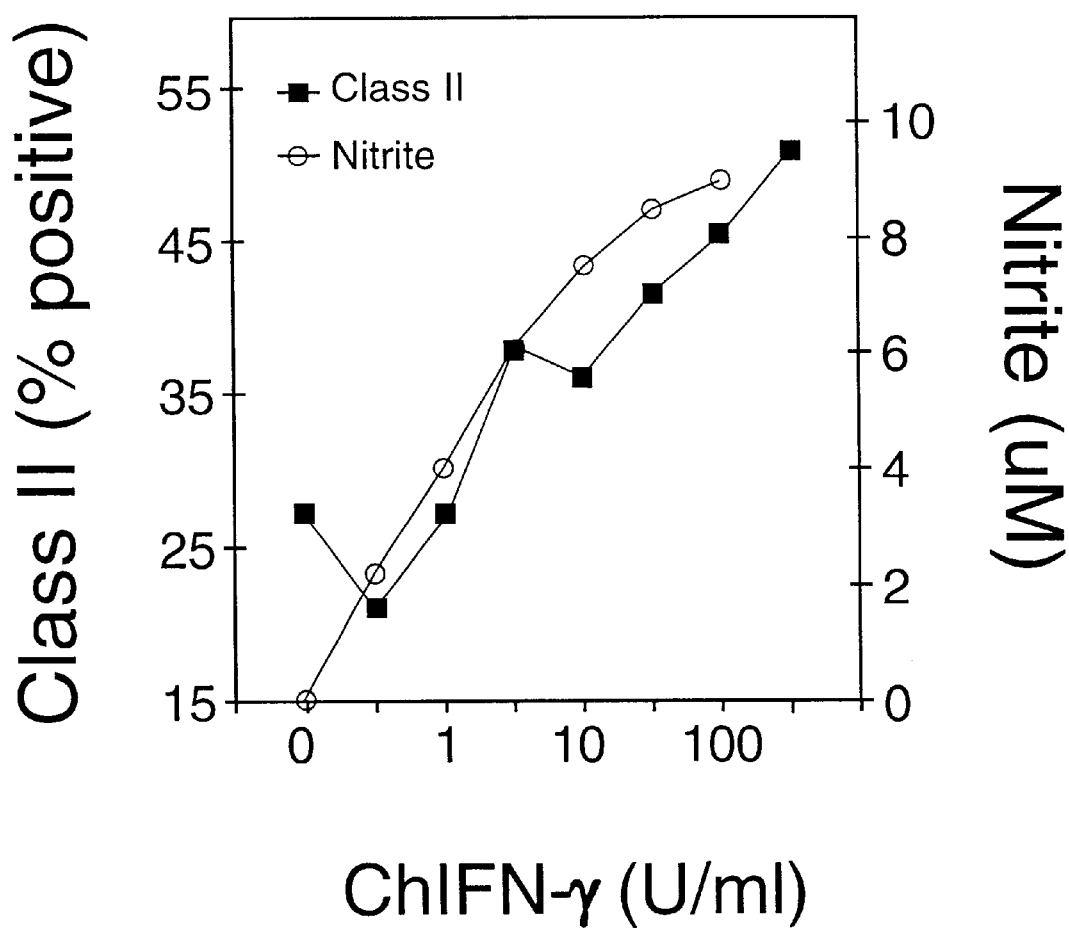

In FIG. 10B, there is provided a graphical representation showing the dosage-dependent increase in Cla on the surface of HD11 cells that were cultured for 24 h in the presence of rChIFN-γ produced by *E. coli.* The level of Cla expression and nitrite secretion was measured 24 hr after incubation with various concentrations of ChIFN-γ.

Figure 10C:
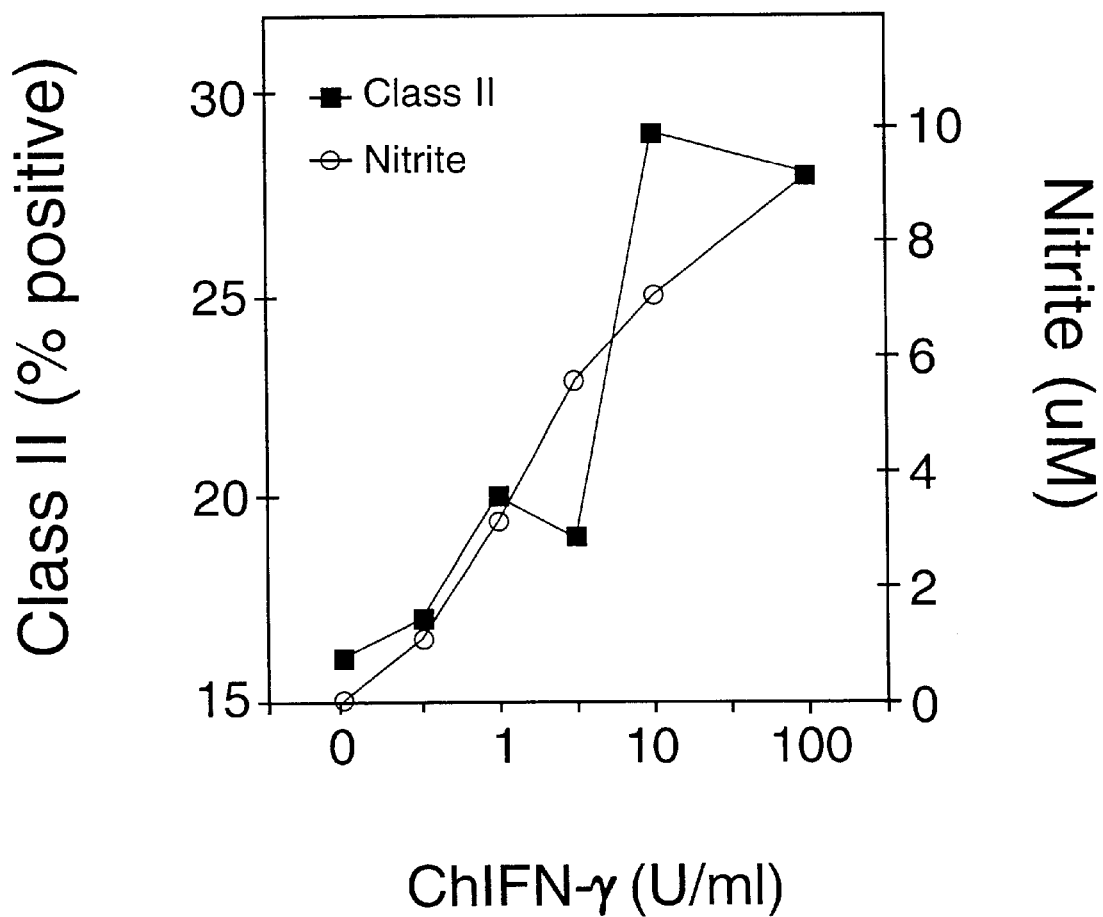

In FIG. 10C, there is provided a graphical representation showing the dosage-dependent increase in Cla on the surface of HD11 cells that were cultured for 24 h in the presence of rChIFN-γ produced by COS cells. The level of Cla expression and nitrite secretion was measured 24 hr after incubation with various concentrations of ChIFN-γ.

Figure 11:
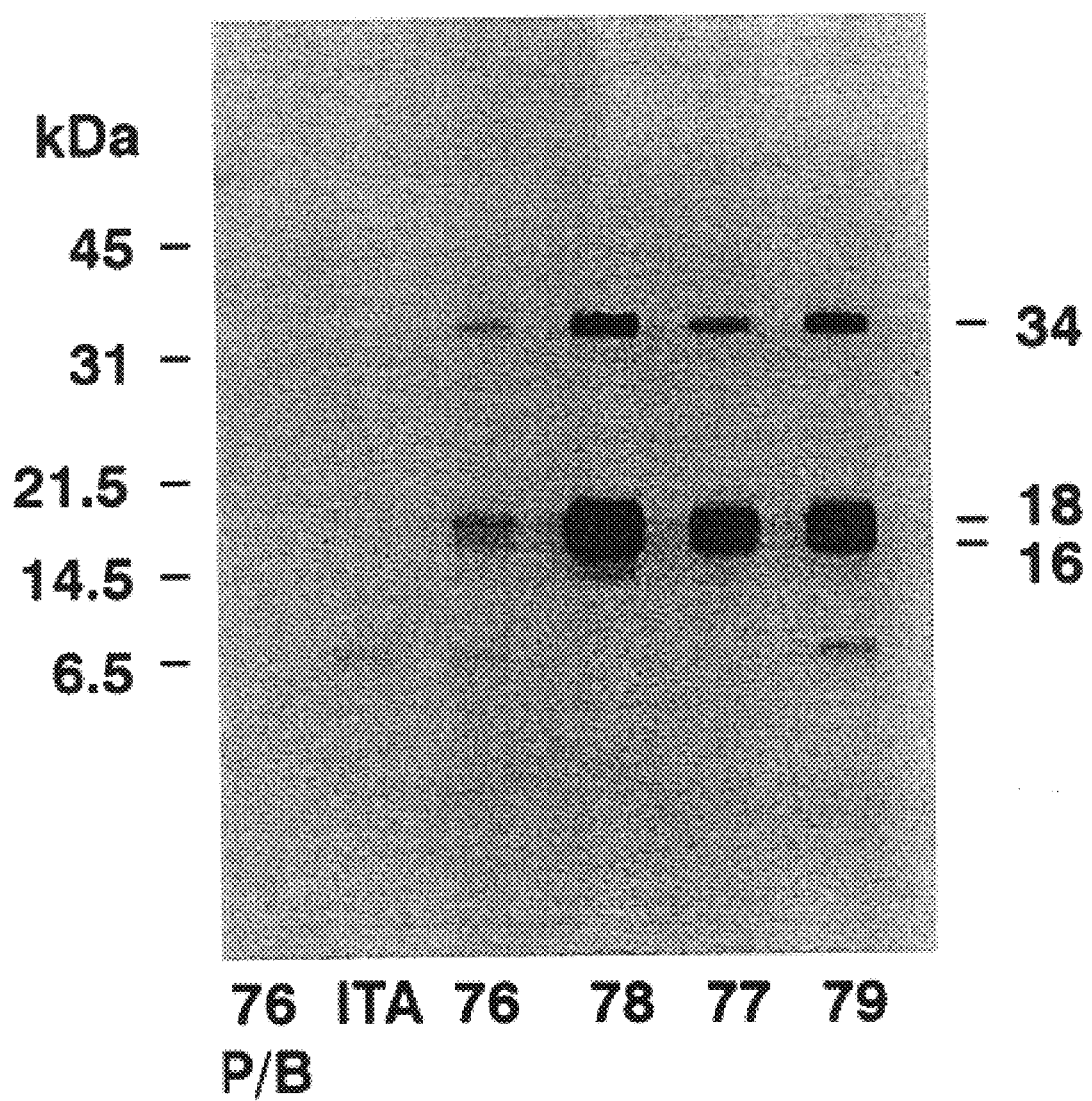

FIG. 11 is a diagrammatic representation of a Western Blot showing binding of rabbit anti-ChIFN-γ sera to recombinant ChIFN-γ. Recombinant ChIFN-γ was electrophoresed on an acrylamide gel, blotted onto nitrocellulose which was then cut into strips. Individual strips were incubated in sera; (76 P/B, normal rabbit serum; ITA, serum raised against an irrelevant antigen; sera 76, 77, 78, and 79 are sera from 4 rabbits immunized with recombinant ChIFN-γ).

Figure 12:
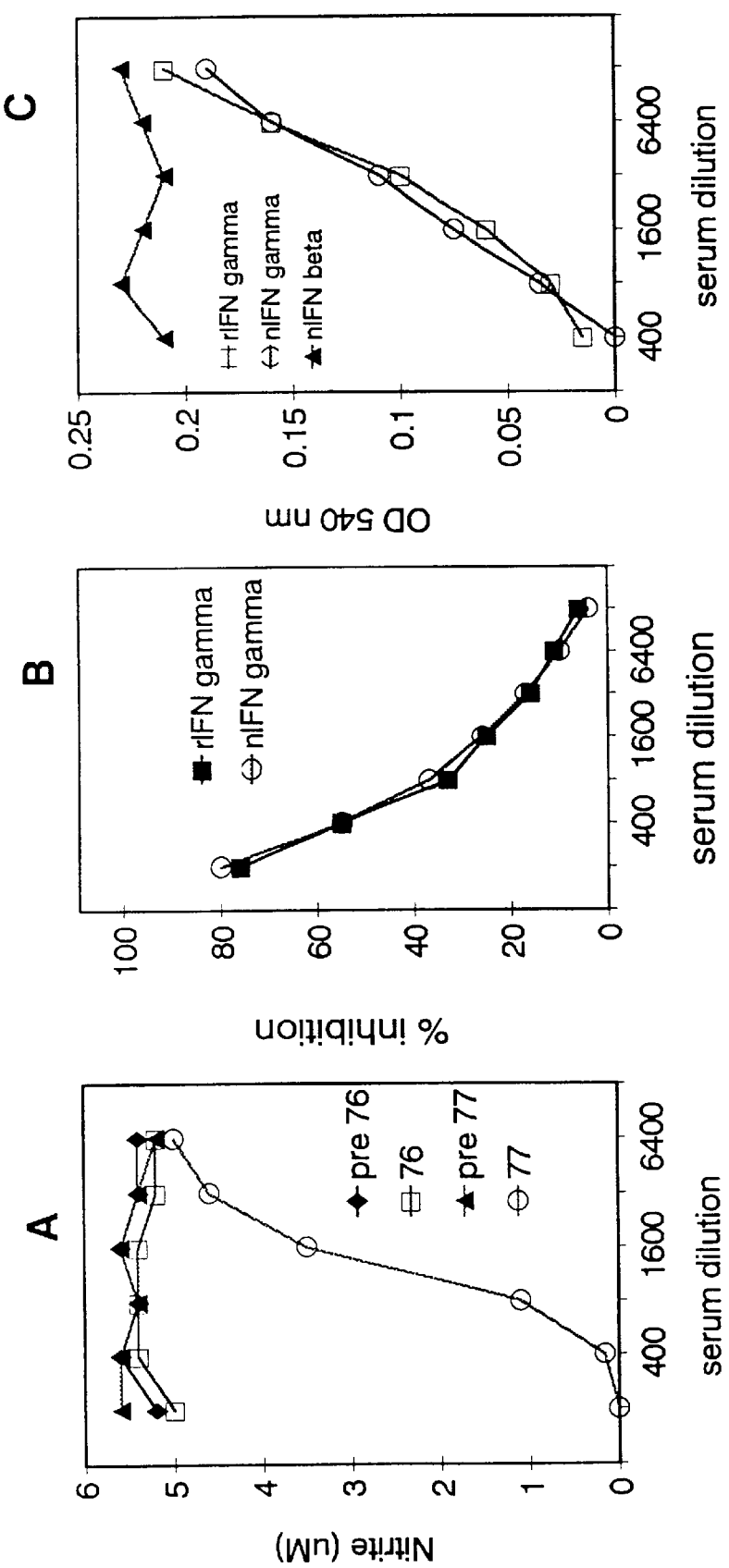

FIG. 12 provides graphical representations showing the ability of rabbit anti-recombinant ChIFN-γ antisera to block the function of both recombinant (r) and native (n) ChIFN-γ as measured using either the nitrite assay FIG. 12A; FIG. 12B) or using the CEF assay (FIG. 12C).

Figure 13:
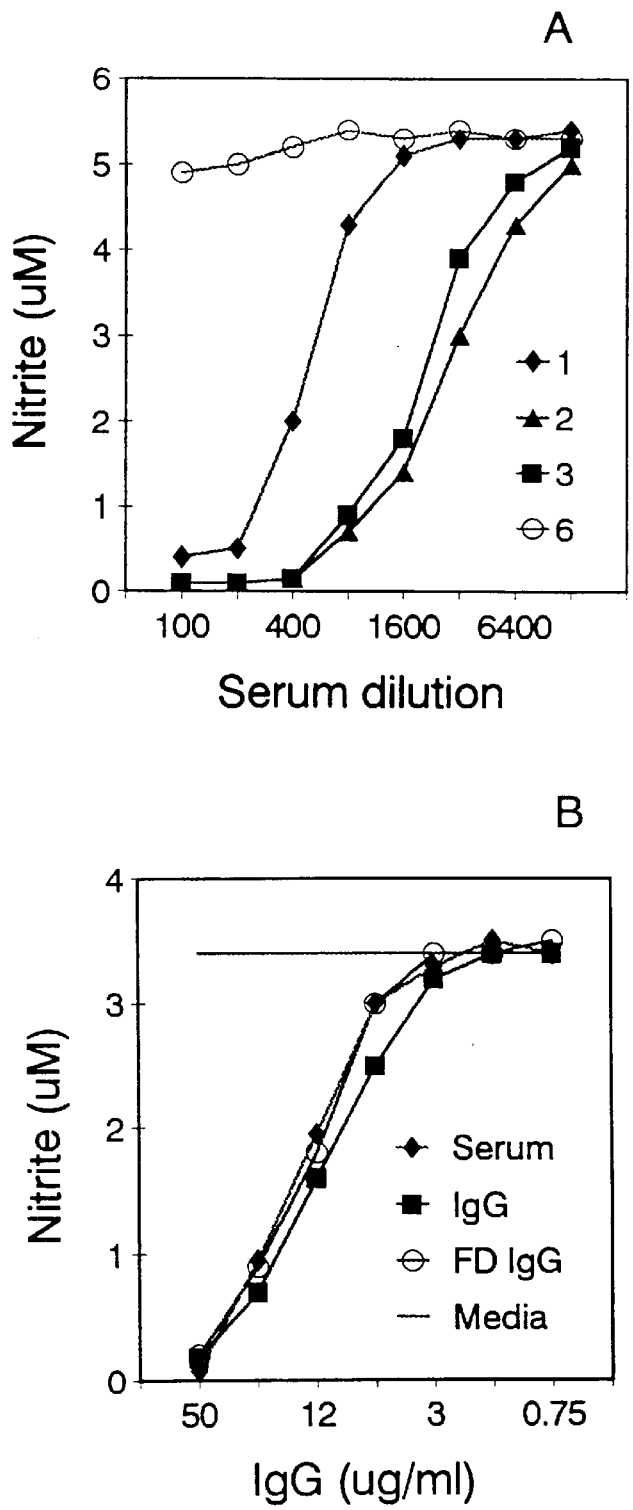

FIG. 13 provides graphical representations showing the ability of mouse anti-recombinant ChIFN-γ antisera (FIG. 13A) and purified rabbit anti-recombinant ChIFN-γ IgG (FIG. 13B) to block the function of native ChIFN-γ in the nitrite assay.

Figure 14A:
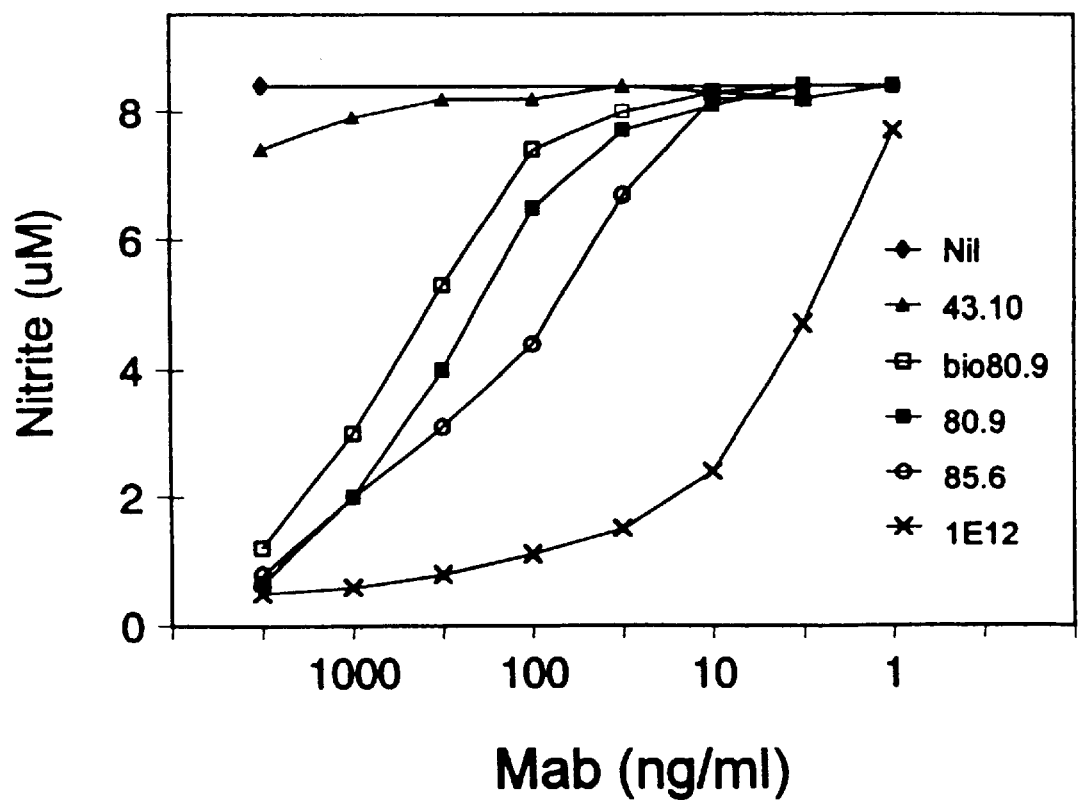

FIG. 14 provides graphical representations showing the inhibition of ChIFN-γ biological activity by monoclonal antibodies. In FIG. 14A, COS cell-derived rChIFN-γ (10 U/ml) was incubated for 1 hr in the presence of the various Mabs indicated in the Figure, followed by the addition of HD11 cells and the determination of nitrite release therefrom.

Figure 14B:
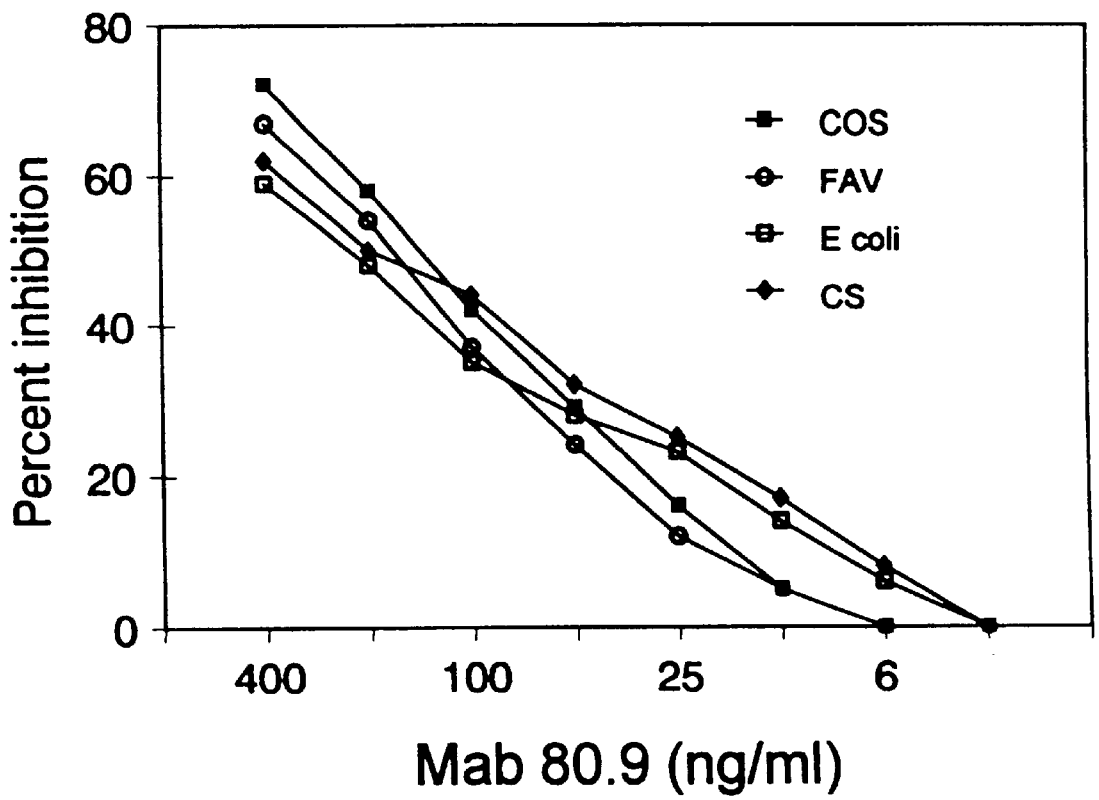
Figure 14C:
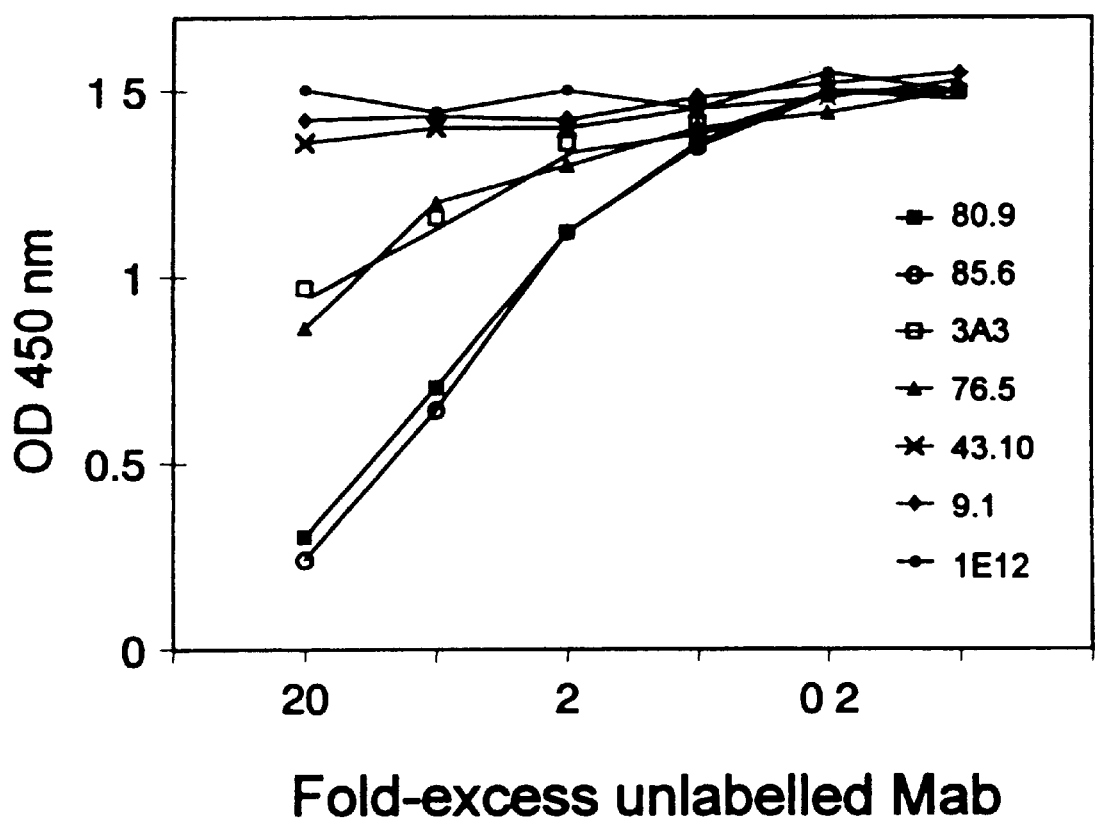
Figure 15A:
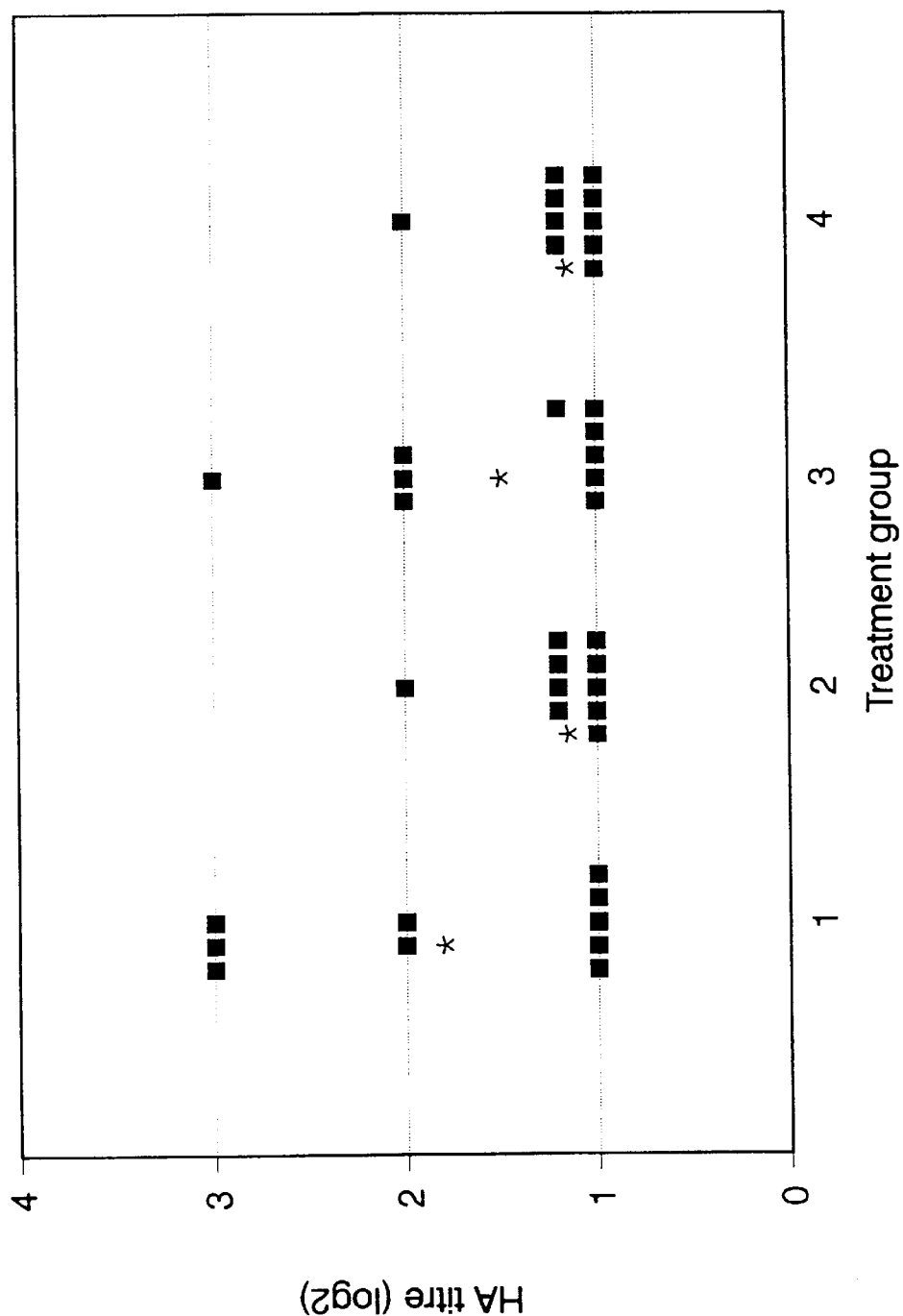
Figure 15B:
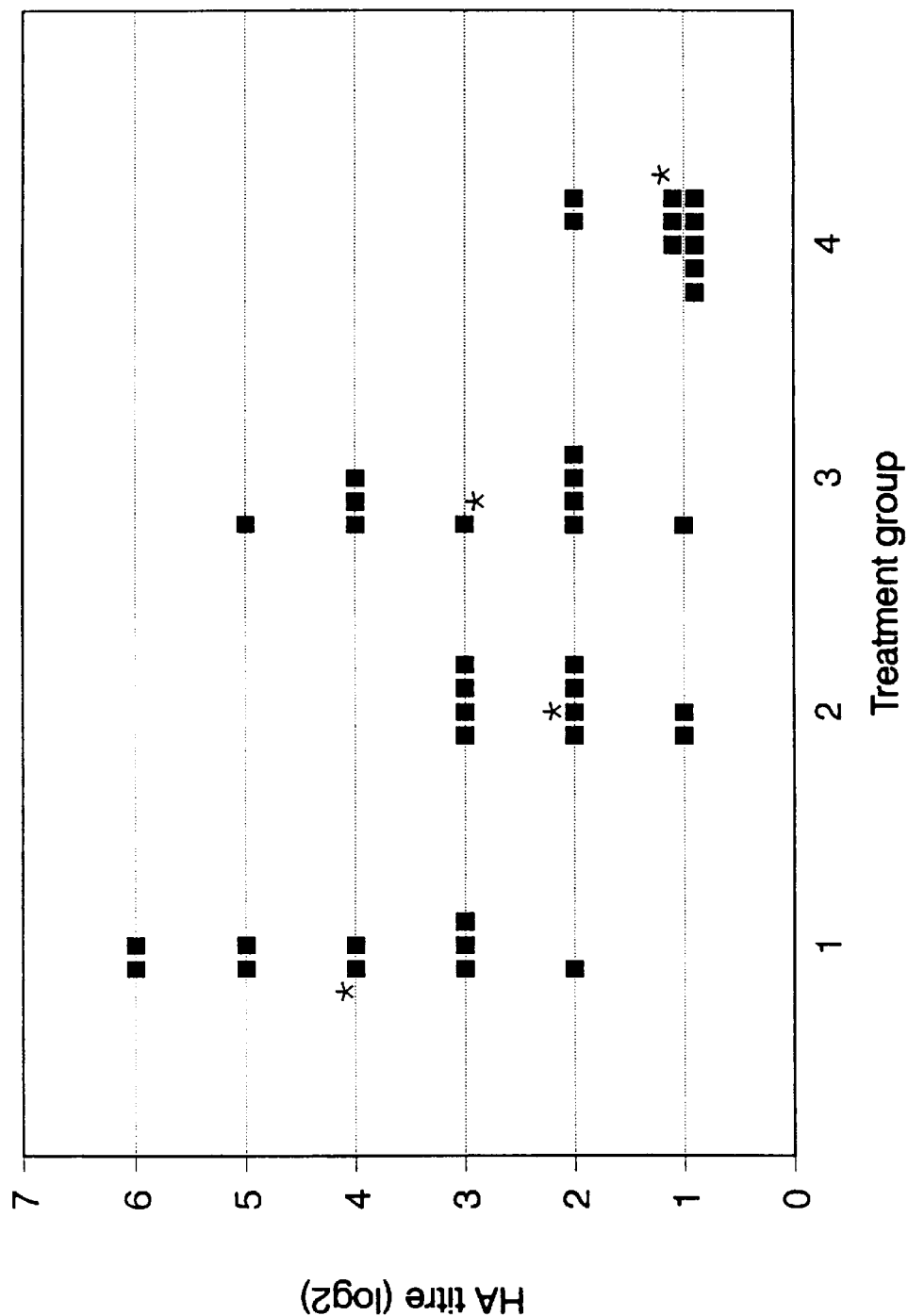
Figure 15C:
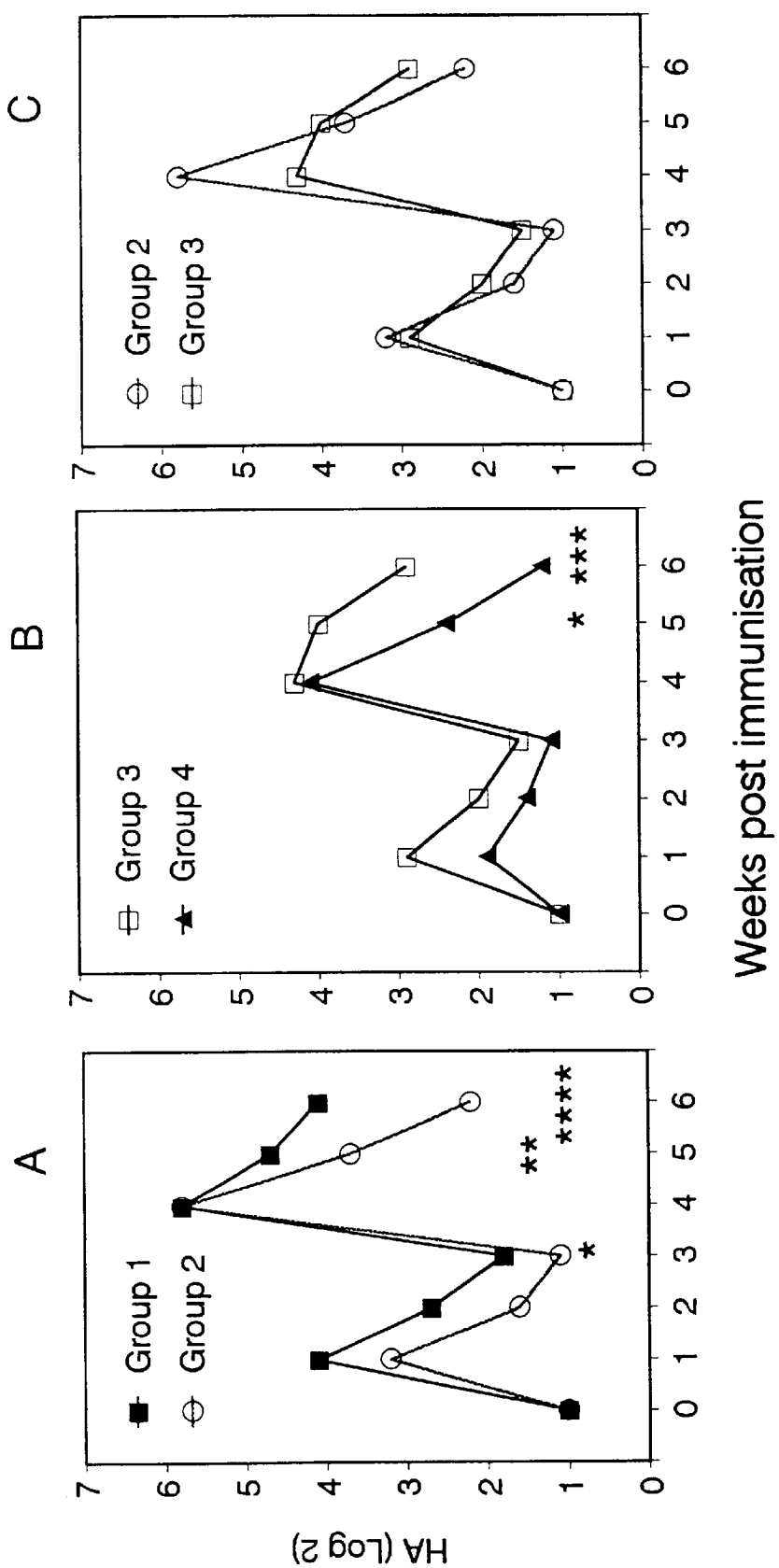
Figure 15D:
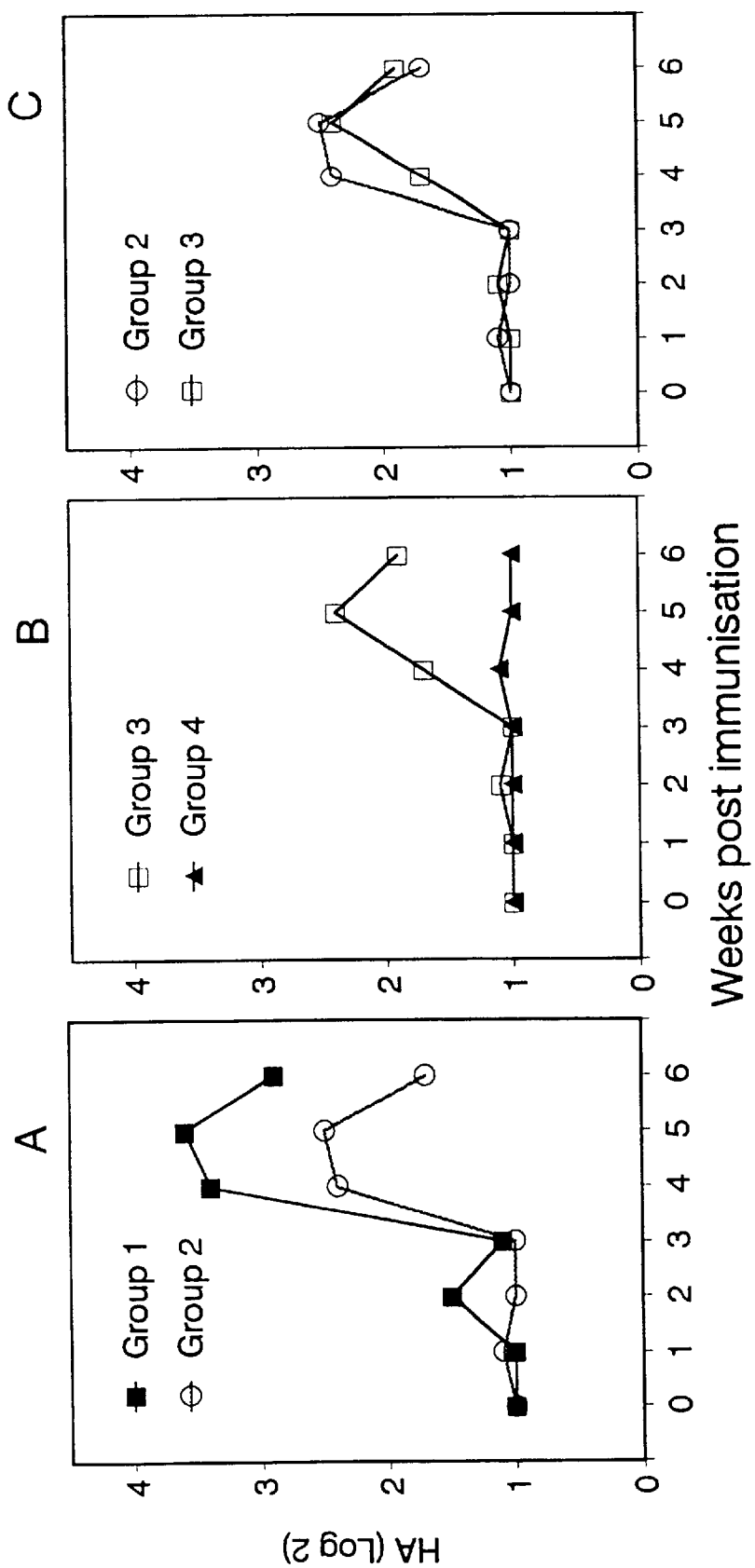

FIG. 14B shows the percentage inhibition by Mab 80.9 of ChIFN-γ biological activity derived from COS cells, *E. coli,* CS cells, and CK cells infected with rFAV expressing ChIFN-γ. Isolated rChIFN-γ (10 U/ml) samples, or CK cells infected with rFAV expressing rChIFN-γ, were incubated for 1 hr in the presence of various concentrations of Mab 80.9, followed by the addition of HD11 cells and the determination of nitrite release therefrom. FIG. 14C shows competition ELISA results for various anti-ChIFN-γ Mabs indicated in the figure. Biotinylated Mab 80.9 (bio80.9; 0.5 ug/ml) was mixed with varying concentrations of different non-labelled Mabs prior to incubation in wells coated with *E. coli*-derived ChIFN-γ. After washing, the amount of bio80.9 bound to the wells was detected by addition of HRP-streptavidin followed by tetra-methyl benzidine (TMB) peroxidase substrate.

FIG. 15 is a graphical representation showing the effect of recombinant ChIFN-γ treatment in vivo on the antibody response to SRBC. Groups of birds were injected with 200 µl (Groups 1 and 2) or 20 µl (Groups 3 and 4) of SRBC and re-immunised after 3 weeks. Groups 1 and 3 were treated with recombinant ChIFN-γ (on the day before, on the day of, and on the day after primary immunisation) and Groups 2 and 4 were not treated. HA titres for total Ig and for IgG (2 mercaptoethanol-resistant Ig titres) were determined weekly for 6 weeks. A, Total Ig HA titres 3 weeks after the primary immunisation; B. Total Ig HA titres 3 weeks after secondary immunisation; C, Total Ig HA titres (there are significant differences between Group 1 and 2 and between Group 3 and 4: *p<0.02, p<0.05, *p<0.005, ****p<0.002); D, IgG HA titres.

Figure 16:
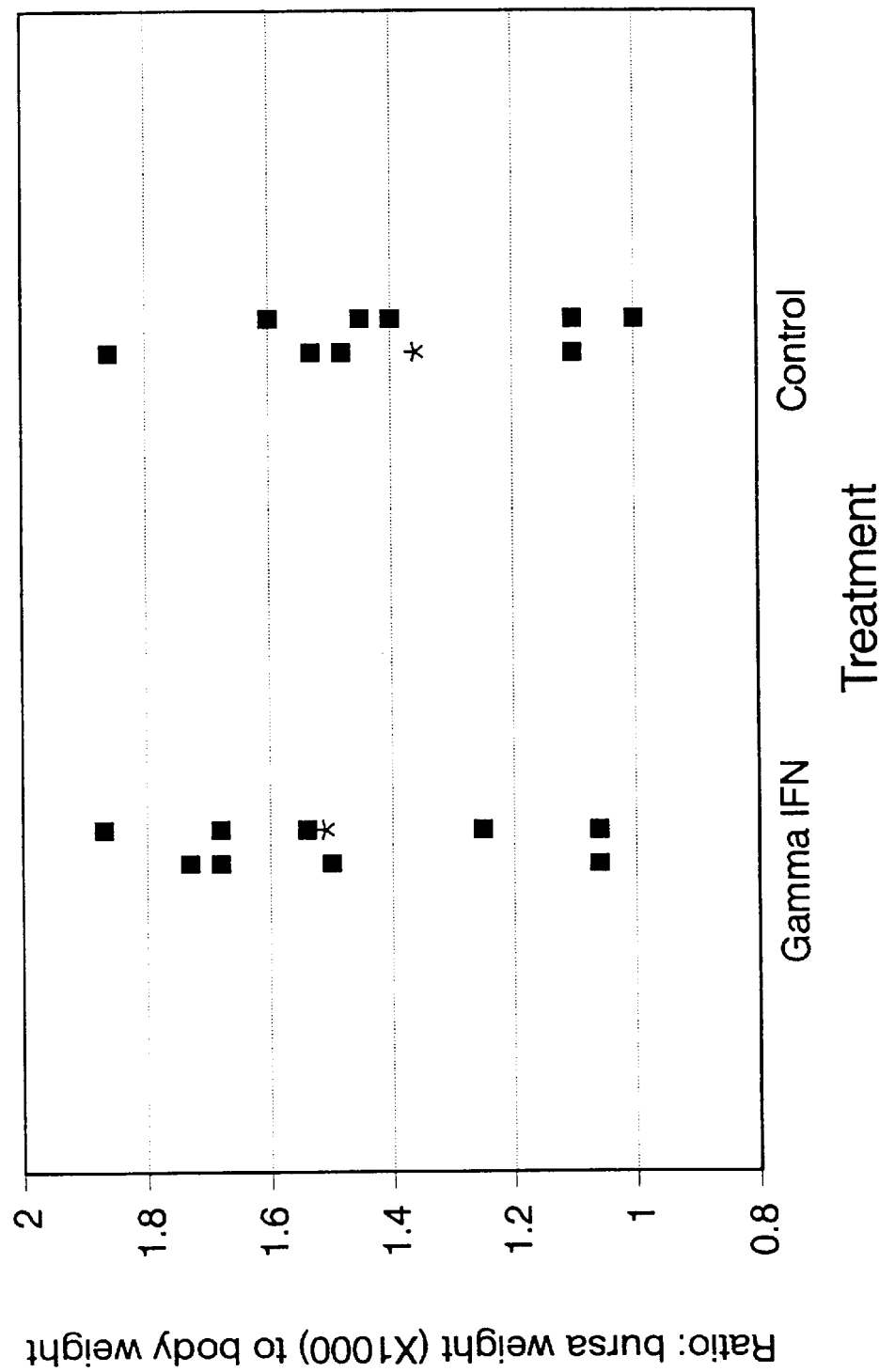

FIG. 16 is a graphical representation showing the effect of recombinant ChIFN-γ treatment in vivo on the ratio of bursa to body weight 7 days following infection with IBDV.

Figure 17:
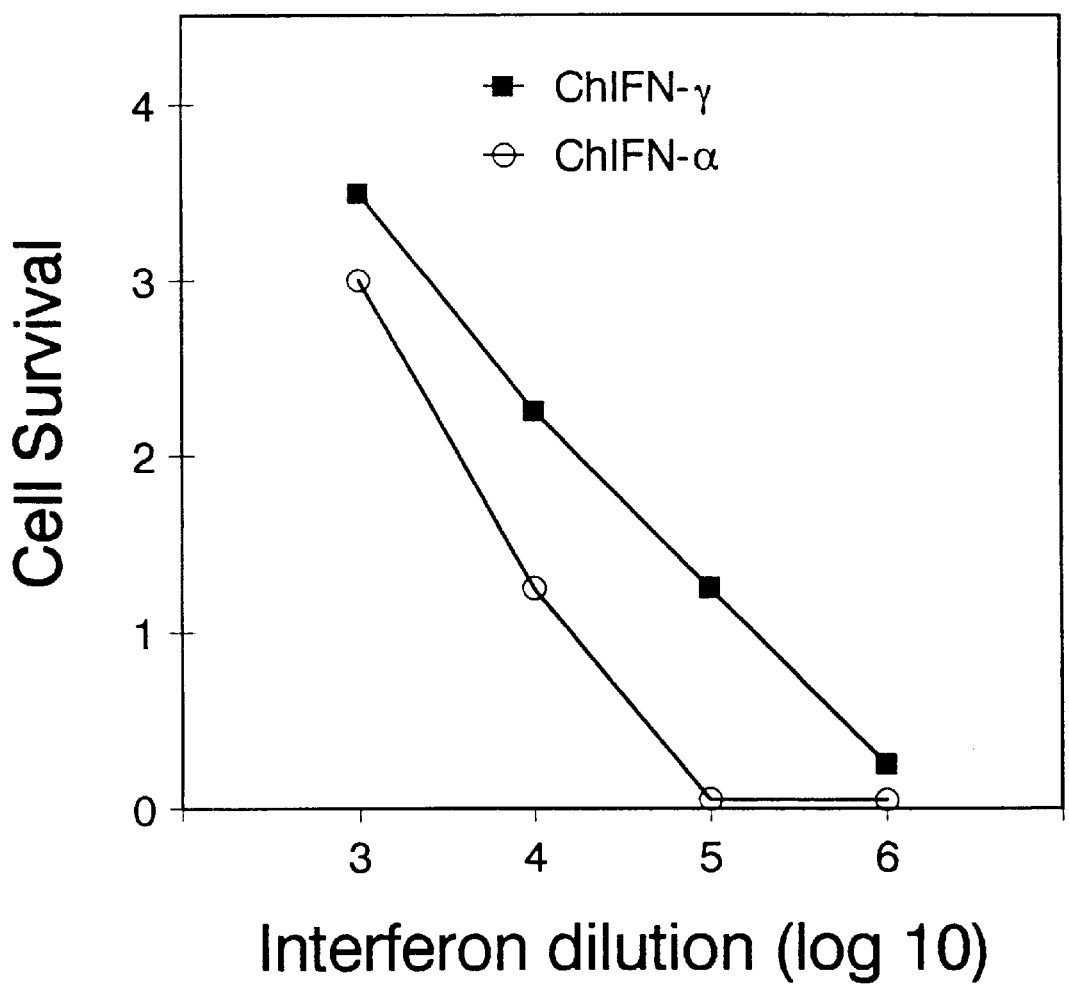

FIG. 17 is a graphical representation showing the effect of recombinant ChIFN-γ treatment in vitro on the ability to protect CEFs from infection with IBDV. CEFs were prepared as described for the CEF interferon assay. Recombinant ChIFN-γ and IBDV were added to the cultures together. Cell survival was measured 3 days later on a scale of 0 to 4, where 0 represents the level of cell survival observed in the presence IBDV and the absence of IFN (<5% cell survival) and 4 represents the level of cell survival observed in the absence of IBDV (>90% cell survival).

Figure 18:
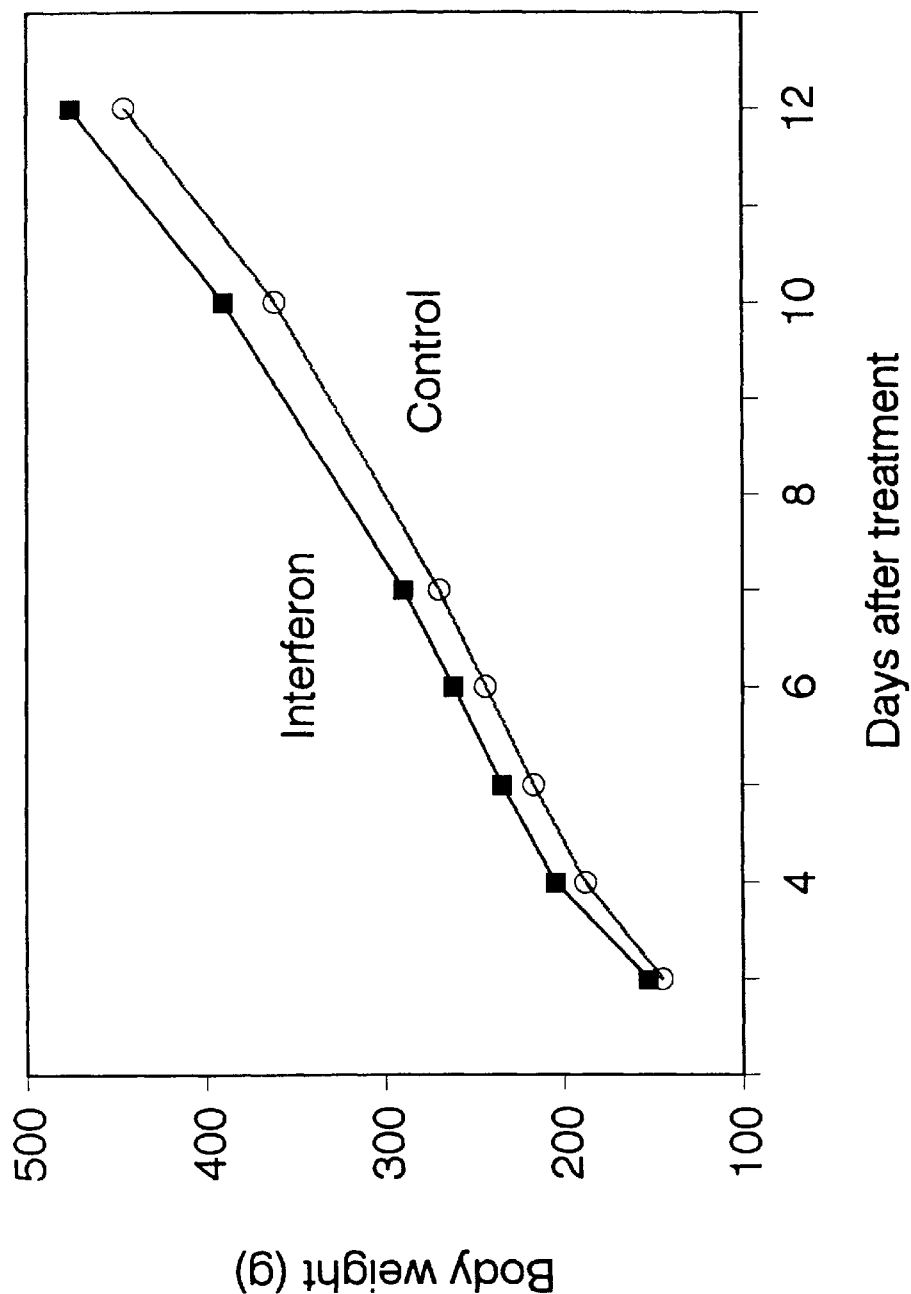

FIG. 18 is a graphical representation showing the effect of recombinant ChIFN-γ treatment in vivo on weight gain. Groups of 10 birds were injected with recombinant ChIFN-γ or with diluent and their body weight was monitored.

Figure 19:
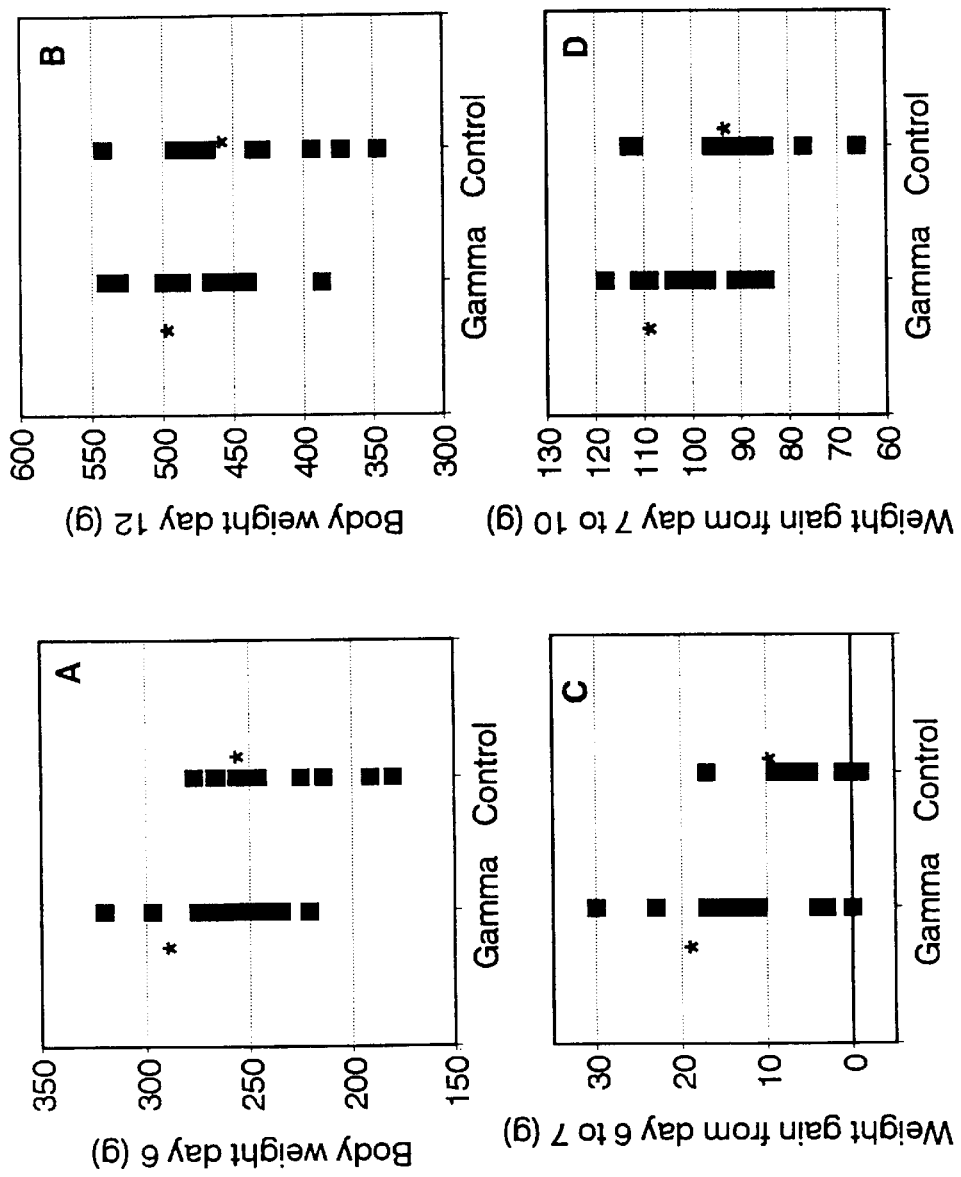

FIG. 19 provides graphical representations showing the effect of recombinant ChIFN-γ treatment in vivo on weight gain. Birds were injected with recombinant ChIFN-γ or with diluent and their body weight was determined at days 6 (FIG. 19A) and 12 (FIG. 19B). Weight gain between days 6 and 7 is shown in FIG. 19C and between days 7 and 10 is shown in FIG. 19D.

Figure 20:
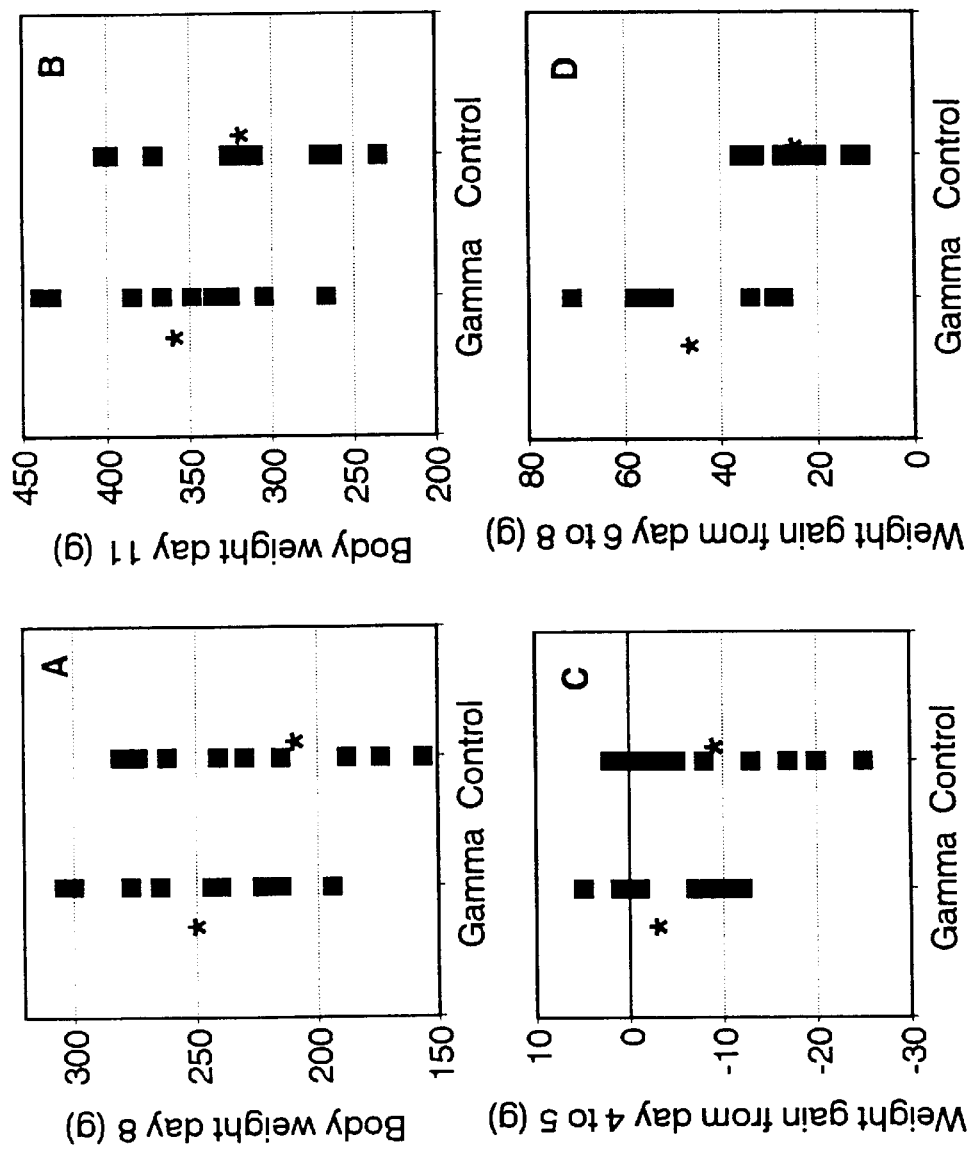

FIG. 20 provides graphical representations showing the effect of recombinant ChIFN-γ treatment in vivo on weight gain during infection with *E. acervulina.* Birds were injected with recombinant ChIFN-γ or with diluent, infected with *E. acervulina* oocytes, and their body weight was determined at day 8 (FIG. 20A) and day 11 (FIG. 20B) post-infection. Changes in weight between days 4 and 5 are shown in FIG. 20C, and changes in weight between day 6 and day 8, are shown in FIG. 20D.

Figure 21:
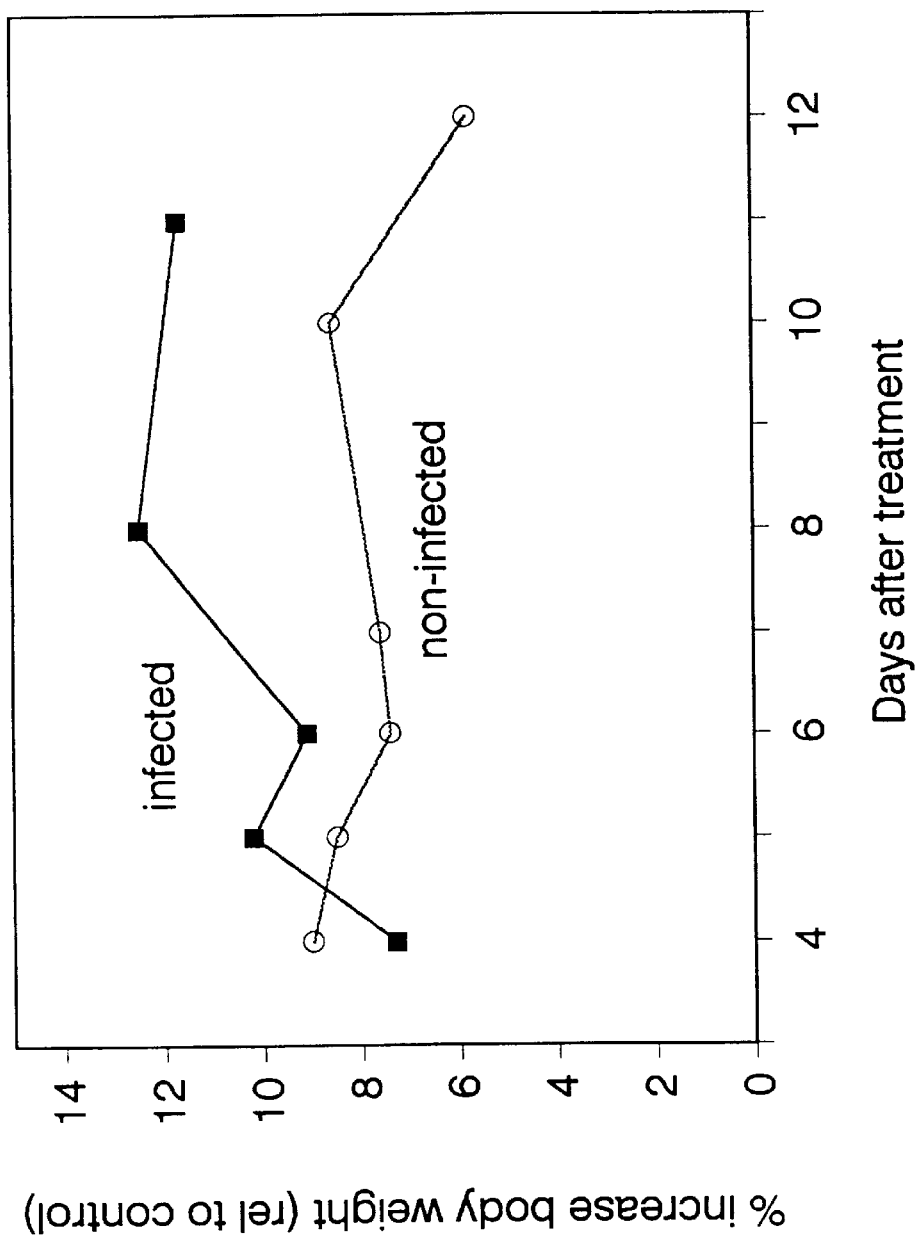

FIG. 21 is a graphical representation showing the effect of recombinant ChIFN-γ treatment in vivo on weight gain in non-infected birds and those infected with coccidiosis.

Figure 22:
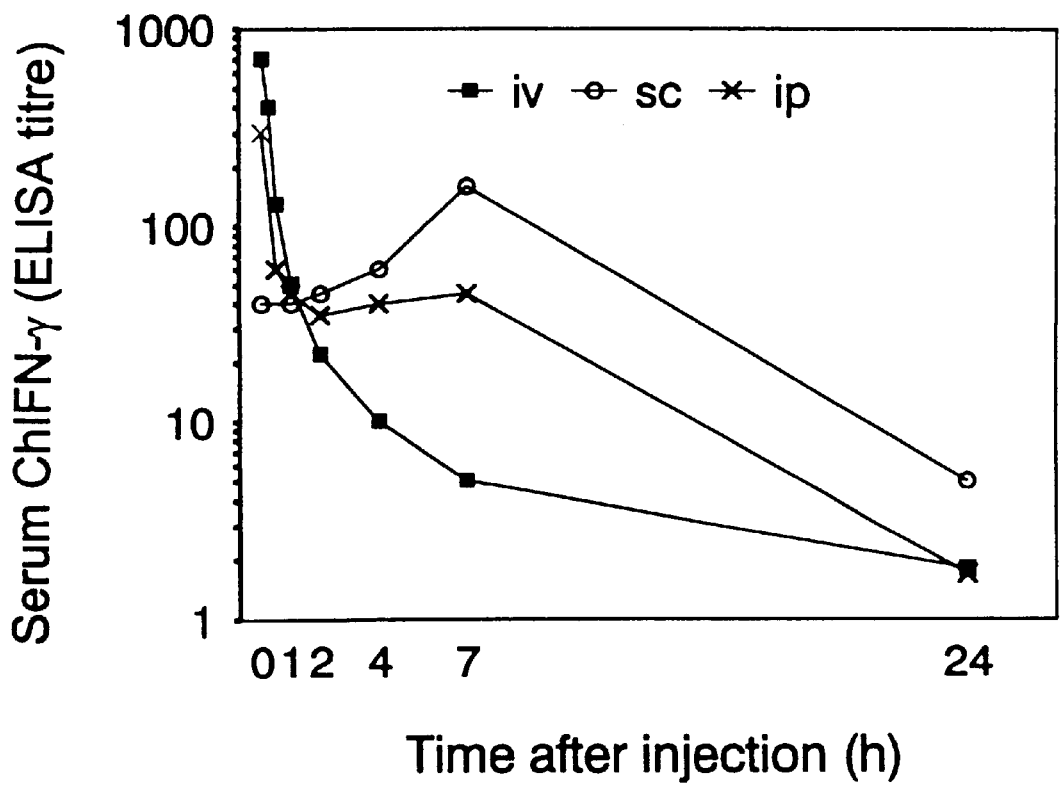

FIG. 22 is a graphical representation showing ELISA detection of ChIFN-γ in the serum of chickens following i/v, s/c or i/p injection of 5000 Units of *E coli*-derived ChIFN-γ. Similar results were obtained in 2 experiments.

Figure 23:
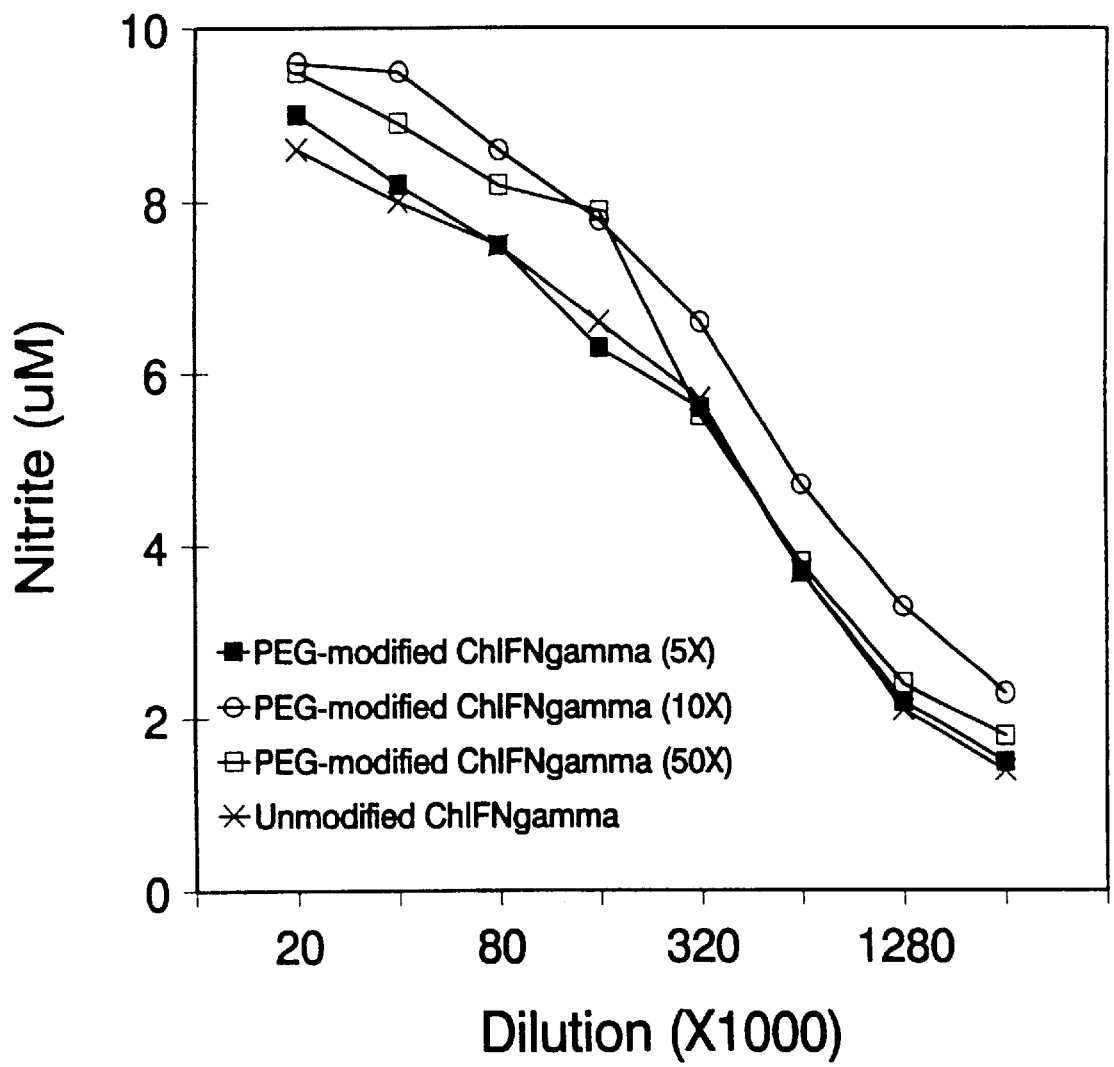

FIG. 23 is a graphical representation showing the quantization of biological activity of ChIFN-γ modified by CC-PEG. Nitrite release from HD11 cells was determined following treatment of *E. coli*-produced rChIFN-γ protein with 5-fold, 10-fold, and 50-fold molar excesses of CC-PEG. Data indicate no difference in activity compared to unmodified ChIFN-γ.

Figure 24:
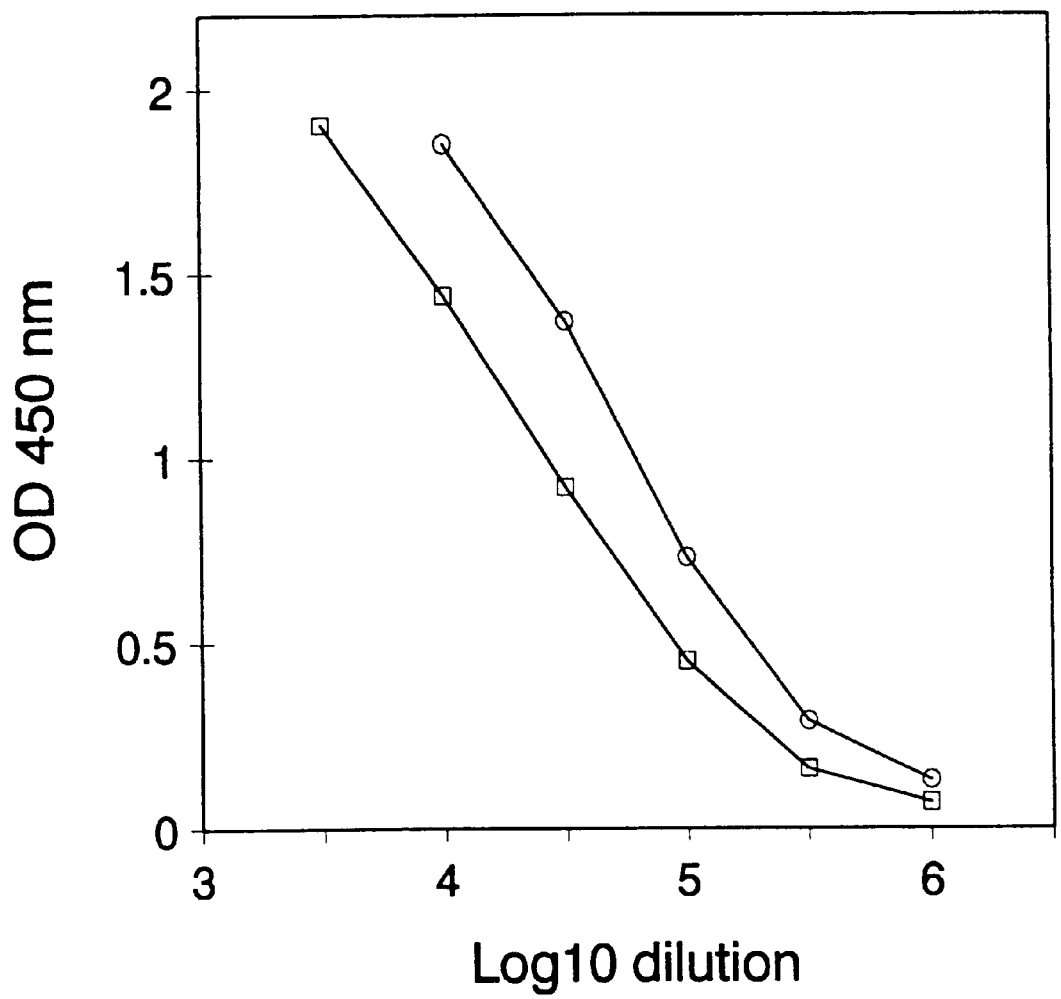

FIG. 24 is a graphical representation showing the quantization of biological activity of ChIFN-γ following treatment with a 30-fold molar excess of CC-PEG (□) compared to unmodified ChIFN-γ (○), as determined by ELISA.

Figure 25:
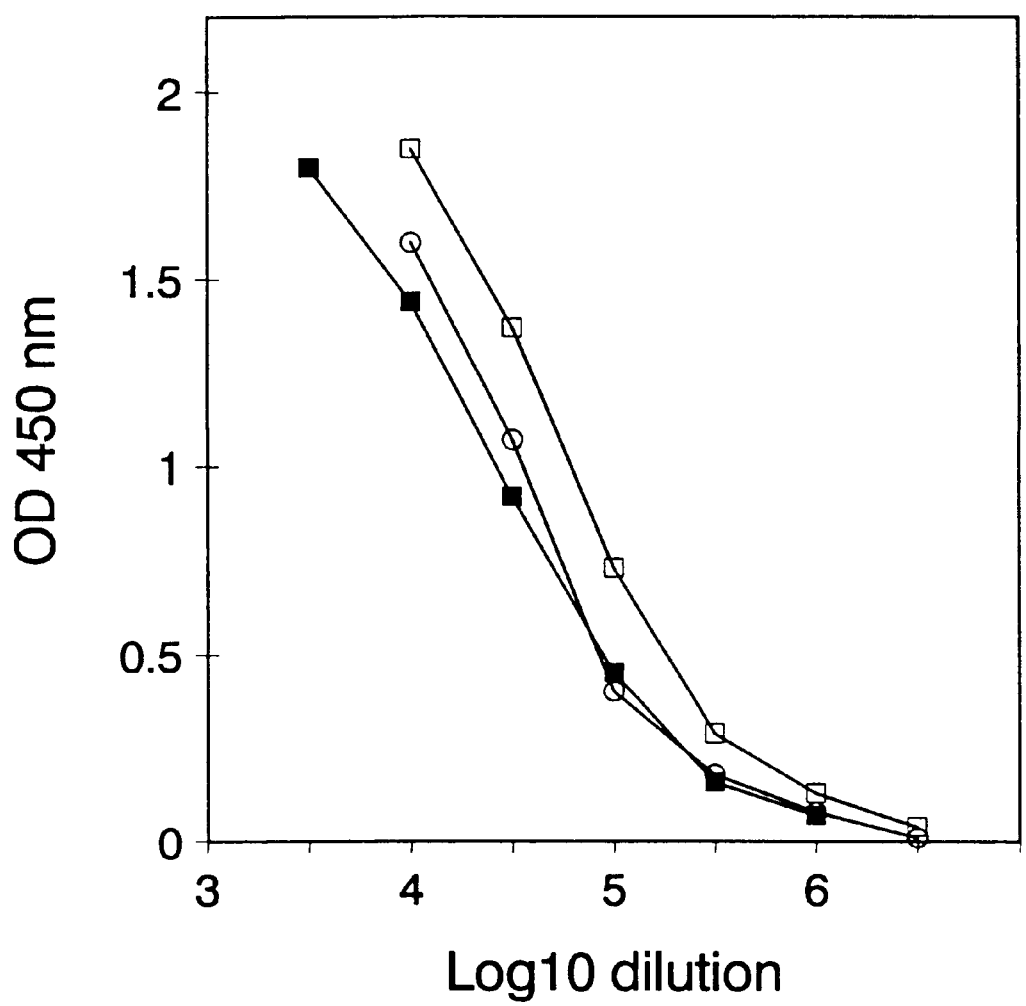

FIG. 25 is a graphical representation showing the quantization of biological activity of ChIFN-γ following treatment with a 30-fold molar excess of CC-PEG (■), or a 30-fold molar excess of NC-PEG (○), compared to unmodified ChIFN-γ (□), as determined by ELISA.

Figure 26:
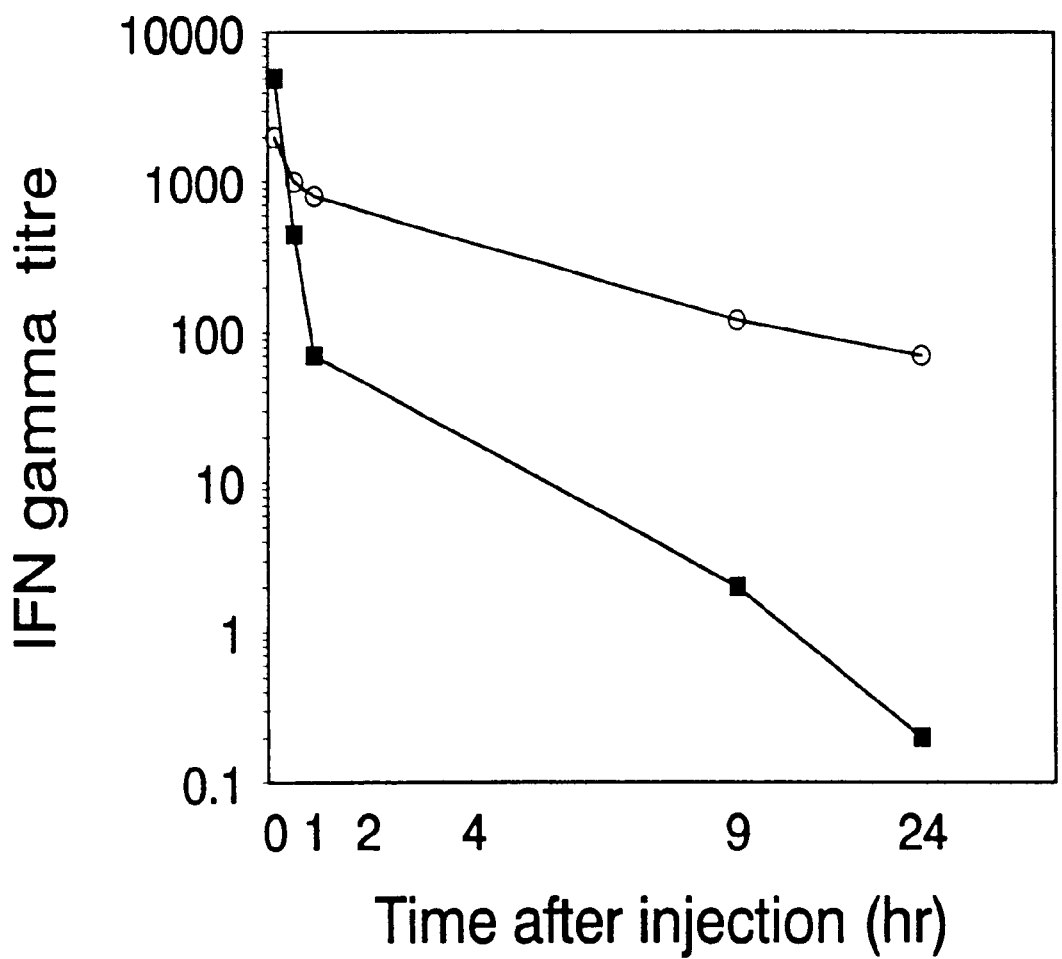

FIG. 26 is a graphical representation comparing the half-lives of CC-PEG modified ChIFN-γ (○) and unmodified ChIFN-γ (■) in the serum of chickens following intravenous injection thereto, as determined by ELISA.

Figure 27:
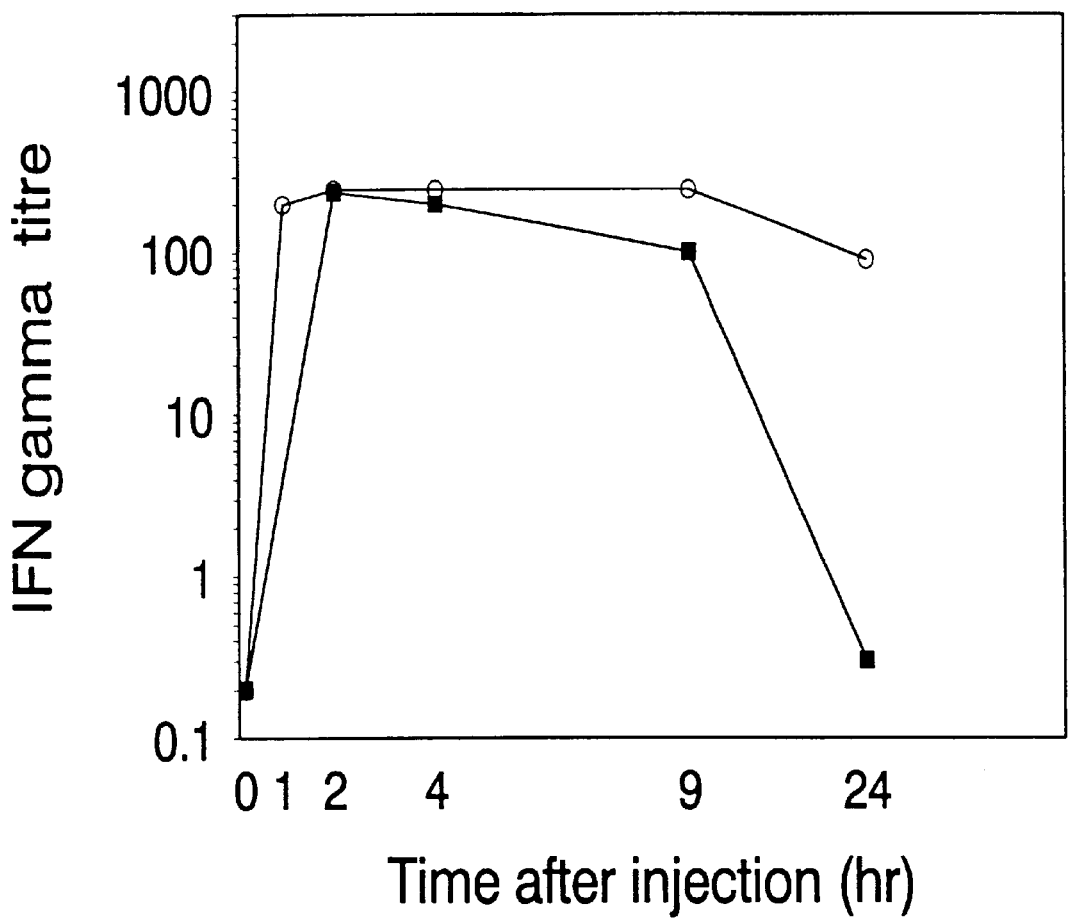

FIG. 27 is a graphical representation comparing the half-lives of CC-PEG modified ChIFN-γ (○) and unmodified ChIFN-γ (■) in the serum of chickens following intraperitoneal injection thereto, as determined by ELISA.

Figure 28:
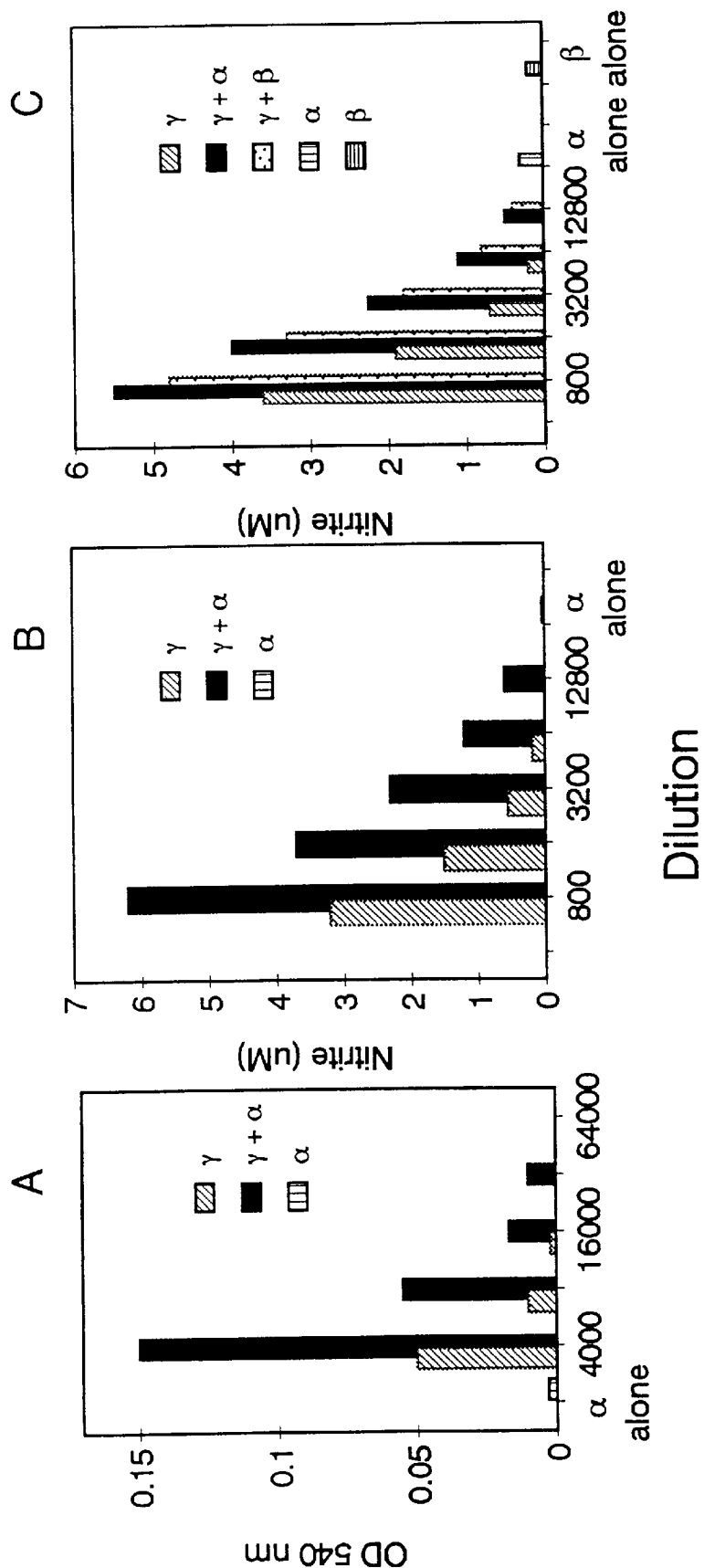

FIG. 28 provides graphical representations showing the ability of ChIFN-γ and ChIFN-α to synergise. In FIG. 28A, the IFN activity is determined using the CEF assay. In FIG. 28B and FIG. 28C, IFN activity is measured using the nitrite assay. Recombinant ChIFN-γ was serially diluted in the presence of limiting amounts of recombinant ChIFN-α or natural ChIFN-β.

DETAILED DESCRIPTION OF THE INVENTION

1. General

Recombinant avian IFN-γ or interferon-like molecules contemplated herein or cells expressing same, will find particular application in the intensive livestock industries such as the live animal export trade, feed-lots and intensive rearing industries. In particular, livestock such as poultry, domestic birds and game birds are highly susceptible to infectious diseases, such as those transmitted by viruses, bacteria or Mycoplasma. Important viral infectious agents include infectious bursal disease virus, avian infectious bronchitis virus, avian infectious laryngeotracheitis virus, infectious bronchitis virus, Newcastle disease virus, Marek's Disease virus, chicken anemia virus or avian influenza virus, amongst others. Important bacterial agents include *E. coli,* Salmonella ssp. or Eimeria ssp., amongst others. Conditions in poultry, domestic bird or game birds for which treatment might be required include infectious disease induced by any viral or bacterial agent such as those discussed supra, cancer, immunosuppression, allergy and to enhance or suppress reproductive systems. Conditions would also include situations where animals are in an immuno-compromised state such as during or following stress, due to overcrowding and transport process, changes in climate.

Whilst not being bound by any theory or mode of action, avian cytokines such as IFN-γ or interferon-like molecules, in particular ChIFN-γ induce macrophages to become activated, as measured by the increased expression of Class II molecules on their surfaces and/or the increased secretion of active nitrogen intermediates such as nitrites, thereby increasing the capacity of the immune system to destroy invading pathogens and to enhance the immune response thereto.

The present invention provides an opportunity to enhance the immune responsiveness and growth performance of birds and in particular poultry, domestic birds or game birds, by the administration of an avian cytokine, in particular a IFN-γ such as ChIFN-γ or a derivative thereof, either directly or via the expression of recombinant genetic sequences. This is of particular importance since most subunit and synthetic peptide vaccines are only weakly antigenic. The administration of the cytokines may be alone, in combination with an antigen or as a fusion molecule. Administration may be via an attenuated virus, recombinant viral vector or bacterial vector or may be by administration of the cytokine by, for example, injection or oral ingestion (e.g. in medicated foodstuff).

2. Description of the Preferred Embodiments

One aspect of the present invention provides a method of treatment or prophylaxis of birds exposed to or infected with a pathogenic organism, said method comprising administering thereto an immunoresponsive-effective amount of an avian IFN-γ cytokine polypeptide for a time and under conditions sufficient to maintain, stimulate or enhance the immmunoresponsiveness of said bird, wherein said avian IFN-γ cytokine polypeptide is selected from the group consisting of:

(a) a polypeptide having the amino acid sequence set forth in any one of SEQ ID NOs: 2–7;

(b) a polypeptide having the amino acid sequence set forth as the mature protein region of any one of SEQ ID NOs: 2–7;

(c) a polypeptide encoded by DNA present in an avian DNA library, wherein said DNA hybridizes under conditions of at least moderate stringency with a probe having a sequence complementary to at least 50 contiguous nucleotides of SEQ ID NO: 1;

(d) a polypeptide encoded by a nucleotide sequence that is degenerate with a DNA molecule according to (c); and (e) a polypeptide comprising at least 10 contiguous amino acids of any one of SEQ ID NOs: 2–7, wherein said polypeptide has immunomodulatory activity.

By prophylaxis" is meant the prevention of infection by a viral or bacterial pathogen of birds, such as, for example, that achieved by vaccination.

The term "avian" means a member of the class of vertebrates commonly referred to as birds. As used herein, the term "avian" includes both sexes and all developmental stages of poultry species, domestic birds and game birds selected from the list comprising chickens, turkeys, bantams, quails, guinea fowl, ducks, geese, ostriches, emus, pigeons, canaries, budgerigars, parrots and finches, amongst others.

Hereinafter the term "cytokine polypeptide" shall be taken to refer to a polypeptide molecule comprising at least one subunit of a biologically-active protein which possesses one or more of the characteristic biological features of a cytokine, in particular the ability to affect the functions of a cell which functions in the immune system of an animal.

Hereinafter the term "IFN-γ" shall be taken to refer to a cytokine polypeptide as hereinbefore defined wherein said cytokine possesses at least one, preferably at least two, more preferably at least three, even more preferably at least four, still even more preferably at least five and most preferably six of the following characteristic properties:

(i) It is capable of preventing virus-mediated lysis of an avian cell such as, but not limited to a chicken embryonic fibroblast cell or a turkey embryonic fibroblast cell;

(ii) It is sensitive to treatment comprising high temperature, preferably temperatures of at least 500° C., more preferably at least 60° C.;

(iii) It is sensitive to exposure to low pH, preferably pH values between 1 and 6, more preferably pH values between 1 and 3, in particular a pH value of 2.0;

(iv) It is capable of inducing macrophages to secrete reactive nitrogen intermediates such as nitrite, nitrate or nitric oxide, amongst others;

(v) It functions as an immunomodulatory molecule in an avian species; and (vi) It functions as a growth-enhancing or growth-promoting agent in an avian species.

Reference herein to "IFN-γ" shall also be taken to include all possible fusion molecules between a said polypeptide as hereinbefore defined and another polypeptide, in particular a Type I interferon molecule such as IFN-α or IFN-β or, alternatively, a second Type II interferon or Type II interferon-like molecule.

As used herein, the term "immunomodulatory molecule" shall be taken to refer to a composition of matter that is capable of altering any immune response of an animal to any antigen, such as, for example, a composition of matter that is a peptide, polypeptide, protein, vaccine, vaccine, hapten, adjuvant, or organism, amongst others. Accordingly, an "immunomodulatory molecule" includes a peptide, polypeptide, protein, subunit vaccine, or killed organism that is capable of altering the immune response of an animal to an agent, such as, for example, a disease-promoting agent, an infectious agent, or a cancer-inducing agent, amongst others. The present invention is particularly directed to avian IFN-γ polypeptides which are at least capable of altering an immune response in a bird or alternatively a fusion molecule comprising same which is at least capable of altering an immune response in a bird or mammal to an antigen or infectious agent such as, but not limited to infectious bursal disease virus (IBDV), infectious bronchitis virus, avian infectious laryngeotracheitis virus, infectious bronchitis virus, Newcastle disease virus, Marek's Disease virus, chicken anemia virus, avian influenza virus, *E. coli,* Salmonella ssp., Eimeria ssp. or Mycoplasma ssp. amongst others, to alleviate symptoms associated therewith, in particular reduced growth performance.

As used herein, the terms "immunoresponsive-effective amount" and "immunomodulatingly effective amount" or similar, shall be taken to refer is an amount of cytokine sufficient to effect immunomodulation in a target animal or to enhance the ability of the immune system to develop an effective immune response to an antigen or pathogenic organism and/or to enhance the immunogenicity of an antigen administered to said animal in a vaccine composition and/or to generally enhance the immunocompetence of the animal.

The administered IFN-γ molecule according to the present invention may be any Type II interferon molecule, preferably an avian IFN-γ polypeptide, the only requirement being that said Type II interferon molecule possesses functional and/or structural similarity to an avian IFN-γ cytokine polypeptide, such as, for example, sufficient structural similarity so as to be immunologically cross-reactive with an avian IFN-γ polypeptide, or to be at least 40% identical thereto at the amino acid sequence level as determined using any algorithm known by those skilled in the art.

The term "growth-enhancing or growth promoting agent" or similar term shall be taken to refer to the capability of a substance to lead to increased weight in an avian species or to prevent weight losses normally detectable during or following pathogenic infection of an avian species, when administered thereto, either in any form such as a vaccine, adjuvant, recombinant polypeptide, synthetic polypeptide, pharmaceutical composition or therapeutic foodstuff, amongst others.

The present inventors have shown that an avian IFN-γ cytokine polypeptide may function as a growth-enhancing or growth-promoting agent in an avian species, and that it may stimulate, enhance or maintain the immmunoresponsiveness of a bird, and the possibility exists that the growth-promoting effect of said polypeptide may be a consequence of immune-enhancement, however the present invention is not to be limited by any theory or mode of action of said polypeptide.

In a preferred embodiment, the avian IFN-γ cytokine polypeptide is derived from a species of poultry selected from the list comprising chickens, ducks, geese, turkeys, bantams, quails or guinea fowl, amongst others. In a particularly preferred embodiment, the avian IFN-γ cytokine polypeptide is derived from chickens.

As used herein, the term "derived from" shall be taken to indicate that a particular integer or group of integers has originated from the species specified, but has not necessarily been obtained directly from the specified source.

Several recombinant avian IFN-γ cytokine polypeptides have now been described, including those polypeptides derived from chickens (U.S. Ser. No. 08/765,381) and having the amino acid sequence set forth herein as SEQ ID NO: 2, ducks (SEQ ID NO: 3; personal communications of Dr Ursula SCHULTZ of Scripps Research Institute 10550 North Torrey Pines Road, La Jolla, Calif. 92037, United States of America); turkey (SEQ ID NO: 4; Kaiser et al., 1990); Ring-necked pheasant (SEQ ID NO: 5), Japanese quail (SEQ ID NO: 6); and Guinea fowl (SEQ ID NO: 7). All of the gene sequences encoding these Polypeptides have been isolated based upon the nucleotide sequence of the chicken IFN-γ cDNA set forth in the present specification as SEQ ID NO: 1. The IFN-γ activity of recombinant duck IFN-γ-encoding clone has been confirmed by measuring the anti-viral protection conferred in both chicken and duck cells and, as expected for authentic duck IFN-γ, recombinantly-expressed duck IFN-γ has significant anti-viral activity in both duck cells and chicken cells, however approximately 32-fold the anti-viral activity in duck cells that is observed in chicken cells. Recombinant turkey IFN-γ also has anti-viral activity in chicken cells.

There are no gaps in the amino acid sequence alignments between chicken, duck, Guinea fowl, pheasant, quail and turkey IFN-γ polypeptides and these sequences are all highly-conserved. Based on the proportion of identical residues in the alignment between chicken and duck IFN-γ polypeptides, there is 67% amino acid sequence identity between these sequences over the entire length of chicken IFN-γ (i.e. amino acids −19 to 145 of SEQ ID NO: 2 in the present specification) and 64% identity in the mature secreted protein region (i.e. amino acids 1 to 145 of SEQ ID NO: 2 in the present specification). The derived amino acid sequences of the Guinea fowl, pheasant, quail and turkey IFN-γ polypeptides have 87.8% (guinea fowl) to 97.6% (turkey and pheasant) amino acid sequence identity with chicken IFN-γ over their entire length (i.e. amino acids corresponding to positions −19 to 145 of SEQ ID NO: 2 in the present specification) and 86.2% (guinea fowl) to 97.2% (turkey and pheasant) identity in the mature secreted protein region (i.e. amino acids corresponding to positions 1 to 145 of SEQ ID NO: 2 in the present specification). These percentage identities to chicken IFN-γ were determined by simple calculation of the number of identical residues, expressed as a proportion of the total number of residues in the aligned sequences, because of the absence of any gaps in the alignments.

In contrast to the high homology between avian IFN-γ polypeptide, the aligned avian and mammalian IFN-γ polypeptides set forth in FIG. 13 of the present specification reveals only 30% identity using the ClustalW programme and the algorithm of Thompson et al., 1994) or alternatively, 32% calculated using the ClustalV programme.

Based upon the high sequence conservation and function of the various IFN-γ polypeptides, it will be apparent to those skilled in the art that the present invention is readily performed using any avian IFN-γ polypeptide.

Additional avian IFN-γ polypeptides may be obtained by standard procedures known to those skilled in the art, such as, for example, by isolating the corresponding nucleic acid molecules using PCR or hybridisation approaches, and expressing the recombinant polypeptides therefrom. For example, homologous avian IFN-γ-encoding nucleic acid molecules may be obtained by hybridising avian nucleic acid under at least low stringency conditions to the nucleic acid molecule set forth in SEQ ID NO: 1, or to a complementary strand thereof. A "low stringency" is defined herein as being a hybridisation and/or a wash carried out in 6×SSC buffer, 0.1% (w/v) SDS at 28° C., or equivalent. Those skilled in the art will be aware that the stringency is increased by reducing the concentration of SSC buffer, and/or increasing the concentration of SDS and/or increasing the temperature of the hybridisation and/or wash, and that the conditions for hybridisation and/or wash may vary depending upon the nature of the hybridisation membrane or the type of hybridisation probe used. Such conditions are well understood by one normally skilled in the art. For the purposes of clarification of the parameters affecting hybridisation between nucleic acid molecules, reference is found in Ausubel et al (1987), which is herein incorporated by reference.

Particularly preferred homologues of the chicken IFN-γ gene exemplified herein as SEQ ID NO: 1 may be obtained by hybridization under conditions of at least moderate stringency (i.e. 2×SSC buffer, 0.1% (w/v) SDS at 28° C., or equivalent) with a probe having a sequence complementary to at least 50 contiguous nucleotides of SEQ ID NO: 1. Such homologues clearly include nucleotide sequences that are degenerate with SEQ ID NO: 1 (i.e. they encode the amino acid sequence set forth herein as SEQ ID NO: 2), and nucleic acid molecules that encode functional IFN-γ polypeptides and comprise at least 10 contiguous amino acids of SEQ ID NO: 2.

In the case of PCR, one or more nucleic acid primer molecules of at least about 10 nucleotides in length derived from the Ch IFN-γ gene may be used to isolate such variant sequences.

Preferably, the administered polypeptide is a recombinant molecule. By "recombinant molecule" or "recombinant polypeptide" is meant a peptide, oligopeptide, polypeptide, protein or enzyme molecule that is produced by expressing non-endogenous nucleic acid encoding IFN-γ in a cell, tissue, organ or whole organism, such as, for example, the expression of foreign nucleic acid in a cell tissue, organ or whole organism that is different from the original cell, tissue, organ or organism from which said nucleic acid was derived, albeit not necessarily of a different species. Accordingly, a recombinant chicken IFN-γ polypeptide may be produced by expressing chicken IFN-γ-encoding nucleic acid in a chicken cell provided that said chicken cell is not the same cell from which said nucleic acid was originally derived (i.e. Provided that the nucleic acid is non-endogenous), or alternatively, by expressing chicken IFN-γ-encoding nucleic acid in a non-chicken cell.

Several means may be employed to produce a recombinant polypeptide. Generally, a recombinant avian IFN-γ polypeptide will be produced following transfection of cells with the nucleic acid molecule encoding said polypeptide, wherein the introduced nucleic acid is maintained as an extrachromosomal element for a time and under conditions sufficient for expression to occur. In an alternative embodiment, the nucleic acid molecule may be expressed following its integration into the genome of a cell as an addition to the endogenous cellular complement of cytokine genes. Generally, to obtain expression, the introduced nucleic acid molecule contains a promoter sequence derived from the same or another gene, which regulates the expression of the IFN-γ gene sequence contained therein. Means for the introduction of nucleic acid to prokaryotic and eukaryotic cells will be well-known to those skilled in the art.

Preferably, the nucleic acid molecule that is used to produce a recombinant avian IFN-γ polypeptide comprises a sequence of nucleotides substantially the same as or complementary to the nucleotide sequence set forth in SEQ ID NO: 1 or a homologue, analogue or derivative thereof including any single or multiple nucleotide substitutions, deletions and/or additions thereto. For the purposes of nomenclature, the nucleotide sequence set forth in SEQ ID NO: 1 relates to the chicken IFN-γ cDNA sequence, referred to hereinafter as the "ChIFN-γ gene", which is expressed in activated T cells and NK cells to produce a polypeptide which is capable of stimulating macrophages to produce reactive nitrogen intermediates such as nitric oxide, nitrate or nitrite.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence shall be taken to refer to any isolated nucleic acid molecule which contains significant sequence similarity to said sequence or a part thereof. Generally, the nucleotide sequence is subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

The present inventors have produced several N-terminal and C-terminal addition and deletion variants of the chicken IFN-γ cDNA sequence set forth in SEQ ID NO: 1 of the present specification. In particular, the inventors have produced variants wherein the N-terminal 4 amino acid residues and/or the C-terminal 12 amino acid residues of chicken IFN-γ have been deleted and/or an additional 8 amino acid residues in the form of a polyhistidine tag (His-His-His-His-His-His-Gly-Ser) have been added to the N-terminal or C-terminal ends of the chicken IFN-γ polypeptide. The variant IFN-γ polypeptides were produced in *E. coli* cells, or alternatively, expressed in tobacco plants using the tobacco mosaic virus (TMV) vector and their specific activities determined using the HD11 nitrite assay described in Example 6 of the present specification. Accordingly, the present inventors have shown that there is no difference in IFN-γ specific activity between the variant sequences (His1-Cys145 with a C-terminal or N-terminal tag; His1-Lys133 with or without an N-terminal tag; and Ser5-Cys145 with an N-terminal tag) and the wild-type mature chicken IFN-γ polypeptide (i.e. His1-Cys145 without any N-terminal or C-terminal tag). There is also no difference in the activities of wild-type mature chicken IFN-γ or the variant sequences over a wide range of dilutions. Moreover, the IFN-γ activity of the variant sequences expressed from TMV in tobacco plant cells, which is inhibited by antisera prepared against recombinant chicken IFN-γ, is not significantly different from the activity of the wild-type mature chicken IFN-γ polypeptide over a wide range of dilutions. Accordingly, derivatives of SEQ ID NO: 2 can be produced which exhibit biological-activity in a wide range of cell and tissue types, without undue experimentation, in particular derivatives that comprise up to 4 amino acids deleted from the N-terminus and/or up to 12 amino acids deleted from the C-terminus and/or up to 8 amino acids added to the N-terminus or the C-terminus of said amino acid sequence.

The nucleic acid that is used to produce a recombinant polypeptide may comprise RNA or DNA or a combination thereof. Preferably, the nucleic acid is a gene that encodes an avian IFN-γ polypeptide. Reference herein to a "gene", including the "ChIFN-γ gene", is to be taken in its broadest context and includes:

(i) a classical genomic gene consisting of transcriptional and/or translational regulatory sequences and/or a coding region and/or non-translated sequences (i.e. introns, 5'- and 3'-untranslated sequences); and/or (ii) mRNA or cDNA corresponding to the coding regions (i.e. exons) optionally comprising 5'- or 3'-untranslated sequences of the gene; and/or (iii) synthetic or fusion nucleic acid molecules encoding all or part of a functional product.

Synthetic avian IFN-γ genes may be derived from a naturally-occurring IFN-γ gene by standard recombinant techniques. Generally, an IFN-γ gene may be subjected to mutagenesis to produce single or multiple nucleotide substitutions, deletions and/or additions. Nucleotide insertional derivatives of the IFN-γ cytokine gene include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

To produce a recombinant avian IFN-γ polypeptide, the nucleic acid molecule encoding said polypeptide may be conveniently positioned within a gene construct, in operable connection with a suitable promoter sequence capable of conferring expression in the cell, tissue, organ or organism in which expression is desired.

By "gene construct" is meant a gene as hereinbefore defined operably connected to one or more non-encoding nucleotide sequences, such as, for example, a promoter sequence, an origin of replication or other sequence required for maintenance and/or replication in a cell, tissue, organ or whole organism. The term "gene construct" clearly includes within its scope isolated an isolated or synthetic nucleic acid molecule (or more particularly, an oligonucleotide) containing an IFN-γ-encoding sequence that is operably connected to a promoter; and a plasmid vector, cosmid vector, bacteriophage vector, virus vector, or recombinant virus comprising said IFN-γ-encoding sequence. As used herein, the term "vector" shall be taken to mean a nucleic acid molecule that is capable of being used to express an avian IFN-γ polypeptide in a cell, tissue, organ or organism (also known as an "expression vector") and preferably being maintained and/or replicated in a cell, tissue, organ or organism, and/or inserted into the chromosome of a cell, tissue, organ or organism.

Any number of expression vectors can be employed depending on whether expression is required in a eukaryotic or prokaryotic cell or a virus particle. Furthermore, it is well-known in the art that the promoter sequence used in the expression vector will also vary depending upon the level of expression required and whether expression is intended to be constitutive or regulated.

Preferred expression vectors are virus vectors. For expression in avian cells, it is particularly preferred to use a fowl adenovirus vector (FAV), such as described in U.S. Ser. Nos. 08/448,617 and 09/272,032, the contents of which are incorporated herein by way of reference. In a particularly preferred embodiment, the vector comprises the right-hand end of FAV serotype 8 (hereinafter "FAV8"). The entire nucleotide sequence of the right-hand end of FAV8 is set forth herein as SEQ ID NO: 8. The entire nucleotide sequence of the FAV8 expression vector is also contained in GenBank Accession No. AF155911.

More particularly, the expression vector is plasmid pJJ383, which contains an 8.5 kilobase NheI fragment of the right-hand end of FAV8 wherein nucleic acid encoding IFN-γ in operable connection with a suitable promoter sequence may be substituted for the 1.3 kilobase SnaBI/SmaI FAV8 fragment of SEQ ID NO: 8, as is described in detail in U.S. Ser. No. 09/272,032.

For expression in plant cells, it is particularly preferred to use a tobacco mosaic virus (TMV) vector, however any plant virus-derived vector system may be used, such as, for example, Gemini virus vectors, nanovirus vectors, and caulimovirus vectors, amongst others. Those skilled in the expression of proteins in plant cells will be aware of publicly available vectors within the scope of this description.

For expression in eukaryotic cells, the gene construct generally comprises, in addition to the nucleic acid molecule of the invention, a promoter and optionally other regulatory sequences designed to facilitate expression of said nucleic acid molecule. The promoter may be derived from a genomic clone encoding an avian IFN-γ molecule, in particular ChIFN-γ or, alternatively, it may be a heterologous promoter from another source. Promoter sequences suitable for expression of genes in eukaryotic cells are well-known in the art. In a preferred embodiment, the promoter is capable of expression in an avian cell.

In connection with this invention, a nucleic molecule comprising the nucleotide sequence set forth in SEQ ID NO:

1 has been cloned into the plasmid vector pCDNA1, which is suitable for expression in eukaryotic COS cells, to produce the plasmid pCDNA3/avian G-IFN. Isolated COS cells containing the pCDNA3/avian G-IFN gene construct have been deposited on Feb. 28, 1995 pursuant to and in satisfaction of the Budapest Treaty on the International Recognition of the Deposit of Microorganisms for the Purposes of Patent Procedure, with the Australian Government Analytical Laboratories (AGAL), 1 Suakin Street, Pymble, New South Wales 2073, Australia, under AGAL Accession No. N95/12388.

Promoter sequences and culture conditions for cells or virus particles which produce high levels of expression are particularly preferred, and, according to this embodiment of the invention, it is particularly preferred for such promoter sequences to be capable of expressing avian IFN-γ polypeptide for a time and at a level sufficient to produce an immunomodulatingly-effect amount of said polypeptide. Those skilled in the art will be aware that highly-active constitutive promoters will be particularly preferred. Such promoter sequences will be well-known to those skilled in the relevant art.

Particularly preferred promoters suitable for expression in animal cells, in particular avian cells, include the SV40 major later promoter (MLP), FAV major later promoter (MLP), cytomegalovirus immediate early promoter (CMVIE), or human adenovirus major late promoter, amongst others. Particularly preferred promoters for use in plant cells include the CaMV 35S or 19S promoter sequences, and nanovirus promoters, amongst others.

The prerequisite for producing intact polypeptides in *E. coli* is the use of a strong promoter with an effective ribosome binding site. Typical promoters suitable for expression in bacterial cells such as *E. coli* include, but are not limited to, the lacz promoter, temperature-sensitive $\lambda_L$ or $\lambda_R$ promoters, T7 promoter or the IPTG-inducible tac promoter. A number of other vector systems for expressing the nucleic acid molecule of the invention in *E. coli* are well-known in the art and are described for example in Ausubel et al (1987) or Sambrook et al (1989).

Numerous plasmid vectors with suitable promoter sequences for expression in bacteria and efficient ribosome binding sites have been described, such as for example, pKC30 (λL: Shimatake and Rosenberg, 1981). pKK173-3 (tac: Amann and Brosius, 1985), pET-3 (T7: Studier and Moffat, 1986) or the pQE series of expression vectors (Qiagen, Calif.), amongst others.

In connection with this invention, a nucleic molecule comprising the nucleotide sequence set forth in SEQ ID NO: 1 has been cloned into a plasmid vector suitable for expression in a bacterial cell and transformed into the bacterium *Escherichia coil* to produce *E. coli* strain pQE ChIFN-γ 3.1. The *E. coli* strain pQE ChIFN-γ3.1 has been deposited on Feb. 16, 1996 pursuant to and in satisfaction of the Budapest Treaty on the International Recognition of the Deposit of Microorganisms for the Purposes of Patent Procedure, with the Australian Government Analytical Laboratories (AGAL), 1 Suakin Street, Pymble, New South Wales 2073, Australia, under AGAL Accession No. N96/9464.

In an alternative embodiment, the present invention extends to a gene construct comprising a nucleic acid molecule which encodes or is complementary to a nucleic acid molecule which encodes an avian cytokine polypeptide or a homologue, analogue or derivative thereof, wherein said polypeptide is a fusion polypeptide between a IFN-γ or IFN-γ-like molecule and either a second IFN-γ or interferon-like molecule or a Type I interferon selected from the list comprising IFN-α, IFN-β, Ch IFN-α or Ch IFN-β, amongst others. To produce such a fusion polypeptide, the nucleic acid molecule which encodes a first coding region comprising an avian cytokine polypeptide or a homologue, analogue or derivative thereof is cloned adjacent to a second coding region, optionally separated by a spacer nucleic acid molecule such that the first coding region and the second coding region are in the same open reading frame, with no intervening stop codons between the two coding regions. When translated, the polypeptide thus produced comprises a fusion between the polypeptide products of the first and second coding regions. A gene construct which encodes a fusion polypeptide further comprises at least one start codon and one stop codon, capable of being recognised by the cell's translational machinery in which expression is intended. Methods for the production of a fusion polypeptide are well-known to those skilled in the art.

Recombinantly-produced avian IFN-γ may be produced in a wide range of cell types. Examples of eukaryotic cells contemplated herein to be suitable for expression include avian, mammalian, yeast, insect, plant cells or cell lines such as COS, VERO, HeLa, mouse C127, Chinese hamster ovary (CHO), WI-38, baby hamster kidney (BHK) or MDCK cell lines. In particular, biologically-active chicken IFN-γ may be produced in *E. coli* cells, yeast cells, tobacco cells, COS cells, and chick kidney (CK) cells. Such cell lines are readily available to those skilled in the art.

Suitable prokaryotic cells include Corynebacterium, salmonella, *Escherichia coli,* Bacillus sp. and Pseudomonas sp, amongst others. Bacterial strains which are suitable for the present purpose are well-known in the relevant art (Ausubel et al, 1987; Sambrook et al, 1989).

According to the present invention, recombinant avian IFN-γ is generally produced according to the method comprising:

(i) introducing into said cell a gene construct comprising a nucleic acid molecule which encodes or is complementary to a nucleic acid molecule which encodes said avian cytokine, placed under the control of a suitable promoter sequence;

(ii) culturing said cell for a time and under conditions sufficient for said nucleic acid molecule to be expressed; and (iii) optionally isolating from said cell said recombinant cytokine molecule.

The present invention is of particular use in the treatment or prophylaxis of poultry, domestic birds or game birds against infection by pathogens selected from the list comprising infectious bursal disease virus (IBDV), avian infectious bronchitis virus, avian infectious laryngeotracheitis virus, infectious bronchitis virus, Newcastle disease virus, Marek's Disease virus, chicken anemia virus, avian influenza virus, *E. coli,* Salmonella ssp., Eimeria ssp. or Mycoplasma ssp. amongst others.

The avian cytokine of the present invention may be administered throughout the life cycle of a bird for which treatment or prophylaxis is indicated. The developmental stage of the bird during which treatment or prophylaxis is most effective will vary depending upon the nature of the pathogen against which protection is sought, including its mode of transmission and period of highest infectivity. By "period of highest infectivity" is meant the developmental stage of the host during which it is most vulnerable to attack by a particular pathogen and/or during which there is a greater probability of incurring livestock losses or reduced productivity as a result of the pathogen infection. The parameters affecting optimum developmental stages of animals for administration of the subject cytokines will be well-known to those skilled in the art.

Accordingly, the method of treatment or prophylaxis of the present invention extends to administration of the subject avian cytokine at any developmental stage in the life cycle of poultry, domestic or game birds for which treatment or prophylaxis is indicated.

The cytokine of the invention may be administered by any means including for example, by injection either in ovo or post-hatching by injection such as intra-peritoneal, intra-dermal, intra-muscular, intra-ocular, intra-venous, subcutaneous or other injection means, by ingestion as a medicated foodstuff or therapeutic foodstuff or by introducing to said avian an isolated nucleic acid molecule which encodes or is complementary to a nucleic acid molecule which encodes said cytokine or, alternatively, a vector comprising a gene construct capable of expressing said cytokine in vivo or in ovo, for example a live recombinant viral vector, live recombinant bacterial vector.

Wherein the cytokine of the invention is administered via the introduction of an isolated nucleic acid molecule encoding said cytokine, such as a DNA or RNA molecule, or a vector comprising a gene construct capable of expressing said cytokine, the nucleic acid molecule or gene construct must be transcribed and translated to produce the biologically-active cytokine molecule following its administration to an appropriate avian subject.

Advances in slow-release technology and the development of live non-pathogenic bacteria and viruses as delivery vectors for these molecules will ensure their cost-effectiveness when administered to poultry, domestic birds or game birds. They may also be used in nucleic acid vaccination. Accordingly, the avian cytokine or vaccine of the present invention may also be delivered by genetic means. For example, recombinant avian ChIFN-γ may be encoded by a gene construct present in a delivery system such as a virus, yeast, bacterium, protozoan, insect, avian or mammalian cell. The expression of such a delivery system in a target animal will enable delivery of the recombinant avian cytokine.

It will be apparent from the disclosure herein that the administered avian IFN-γ polypeptide, with or without additional Type I or Type II molecules, or alternatively, as a fusion polypeptide with another cytokine polypeptide, has application as a natural adjuvants for vaccines, particularly for subunit or synthetic peptide vaccines produced by recombinant DNA technology.

The term "adjuvant" as used herein shall be taken to mean a substance that, when administered to an animal in combination with a second substance or antigen, enhances the production of immunointeractive molecules, such as antibodies, which recognise the second substance or antigen molecule. An adjuvant may be used therapeutically to produce antibodies against small amounts of antigen or to prolong the period of antibody production or to increase the amount of antibody produced.

According to this embodiment, an adjuvant is preferably administered in combination with a pharmaceutically-acceptable carrier, excipient or diluent.

According to this embodiment, there is contemplated a gene construct comprising:

(i) a first nucleotide sequence encoding an avian IFN-γ or interferon-like molecule or a fusion cytokine molecule between said IFN-γ and a second cytokine, placed operably under the control of a first promoter sequence;

(ii) a second nucleotide sequence defining an antigen against which immunisation is required, placed operably under the control of a second promoter sequence; and (iii) a delivery vehicle comprising genetic sequences which facilitate replication of said gene construct in a delivery cell such as a bacterial, yeast, insect, a protozoan animal or a mammalian cell.

According to this embodiment, the delivery cell would not in normal use be harmful or pathogenic to the target animal. Conveniently, attenuated delivery cells are employed. Particularly useful delivery vectors are attenuated viruses and recombinant viral and bacterial vectors.

For example, an attenuated viral vector is used. The genetic sequence encoding an avian cytokine such as ChIFN-γ or a derivative thereof is cloned into the viral sequence and the recombinant virus used to infect target animals. The recombinant virus causes infection and replicates in the animal cells resulting in production of the recombinant cytokine. The infecting recombinant virus may subsequently be eliminated after production of an immuno-modulatingly effective amount of the recombinant cytokine. A similar protocol is adopted with live bacterial carriers. Alternatively, a non-replicating, non-infectious viral vector may be used. A non-replicating viral vector provides a means of introducing a genetic sequence which is transiently capable of expression of the desired cytokine because the non-replicating viral vector is not capable of cell-to-cell transmission.

The cytokine molecule of the present invention, in particular ChIFN-γ, is also useful as a growth-enhancing or growth-promoting agent and/or maturation-promoting agent when administered to an avian species such as a species of poultry, domestic bird or a game bird. The present invention is particularly useful as a growth performance enhancer and, as the inventors have demonstrated in the Examples described herein, administration of ChIFN-γ to immature birds leads to significant increases in weight, addition to the prevention of weight loss usually associated with various disease states.

A second aspect of the invention provides a method of enhancing the growth performance of a healthy or diseased bird, said method comprising administering to said bird an avian IFN-γ cytokine polypeptide for a time and under conditions sufficient to induce weight gain in said healthy or diseased bird or to prevent weight loss in said diseased bird, wherein said avian IFN-γ cytokine polypeptide is selected from the group consisting of:

(a) a polypeptide having the amino acid sequence set forth in any one of SEQ ID NOs: 2–7;

(b) a polypeptide having the amino acid sequence set forth as the mature protein region of any one of SEQ ID NOs: 2–7;

(c) a polypeptide encoded by DNA present in an avian DNA library, wherein said DNA hybridizes under conditions of at least moderate stringency with a probe having a sequence complementary to at least 50 contiguous nucleotides of SEQ ID NO: 1;

(d) a polypeptide encoded by a nucleotide sequence that is degenerate with a DNA molecule according to (c); and (e) a polypeptide comprising at least 10 contiguous amino acids of any one of SEQ ID NOs: 2–7, wherein said polypeptide has immunomodulatory activity.

As used according to this aspect of the invention, the term "healthy bird" or similar shall be taken to mean a bird that exhibits no symptoms of a disease associated with or known to cause weight loss or loss of appetite in birds. The term "healthy bird" clearly encompasses a bird that is susceptible to a disease associated with or known to cause weight loss or loss of appetite in birds, notwithstanding that it may not exhibit any symptoms associated therewith at the time of administration of said cytokine polypeptide.

As used according to this aspect of the invention, a "diseased bird" means a bird that has a disease, such as, for example, a disease associated with weight loss or loss of appetite in birds, or is infected with a causative agent thereof. Accordingly, a "diseased bird" includes a bird that exhibits one or more symptoms of a disease associated with, or known to cause, weight loss or loss of appetite in birds, including actual weight loss and/or loss of appetite. A "diseased bird" may also include a bird that exhibits no actual symptoms however has been diagnosed as carrying a causative agent of a disease associated with weight loss or loss of appetite in birds.

By enhancing growth performance is meant to increase the weight of an avian species or to prevent weight losses therein normally detectable during or following pathogenic infection of an avian species.

This aspect of the invention is particularly related to the treatment of weight loss in birds that are susceptible to coccidiosis or suffer from coccidiosis or are infected with Eimeria spp., in particular *E. acervulina,* or are susceptible to infection with Eimeria spp., in particular *E. acervulina.*

In performing this aspect of the invention, it will be apparent to those skilled in the art that the methods discussed supra for the expression of avian IFN-γ polypeptides in various cell type, including the use of gene constructs and expression vector systems therefor, and subsequent administration of avian IFN-γ polypeptides to birds, are equally applicable to this purpose.

Recombinant avian IFN-γ polypeptides, or a homologue, analogue or derivative thereof, in particular ChIFN-γ, are useful in the production of immunological interactive molecules such as antibodies or functional derivatives thereof including Fabs or SCABS (single-chain antibodies), antibodies conjugated to an enzyme, radioactive or fluorescent tag, the only requirement being that said immunologically interactive molecules are able to bind to an avian IFN-γ or interferon-like molecule described herein.

Accordingly, a further aspect of the present invention provides an antibody which binds to an avian IFN-γ molecule. In an even more preferred embodiment, said immunologically-interactive molecule binds to a IFN-γ or interferon-like molecule or a homologue, analogue or derivative thereof comprising at least 10 amino acid residues, preferably at least 20 amino acid residues and more preferably at least 50 amino acid residues contained within the amino acid sequence set forth in SEQ ID NO: 2 or having at least 40% similarity thereto. The antibody molecule may be monoclonal or polyclonal and may be used for developing enzyme-immunosorbent assays for the rapid diagnosis of infectious diseases of poultry, domestic birds or game birds.

Immunoassays are useful in detecting the presence of a cytokine in a target animal, particularly birds, in particular to detect an immune response in which the level of said avian cytokine is altered, for example following infection with a pathogen. As a consequence, such an immunoassay is of particular use in determining whether a bird has been exposed to a pathogen or is currently infected with a pathogen or has a prolonged low-grade pathogenic infection. Immunoassays are also useful for the quantization of cytokines, in particular for screening genetic stocks for high cytokine-expressing lines with improved disease-resistance to a pathogen. The invention described herein extends to all such uses of immunointeractive molecules and diagnostic assays which require said immunoassays for their performance.

A wide range of immunoassay techniques may be such as those described in U.S. Pat. Nos. 4,016,043, 4,424,279 and 4,018,653. These methods may be employed for detecting a IFN-γ or interferon-like molecule related to ChIFN-γ. By way of example only, an antibody raised against ChIFN-γ is immobilised onto a solid substrate to form a first complex and a biological sample from an animal to be tested for the presence of cytokine brought into contact with the bound molecule. After a suitable period of incubation, for a period of time sufficient to allow formation of an antibody-cytokine secondary complex, a second ChIFN-γ antibody labelled with a reporter molecule capable of producing a detectable signal is then added and incubated, allowing sufficient time for the formation of a tertiary complex of antibody-cytokine-labelled antibody. Any unreacted material is washed away, and the presence of the tertiary complex is determined by observation of a signal produced by the reporter molecule. The results may either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent. The antibodies used above may be monoclonal or polyclonal.

The solid substrate is typically glass or a polymer, the most commonly used polymers being cellulose, polyacrylamide, nylon, polystyrene, polyvinyl chloride or polypropylene. The solid supports may be in the form of tubes, beads, discs or micro plates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay are either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

The antibodies of the invention are also useful in combination with the inventive avian cytokine polypeptide, as an adjuvant for enhancing the immunogenicity of an antigen following administration to a bird. Without being bound by any theory or mode of action, the antibody:cytokine combination will have a longer half-life and/or slower release than compositions comprising the cytokine polypeptide in an unmodified form.

Preferably, the antibody used in such a composition will be one that binds specifically to the cytokine polypeptide, and, more preferably, without significantly reducing its activity. Without being bound by any theory or mode of action, antibodies that do not inhibit cytokine activity are useful for protecting the cytokine from proteloysis. However, the use of antibodies that also inhibit activity of the cytokine may be desirable in cases where delayed action of the cytokine is required, wherein the activity of said cytokine is restored following release of the cytokine from the antibody complex, such as, for example, following degradation of the antibody.

Similarly, the present invention also provides, as exemplified herein, avian IFN-γ polypeptides that have been modified chemically to extend the half-life or longevity of said polypeptide, such as, for example, by the addition of one or more protecting groups. Those skilled in the art will be aware of protecting groups other than the PEG substituents exemplified herein, that may be used to modify the avian IFN-γ polypeptides of the invention. The present invention clearly extends to the use of chemical modificaitons other than those exemplified herein to extend the half-life or longevity of said polypeptide.

Further aspects of the invention provide compositions for enhancing the growth performance of a bird, and/or for modulating the immune response(s) of a bird, said compositions comprising a carrier, excipient or diluent in combination with an amount of a recombinant avian IFN-γ cytokine polypeptide selected from the group consisting of:

(a) a polypeptide having the amino acid sequence set forth in any one of SEQ ID NOs: 2–7;

(b) a polypeptide having the amino acid sequence set forth as the mature protein region of any one of SEQ ID NOs: 2–7;

(c) a polypeptide encoded by DNA present in an avian DNA library, wherein said DNA hybridizes under conditions of at least moderate stringency with a probe having a sequence complementary to at least 50 contiguous nucleotides of SEQ ID NO: 1;

(d) a polypeptide encoded by a nucleotide sequence that is degenerate with a DNA molecule according to (c); and (e) a polypeptide comprising at least 10 contiguous amino acids of any one of SEQ ID NOs: 2–7, wherein said polypeptide has immunomodulatory activity.

The present invention clearly extends to a veterinary pharmaceutical composition for use in poultry, domestic bird or game birds such as to enhance the immune system or accelerate its maturation or improve its immunocompetence or to facilitate immunomodulation in said birds, said composition comprising a recombinant avian IFN-γ or a fusion molecule between a IFN-γ and a second cytokine, in combination with an antigen or pathogenic organism against which it is desired to obtain immuno-protection, and optionally one or more carriers and/or diluents acceptable for veterinary use.

In accordance with the present invention, an avian cytokine such as a IFN-γ or interferon-like molecule, in particular ChIFN-γ, is used in vaccines to enhance the immunogenicity of antigens, particularly in subunit vaccines, leading to increased antibody titre in individual birds, increased protection of birds that are immunised against a specific antigen (i.e. enhanced flock immunity) and/or increased persistence of protective antibodies in immunised birds. A further advantage provided by the present invention is a reduction in the quantity of specific antigen required to effectively immunise animals, thereby leading to reduced production costs.

Preferably, the above-mentioned compositions comprise a recombinant avian cytokine and are injected into the bird in ovo or post-hatching, or administered via aerosol or ingestion.

In an alternative embodiment, the present invention clearly contemplates the use of genetic vaccines and pharmaceutical compositions, wherein nucleic acid encoding the proteinaceous components is administered to the bird for expression therein. Wherein the composition comprises genetic material such as nucleic acid, it is administered as part of a viral vector, bacterial vector or as a nucleic acid molecule.

The bird to be treated and the cytokine in the composition might be "homologous" in the sense that both are of the same species, or may be "heterologous" where the avian cytokine is effective in another bird species than the species from which it has been derived. The compositions may also contain other active molecules such as antibiotics or antigen molecules. Combinations of cytokine molecules with antigen molecules may increase the efficacy of the compositions.

The present invention extends to a veterinary pharmaceutical composition comprising an immunomodulatingly effective amount of a fusion molecule between an avian IFN-γ and a second cytokine or genetic sequences capable of expressing same and one or more carriers and/or diluents acceptable for veterinary use.

The active ingredient(s) of the pharmaceutical composition is/are contemplated to exhibit excellent activity in stimulating, enhancing or otherwise facilitating an immune response in an animal species and in particular a poultry, domestic bird or game bird when administered in an amount which depends on the particular case. The variation depends, for example, on the cytokine and, in some cases, the antigen involved in stimulating the immune response. For example, from about 0.5 μg to about 20 mg of a particular cytokine which may be combined with other cytokines, per kilogram of body weight per day may be required. Dosage regimen may be adjusted to provide the optimum therapeutic response. For example, several divided doses may be administered in one or more of daily, weekly or monthly or in other suitable time intervals or the dose may be proportionally reduced as indicated by the exigencies of the situation. The active compound may be administered by injection either in ovo or post-hatching or by oral ingestion in any convenient manner or may be administered via a genetic sequence such as in a viral or bacterial vector.

The active compounds may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for parenteral administration include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, antibiotics, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example.

Sterile injectable solutions are prepared by incorporating the active compounds in the required amount in the appropriate solvent with various of the other ingredients enumerated above, as required, followed by filter sterilisation. Generally, dispersions are prepared by incorporating the various sterilised active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Carriers and/or diluents suitable for veterinary use include any and all solvents, dispersion media, aqueous solutions, coatings, antibacterial and antifungal agents, isotonic and absorption delaying agents, and the like. The use of such media and agents for pharmaceutically active substances is well known in the art. Except insofar as any conventional media or agent is incompatible with the active ingredient, use thereof in the composition is contemplated. Supplementary active ingredients can also be incorporated into the compositions. The latter is particularly contemplated as far as the present invention extends to multivalent vaccines or multi-component cytokine molecules.

The pharmaceutical veterinary compositions of the present invention may comprise in addition to an avian IFN-γ or interferon-like molecule or a fusion molecule comprising same, one or more other active compounds such as antigens and/or immune stimulating compounds.

The cytokine may also be delivered by a live delivery system such as using a bacterial expression system to express the cytokine protein in bacteria which can be incorporated into gut flora. Alternatively, a viral expression system can be employed or incorporated into a recombinant vaccine. In this regard, one form of viral expression is the administration of a live vector generally by spray, feed or water where an infecting effective amount of the live vector (e.g. virus or bacterium) is provided to the animal. Another form of viral expression system is a non-replicating virus vector which is capable of infecting a cell but not replicating therein. The non-replicating viral vector provides a means of introducing genetic material for transient expression into a cytokine. The mode of administering such a vector is the same as a live viral vector.

The present invention is further described by reference to the following non-limiting Examples.

EXAMPLE 1

Reagents and Starting Materials

Specific Pathogen Free (SPF) Hybrid White Leghorn (HWL) chickens produced by the CSIRO SPF poultry unit (Maribymong, Victoria) were raised in flexible plastic isolators and fed fumigated feed and acidified water.

All cell lines and vectors referred to herein were publicly available or fully-described in U.S. Ser. No. 08/765,381 or Ser. No. 09/272,032, which are incorporated herein by way of reference.

EXAMPLE 2

Cloning of Avian IF-γ-Encoding Genes

The cloning of a cDNA encoding IFN-γ of chickens is described in detail in U.S. Ser. No. 08/765,381 which is incorporated herein by way of reference.

The ChIFN-γ nucleotide and derived amino acid sequences are shown in SEQ ID NOs: 1 and 2, respectively. The ChIFN-γ cDNA codes for a predicted protein of 164 amino acids with a signal peptide of 19 amino acids. The predicted mature protein is 145 amino acids in length with a molecular mass of 16.8 kD. Two potential N-glycosylation sites are predicted, the most likely site is at position 42–44, with the other at position 23–25. Like other IFN-γ proteins, ChIFN-γ contains few cysteine residues. The mature protein has only two cysteine residues which are located at the C-terminus.

Other avian IFN-γ-encoding genes have been cloned from ducks (Schultz et al., Scripps Research Institute 10550 North Torrey Pines Road, La Jolla, Calif. 92037, United States of America, personal communications), and from Guinea fowl, pheasant, quail and turkey (Kaiser et al., 1998), all of which have been isolated using SEQ ID NO: 1 as a hybridization probe, in standard nucleic acid hybridization reactions or by 5'-RACE and 3'-RACE (i.e. Rapid Amplification of cDNA Ends, a variation of PCR).

The IFN-γ activity of the duck IFN-γ-encoding clone has been confirmed by measuring the anti-viral protection conferred in both chicken and duck cells and, as expected for authentic duck IFN-γ, recombinantly-expressed duck IFN-γ has significant anti-viral activity in both duck cells and chicken cells, however approximately 32-fold the anti-viral activity in duck cells that is observed in chicken cells.

The identity of the turkey IFN-γ-encoding sequence has also been confirmed by measuring the anti-viral activity of the recombinantly-produced polypeptide product of this sequence in chicken cells.

The amino acid sequences of the derived duck, Guinea fowl, pheasant, quail and turkey IFN-γ polypeptides are set forth herein as SEQ ID NOs: 3–7.

There are no gaps in the alignment between chicken and duck IFN-γ polypeptides and only 54 amino acid differences, 26 of which are conservative amino acid substitutions (eg. Ser-Thr, Ser-Ala, Arg-Lys, Lys-Glu, Asn-His, Asp-Glu, Glu-Gln, Ile-Leu, Ile-Val, Leu-Met, Met-Val, Phe-Tyr, Val-Ile, Val-Leu). Based on the proportion of identical residues in the alignment between chicken and duck IFN-γ polypeptides, there is 67% amino acid sequence identity between these sequences over the entire length of chicken IFN-γ (i.e. amino acids −19 to 145 of SEQ ID NO: 2) and 64% identity in the mature secreted protein region (i.e. amino acids 1 to 145 of SEQ ID NO: 2).

There are also no gaps in the alignments of chicken IFN-γ and other avian polypeptides Accordingly, these sequences are all highly-conserved, having 87.8% (guinea fowl) to 97.6% (turkey and pheasant) amino acid sequence identity with chicken IFN-γ over their entire length (i.e. amino acids corresponding to positions −19 to 145 of SEQ ID NO: 2) and 86.2% (guinea fowl) to 97.2% (turkey and pheasant) identity in the mature secreted protein region (i.e. amino acids corresponding to positions 1 to 145 of SEQ ID NO: 2).

In contrast, there is only very low homology between avian IFN-γ and a number of mammalian IFN-γ and avian IFN-α polypeptides, and there is no functional cross-protection from virus-mediated lysis of fibroblasts conferred by avian versus non-avian IFN-γ polypeptides, as is described in U.S. Ser. No. 08/765,381.

EXAMPLE 3

Methods
1. Chicken Embryonic Fibroblast (CEF) Interferon Assay

IFN was measured by the ability to protect CEF and turkey embryonic fibroblasts (TEF) from virus-mediated as described by Prowse and Pallister (1989), Lowenthal et al (1995 a) and Lowenthal et al (1995 b). Secondary fibroblasts were seeded into 96 well microtitre plates ($5\times10^4$/well) and grown in the presence of 10% FBS at 41° C. After 24 hr the culture medium was replaced with 100 μl of serum-free growth medium and 2-fold serial dilutions of test supernatants were made in duplicate. Control wells contained cells cultured in medium alone or cultured in the presence of a reference supernatant of known IFN activity. After overnight incubation at 37° C., the culture medium was replaced with 100 μl of medium containing Semliki Forest virus or Vesicular Stomatitis virus ($10^3$ tissue culture infective dose/ml) and the cells were incubated at 37° C. After 24 hr, cell viability was measured by uptake of neutral red dye and absorbance at 540 nm was quantitated using an ELISA reader.

2. Nitrite Assay

Production of nitric oxide by HD11 chicken macrophages (Beug et al, 1979) was quantitated by accumulation of nitrite in the culture medium (Sung et al, 1991) and was used as a measure of IFN-γ activity. Two-fold serial dilutions of test supernatants were made in duplicate wells of 96 well plates in a volume of 100 μl of growth medium containing 5% FBS. HD11 cells were added to each well ($10^5$ in 100 μl) and the plates were incubated at 37° C. After 24 hr, 50 μl of culture supernatant was added to 100 μl of Griess reagent (1.1 mixture of 1% sulfanilamide and 0.1% naphthylethylene diamine in 2.5% $H_3PO_4$) and absorbance was read at 540 nm. The level of nitrite was determined using sodium nitrite as a standard.

3. ELISA for ChIFN-γ

Monoclonal antibodies for use in ELISA are described in detail below (see Example 6). Microtitre plates were coated with Mab 80.9 (1 ug/ml in carbonate buffer, pH 8, 100 ul/well) overnight at 4° C. All subsequent incubation steps were carried out at room temperature (RT) for 1 h with three washes (PBS with 0.5% tween) between each step. The plates were blocked (1% Powerblock, 100 ul/well) and serial dilutions of ChIFN-γ or control preparations (100 ul/well) were added. Biotinylated Mab or polyclonal rabbit antisera (1:1000 dilution) was added to each well as the detection antibody, followed by the addition of HRP-labelled streptavidin (Amersham) or HRP-goat anti-rabbit Ig (Zymed). ChIFN-γ binding was revealed by the addition of tetramethyl benzidine (TMB) peroxidase substrate followed by quenching with 0.5 M $H_2SO_4$. Plates were read on an ELISA reader at 450 nm. The ELISA titre is defined as the reciprocal of the dilution giving an OD reading above the cut off value which is calculated as [mean background±3SEM].

Figure 1A:
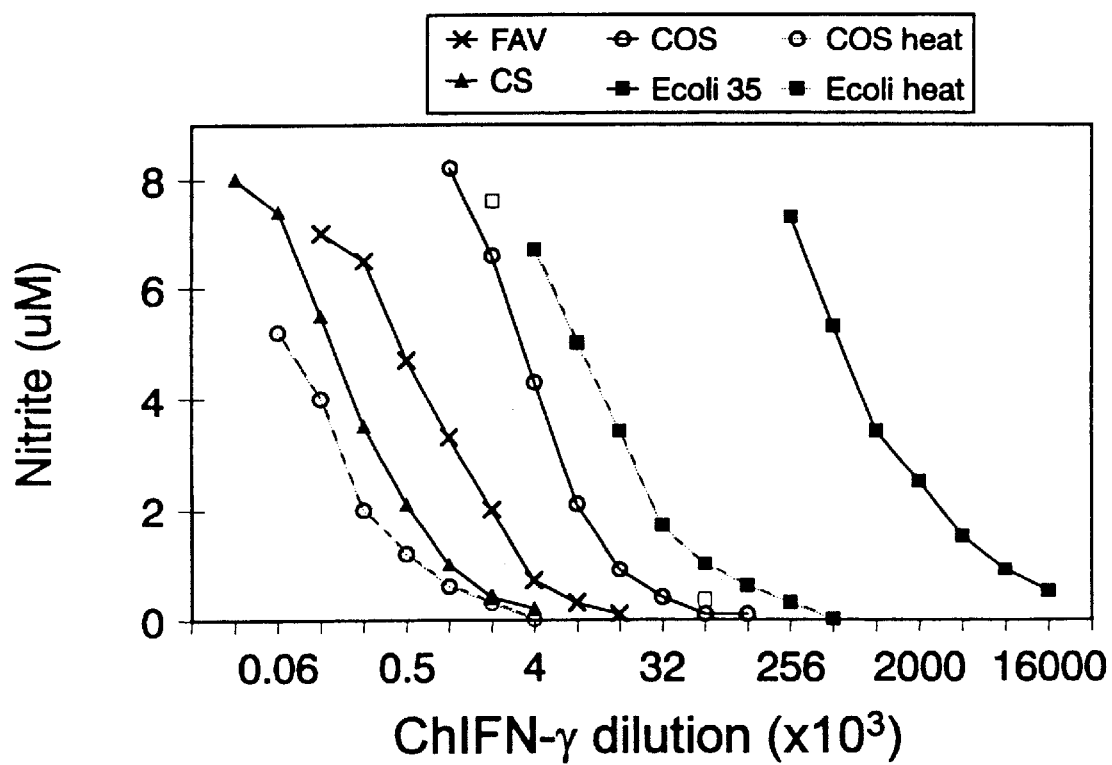
FIG. 1A shows the biological activity of various ChIFN-γ preparations as measured by the HD11 nitrite release assay.
Figure 1B:
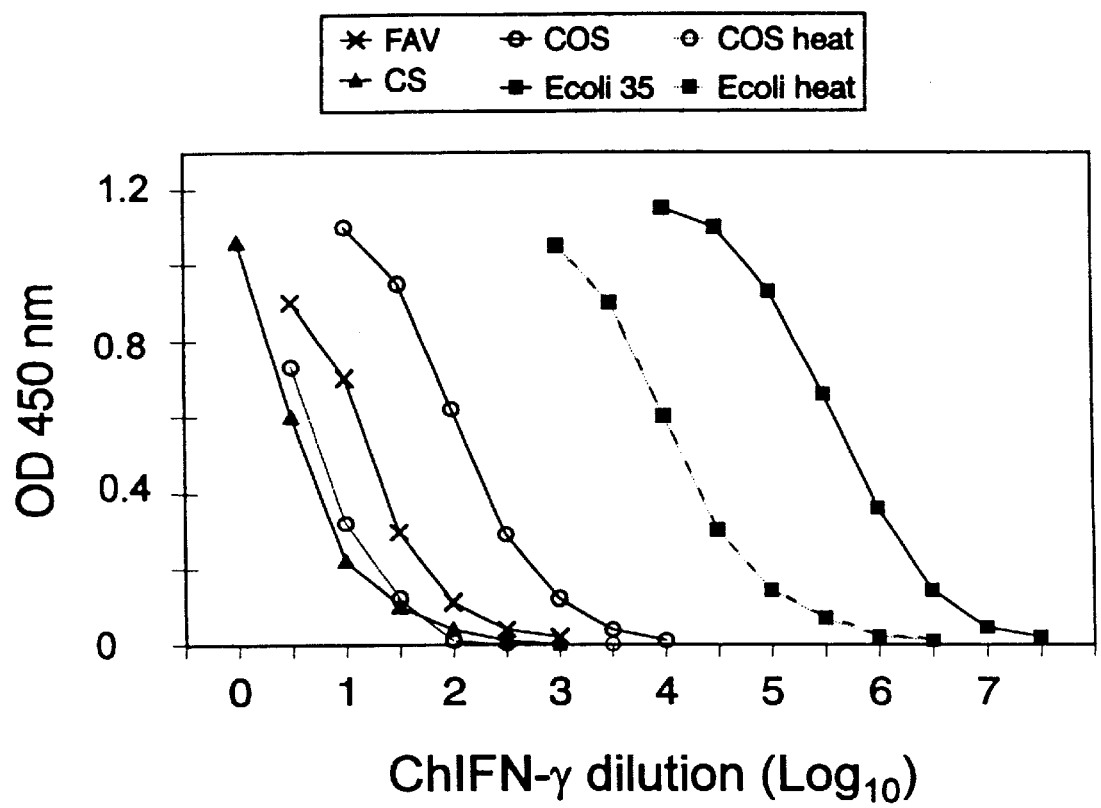
FIG. 1B shows the quantitation of various ChIFN-γ preparations as measured by ELISA.
Figure 2:
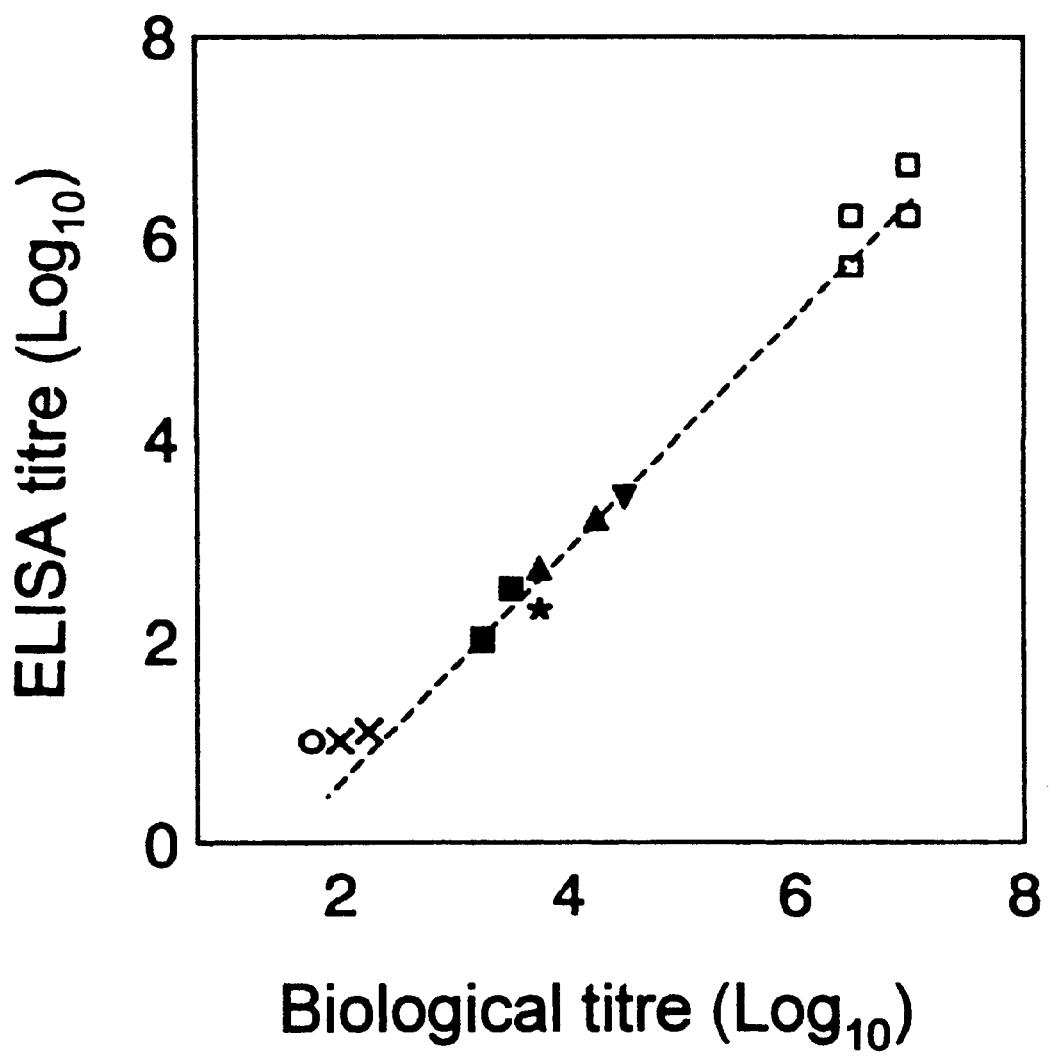
FIG. 2 is a graphical representation showing the correlation between biological function of ChIFN-γ, as determined by nitrite release bioassay, and immunological cross-reactivity as determined by sandwich ELISA using Mab 80.9. Sources of rChIFN-γ were as follows: COS cells (▲); Concanavalin A-activated chicken T cells (CS cells; X); E. coli native protein(□); CK cells infected with recombinant FAV expressing ChIFN-γ (■); heat-denatured COS-cell derived ChIFN-γ (o); E. coli protein at room temperature (▼); and heat-denatured E. coli derived ChIFN-γ (★).

To confirm that this ELISA provides an accurate representation of avian IFN-γ activity, native and denatured (i.e. heat-denatured) samples of recombinant chicken IFN-γ produced by various expression systems as described herein were quantitated in the HD11 nitrite assay and the results compared to the results derived from ELISA (FIGS. 1A and 1B). As shown in FIG. 2, there is a strong correlation between the level of biological activity (biological titre as determined using nitrite release assay) and detectability by ELISA (ELISA titre). Additionally, heating samples of ChIFN-γ or exposure to low pH conditions (not shown) results in a concomitant decrease in both biological and ELISA titres. These data indicate that the ELISA described herein detects only biologically active molecules (i.e. homodimers) of ChIFN-γ and not inactive molecules, and, as a consequence, is useful for reliably quantitating the biological activity of ChIFN-γ with a sensitivity comparable to that of the conventional HD11 bioassay.

Figure 3A:
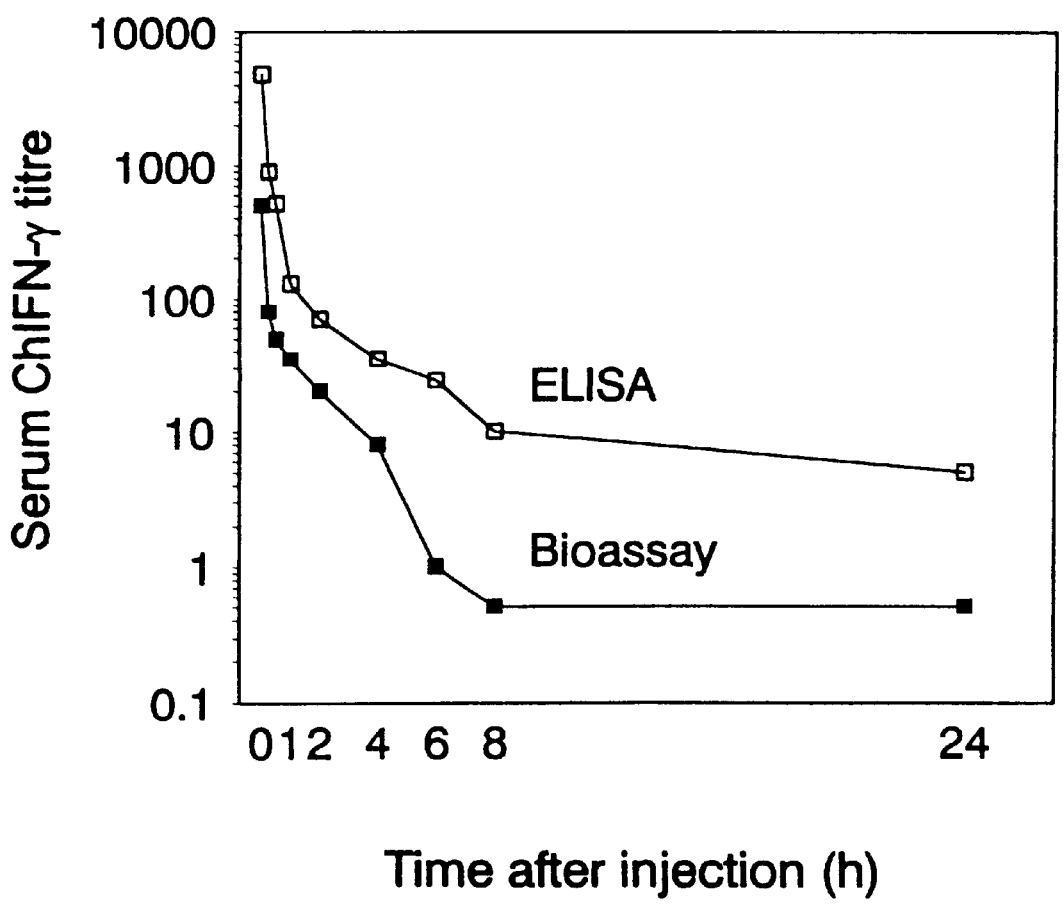
FIG. 3 shows graphical representations of the half lives of ChIFN-γ as determined by bioassay and ELISA, following intravenous injection (FIG. 3A) or intraperitoneal injection (FIG. 3B) of 5000 Units of E coli-derived ChIFN-γ. The x-axis indicates the time after injection in both figures. The y-axis indicates serum titre of ChIFN-γ.
Figure 3B:
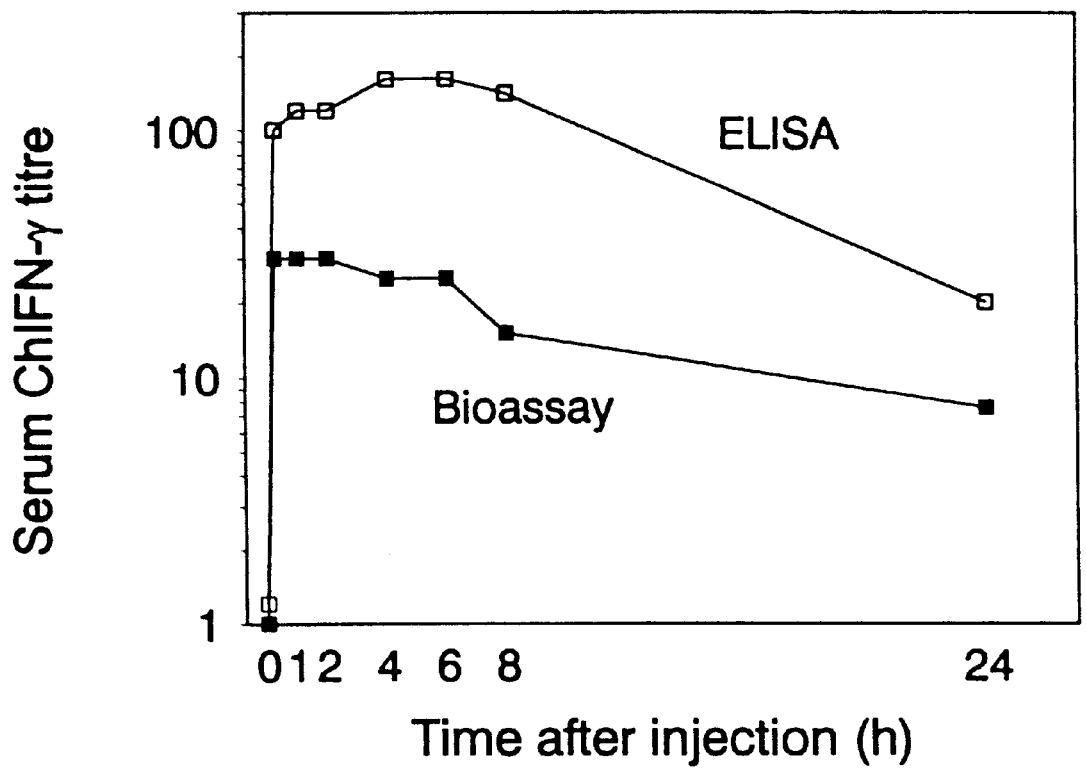

Data presented in FIG. 3 show the improved sensitivity of ELISA compared to the nitrite release bioassay, in detecting ChIFN-γ in sera following intravenous (i.e. i/v; FIG. 3A) and intraperitoneal (i.e. i/p; FIG. 3B) injection. ELISA was consistently 3–10 fold more sensitive than the bioassay in detecting serum levels of IFN-γ. In particular, the bioassay has difficulty in measuring ChIFN-γ in the presence of chicken serum, particularly at low levels of the cytokine. Addition of high concentrations of serum (greater than 10% v/v) to HD11 cells results in lowered responsiveness to ChIFN-γ, a problem not encountered in the ELISA.

4. Injection of ChiFN-γ in ovo

This procedure describes the technique to be used for manual egg injection of test materials. Alternatively, eggs can be injected using an automated Inovoject® system.

a) Egg Candling

Eggs are maintained under warm room conditions during candling and transfer, if possible. It is best not to keep eggs out of the incubator/hatcher for more than three hours. Eggs are candled by illumination of egg contents with an egg candler in a darkened room. Eggs that have a clear demarcation between air cell and embryo, a rosy color, obvious veins or that show movement, are retained. Eggs that are clear (infertile), nonviable, cracked, excessively dirty, have green discoloration, or are upside down (no air cell in blunt end of egg), are discarded.

b) Needle/Punch and Egg Sanitizer Preparation

An 18 gauge 1.5 inch needle is inserted through a rubber stopper so that the needle cannot penetrate to a depth beyond 2 mm. A 0.5% chlorine solution is prepared by 1:10 (v/v) dilution of 5.25% sodium hypochlorite (commercial bleach).

c) Administration of ChIFN-γ in ovo

The blunt end of the egg is swabbed with a 0.5% chlorine solution (1:10 dilution of commercial bleach [5.25% sodium hypochlorite]). All eggs are manually punched with an 18 gauge needle attached to a rubber stopper. The ChIFN-γ preparation is delivered 2.5 cm through the blunt end of the egg, below the air cell membrane, using a 20 gauge×1" needle attached to a 1 ml tuberculin syringe. The injection needle is sterilized between deliveries to each egg by punching into 1.5" thick sponge soaked in 0.5% chlorine solution. New needles and syringes are used each time the sample is withdrawn from the original container. Dose volume for in ovo administration is usually 100 ul (with 1 ml syringe). The injection hole is then covered using nail varnish and the injected eggs incubated in a hatcher. Administration by in ovo injection as described herein does not reduce hatch ability of eggs.

EXAMPLE 4

Expression of Recombinant Avian IFN-γ Polypeptides

1. Expression of Recombinant ChIFN-γ in *E. coli*.

The mature coding region of ChIFN-γ (SEQ ID NO: 1) was cloned into the pQE expression vector (QIAexpress Type IV construct, Qiagen, Calif.) according to manufacturers instructions. The sequences of the oligonucleotides used to amplify the mature region of the gene using PCR are as follows:

5' ACTAGATCTCATACTGCAAGTCTAAAT 3':    SEQ ID NO:9

5' ACTAAGCTTTTAGCAATTGCATCTCCTCTG 3': SEQ ID NO:10

All procedures used for the expression of recombinant ChIFN-γ using Ni columns and purification was according to manufacturers instructions.

Figure 4A:
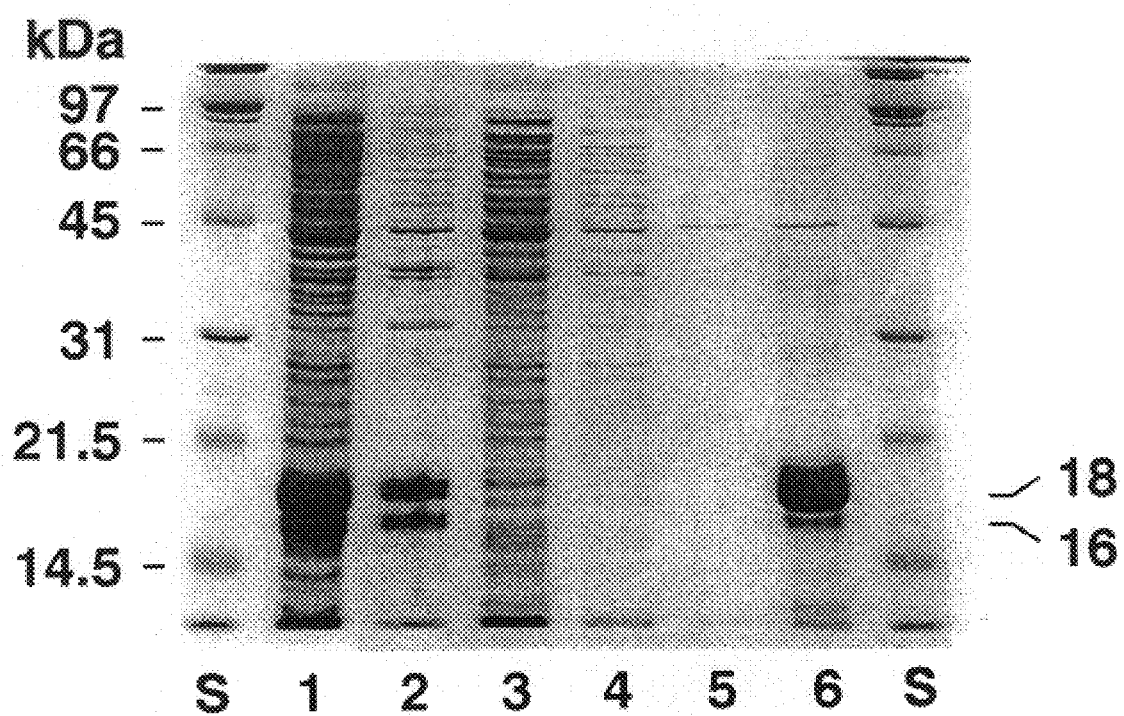
In FIG. 4A: S, standard Mr markers; Lane 1, crude sonication supernatant; Lane 2, soluble fraction; Lane 3, Ni column flow through; Lane 4 and 5, column washes; Lane 6, eluted recombinant ChIFN-γ.
Figure 4B:
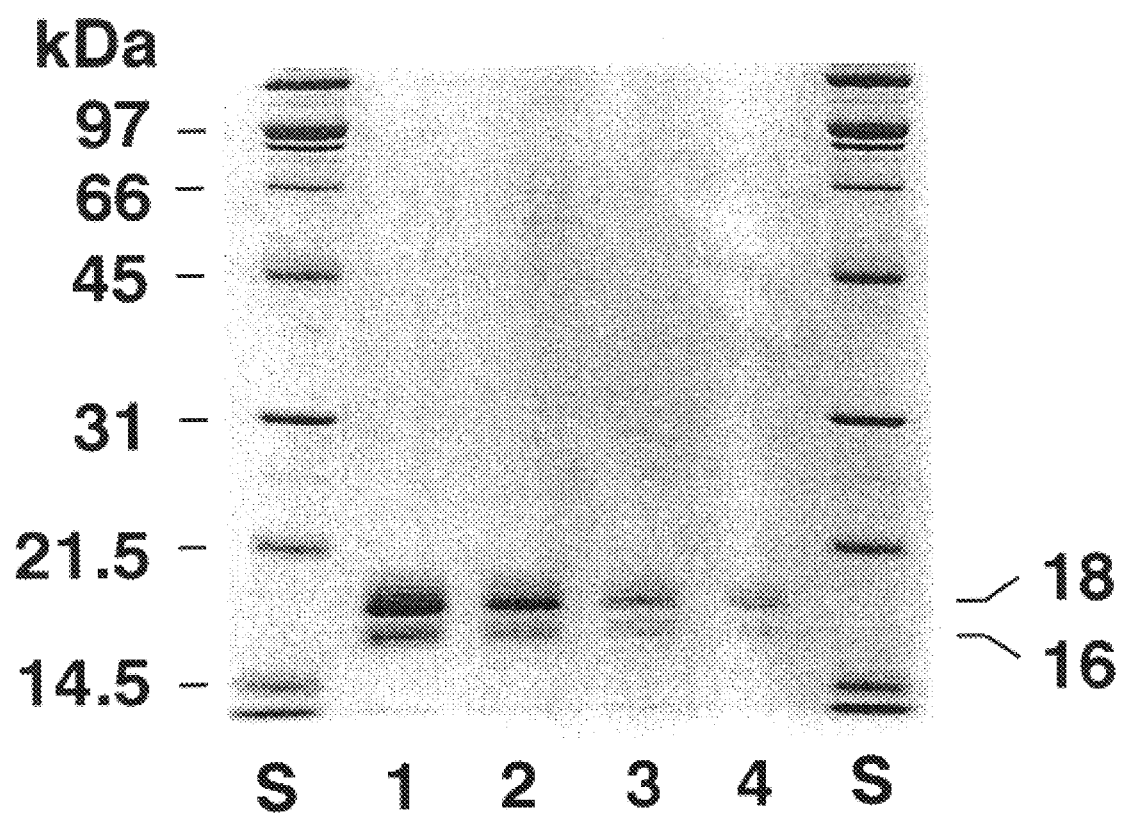
In FIG. 4B: S, standard Mr markers; Lanes 1–4, purified recombinant ChIFN-γ serially diluted 2-fold (lane 1), 4-fold (lane 2), 8-fold (lane 3) or 16-fold (lane 4).

Recombinant ChIFN-γ (r ChIFN-γ) bearing a poly-HIS tag was expressed in *E. coli* using the pQE expression system and purified using a Ni affinity column (FIG. 4A). Two forms of recombinant ChiFN-γ were produced (Mr 16 and 18 kDa).

Figure 5:
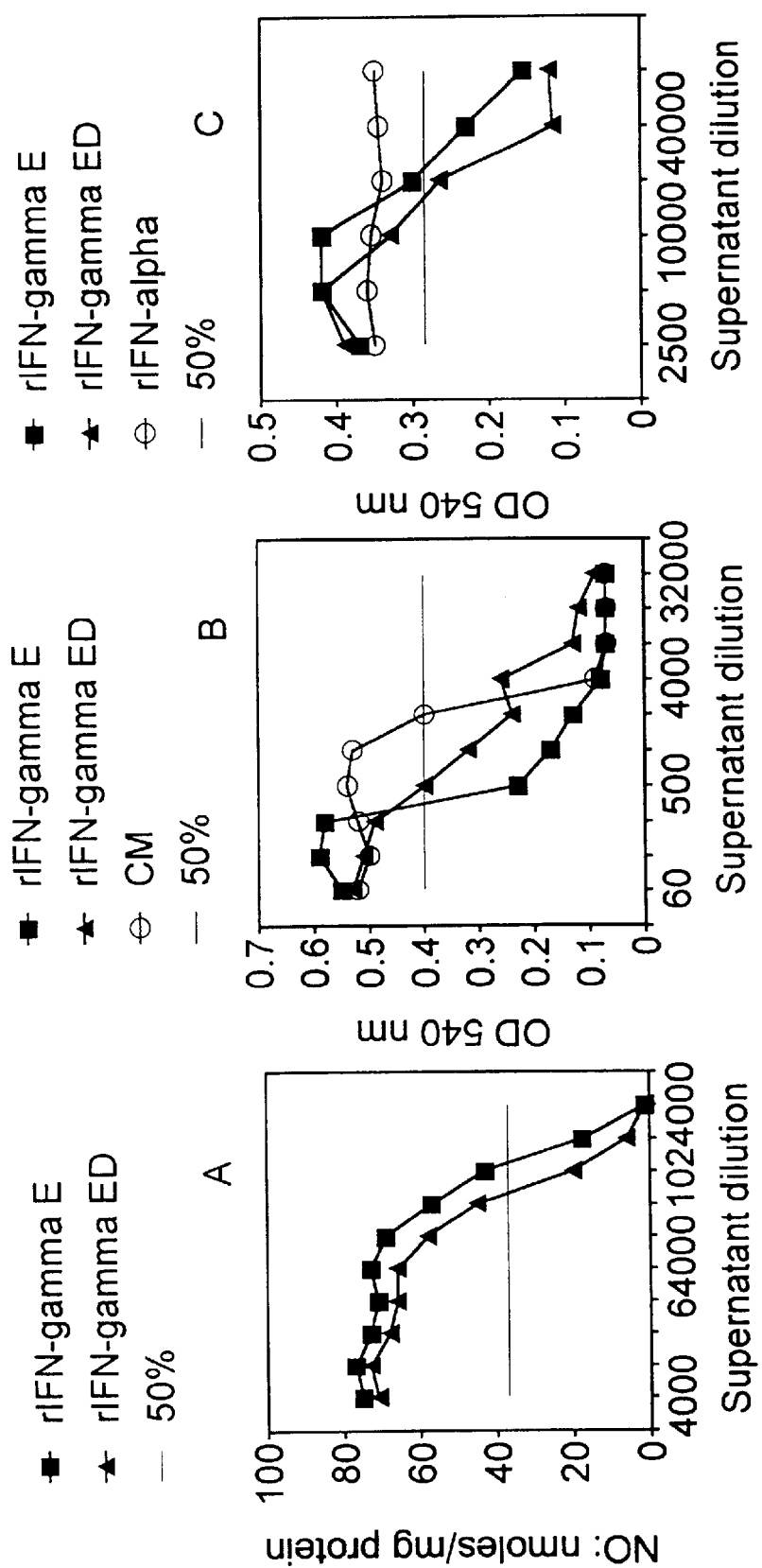
FIG. 5 provides graphical representations showing biological activity of recombinant ChIFN-γ on chicken (CEF) and turkey cells (TEF).

The activity of recombinant ChIFN-γ was determined using the CEF assay, nitrite assay, or a Turkey Embryonic Fibroblast (TEF) protection assay. Recombinant ChIFN-γ was active in the nitrite assay (FIG. 5A), in the CEF assay (FIG. 5B) and in a Turkey TEF protection assay (FIG. 5C).

Figure 6:
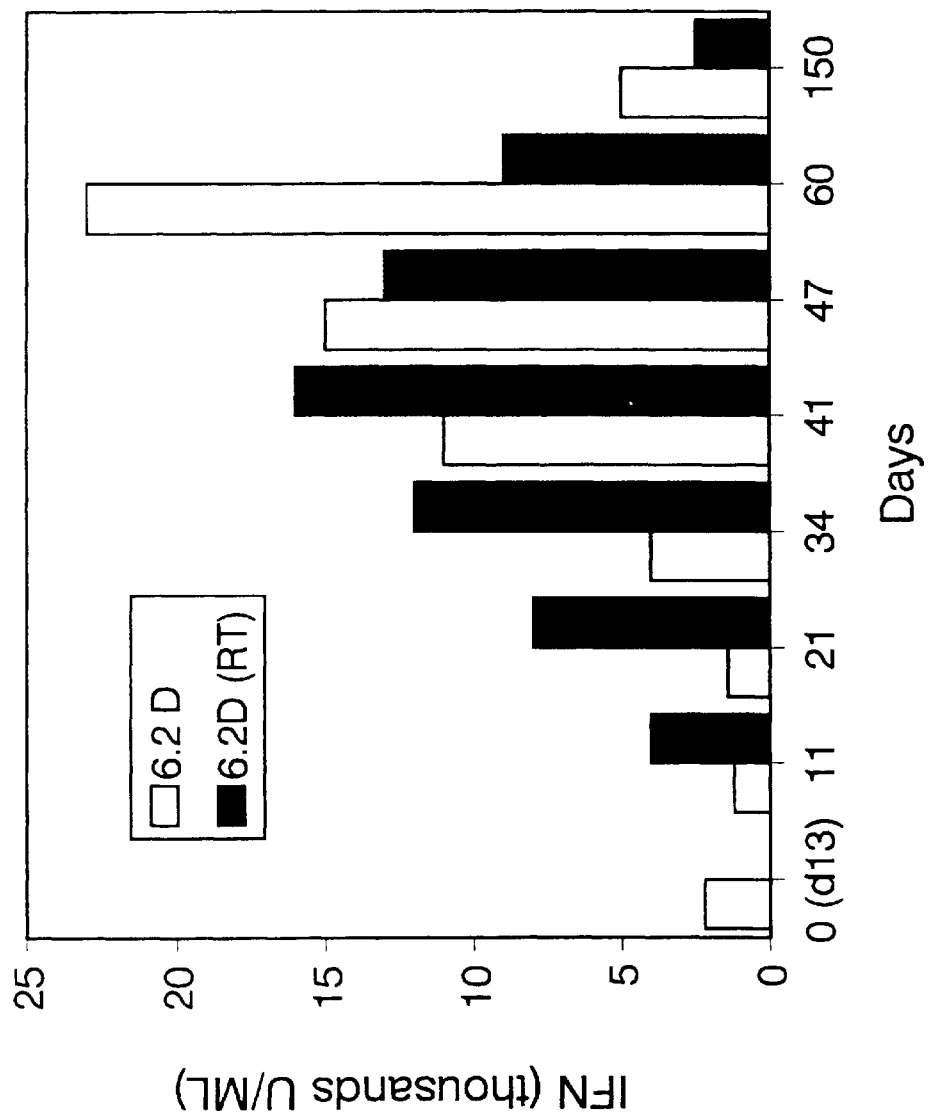
FIG. 6 is a graphical representation showing stability of recombinant ChIFN-γ following storage at room temperature [6.2D (RT)] or at 40° C. (6.2D) as measured using the nitrite assay.

The stability of recombinant ChIFN-γ was also monitored over various time intervals. Data provided in FIG. 6 indicate that recombinant ChIFN-γ is stable when stored at 4° C. or at room temperature. The inventors have shown further that recombinant ChIFN-γ can be stored for several months.

2. Expression of Recombinant ChIFN-γ in COS Cells.

Figure 7:
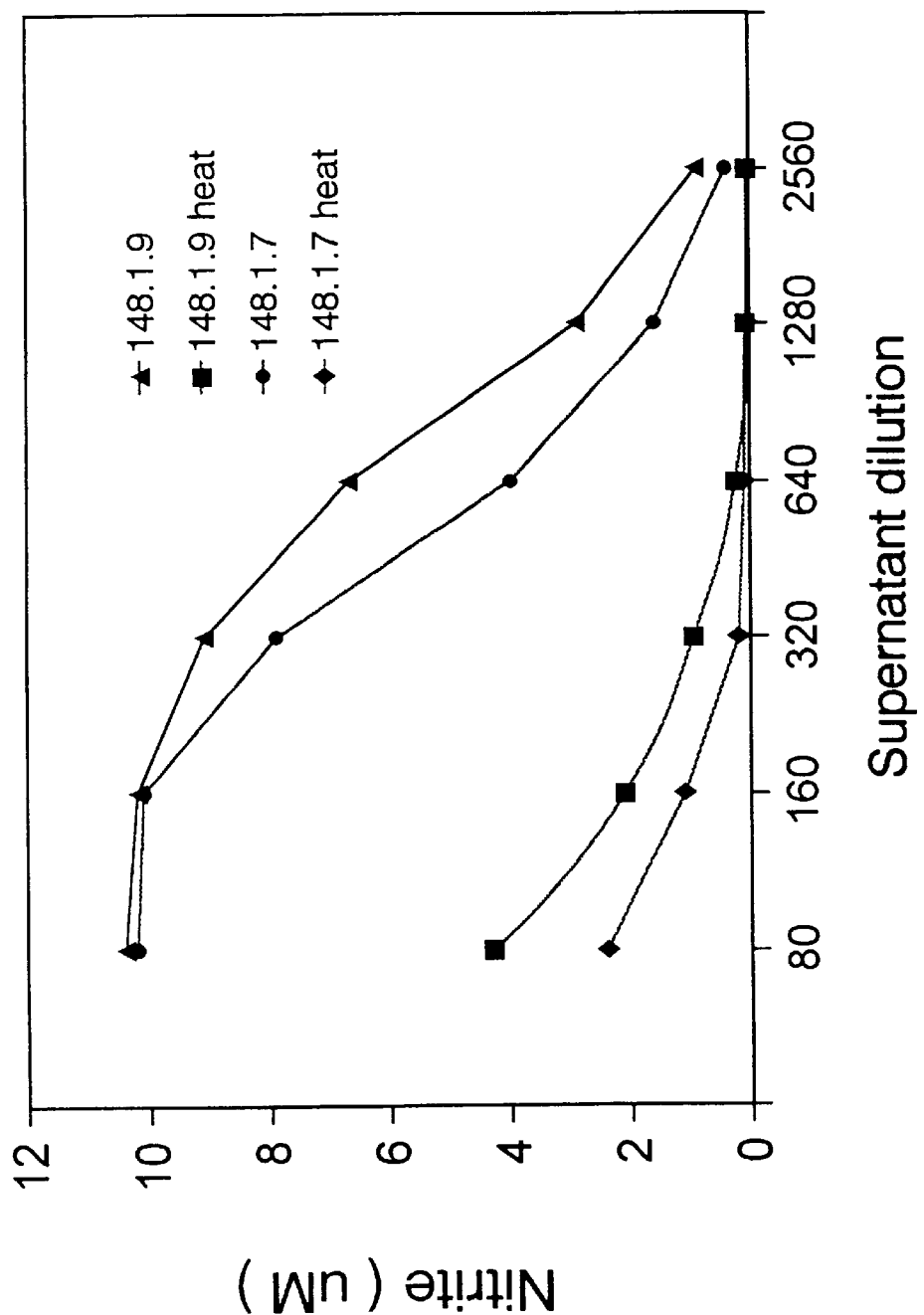
FIG. 7 is a graphical representation showing biological activity of supernatants from COS cells transfected with single clones of the CC8.1h library that were known to express ChIFN-γ (U.S. Ser. No. 08/765,381). Plasmid pools containing 100 clones were sequentially subpooled into pools of 10 and then into single clones. Clones 148.1.7 and 148.1.9 were transfected into COS cells and ChIFN-γ activity was measured in the supernatant 3 days later. The effect of heating the recombinant ChIFN-γ to 60° C. for 30 min is shown.
Figure 8:
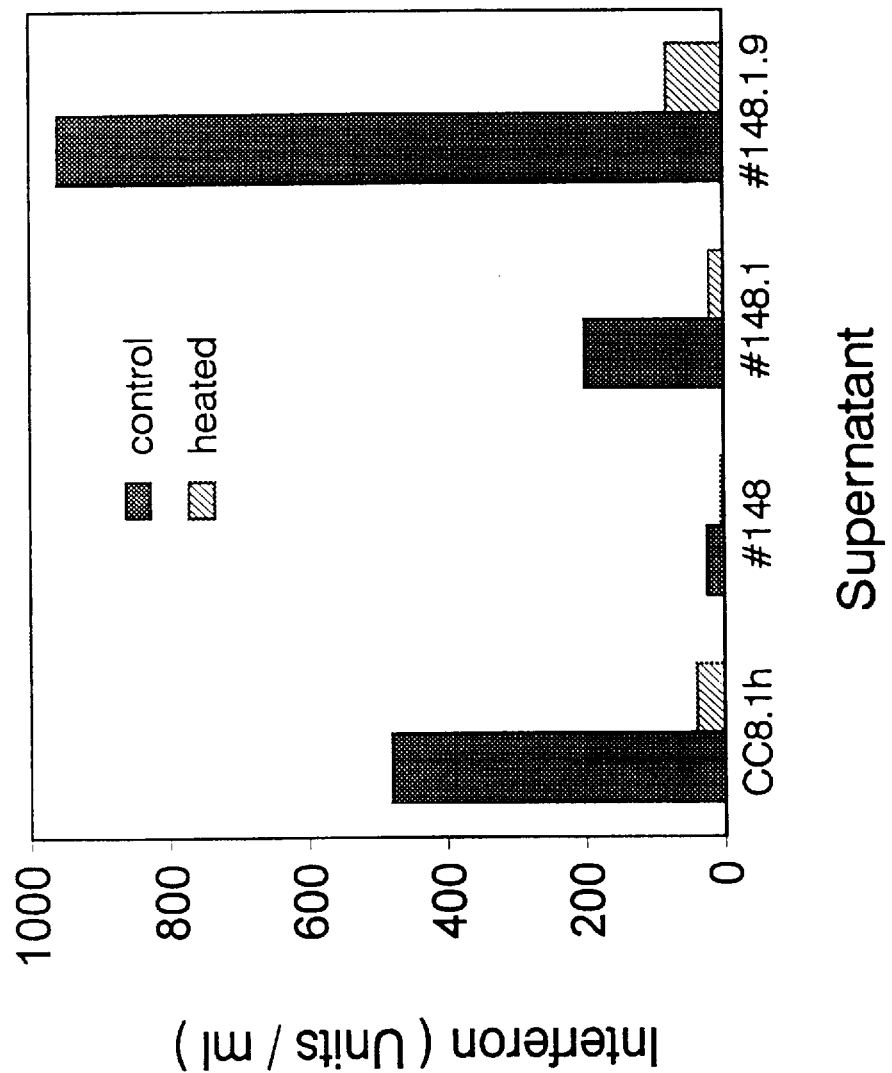
FIG. 8 is a graphical representation showing production of recombinant ChIFN-γ. COS cells were transfected with #148 (pool of 100 clones), #148.1 (a pool of 10 clones derived from 148) and #148.1.9 (a single clone derived from 148.1). Supernatant from CC8.1h (AGAL Accession No. N94/46035) is used as a positive control. The effect of heating the supernatants to 60° C. for 30 min is also shown.

Avian IFN-γ-encoding cDNA clones were transfected into COS cells and supernatants were shown to exhibit IFN-γ bioactivity 2 to 4 days after transfection, in both the CEF and nitrite assays. In particular, supernatants of COS cells transfected with the chicken IFN-γ plasmid produced very high levels of recombinant ChIFN-γ (FIGS. 7 and 8). Recombinant ChIFN-γ showed the same degree of heat sensitivity and pH 2 sensitivity as that shown by native ChIFN-γ (data not shown).

3. Expression of Recombinant ChIFN-γ in CK Cells.

a) Construction of a Recombinant FAV Vector Expressing Avian IFN-γ

(i) FAV Vector Sequences:

The 17.1 kb nucleotide sequence of the right-hand end of FAV serotype 8 (FAV8) is set forth in SEQ ID NO: 8. The right-hand end was identified by cloning and sequencing three restriction fragments of FAV8 (CFA40) as follows:

1. Plasmid pJJ383, deposited under the provisions of The Budapest Treaty on the International Recognition of the Deposit of Microorganisms for the Purposes of Patent Procedure (hereinafter "The Budapest Treaty") with Australian Government Analytical Laboratories at 1 Suakin Street, Pymble, New South Wales 2073, Australia on Nov. 11, 1999, and assigned AGAL Accession No. NM99/08170. Plasmid pJJ383 contains a NheI fragment of 8.5 kb in length derived from the FAV8 right-hand end, cloned into the vector pGEM-11f(+/−);

2. Plasmid pJJ698, deposited under the provisions of The Budapest Treaty with Australian Government Analytical Laboratories at 1 Suakin Street, Pymble, New South Wales 2073, Australia on Nov. 11, 1999, and assigned AGAL Accession No. NM99/08172. Plasmid pJJ698 contains a Bg/II fragment of 7.5 kb in length derived from the FAV8 right-hand end, cloned into the vector pUC18; and 3. Plasmid pJJ407, deposited under the provisions of The Budapest Treaty with Australian Government Analytical Laboratories at 1 Suakin Street, Pymble, New South Wales 2073, Australia on Nov. 11, 1999, and assigned AGAL Accession No. NM99/08173. Plasmid pJJ407 contains a Bg/II fragment of 1.7 kb in length derived from the FAV8 right-hand end, cloned into the vector pUC18.

(ii) Avian IFN-γ Expression Cassette

An expression cassette was produced to facilitate the expression of IFN-γ from recombinant FAV, said cassette comprising the FAV MLP sequence (Johnson et al, 1988) operably connected to the ChIFN-γ coding region, and placed upstream of the SV40 transcription termination signal, by cloning the cassette into the NotI site of the bacterial plasmid vector pUC18. The plasmid produced that contains this expression cassette was designated plasmid pJJ427.

Plasmid pJJ427 was deposited under the provisions of The Budapest Treaty with Australian Government Analytical Laboratories at 1 Suakin Street, Pymble, New South Wales 2073, Australia on Nov. 11, 1999 and assigned AGAL Accession No. NM99/08169.

The NotI site in plasmid pJJ427 is also useful for subsequent insertion of the expression cassette into FAV8 sequences, either directly, or following end-filling and blunt-end ligation.

(iii) Recombinant FAV Containing the Avian IFN-γ Expression Cassette

There are unique XbaI, SnaBI and SmaI sites in the NheI fragment of plasmid pJJ383 to facilitate the insertion of foreign DNA.

In one vector construct, the 1.3 kb region between the unique SnaBI and SmaI sites of plasmid pJJ383 was deleted and replaced by the IFN-γ expression cassette of plasmid pJJ427. The resultant plasmid, designated pJJ464, was deposited under the provisions of The Budapest Treaty with Australian Government Analytical Laboratories at 1 Suakin Street, Pymble, New South Wales 2073, Australia on Nov. 11, 1999 and assigned AGAL Accession No. NM99/08171.

In a second vector construct, the 2.2 kb XbaI-SnaBI fragment of pJJ383 was deleted and replaced by the expression cassette of plasmid pJJ427. The resultant plasmid, designated pJJ677, was deposited under the provisions of The Budapest Treaty with Australian Government Analytical Laboratories at 1 Suakin Street, Pymble, New South Wales 2073, Australia on Nov. 11, 1999, and assigned AGAL Accession No. NM99108174.

In a third vector construct, the 50 bp region between two SpeI sites of pJJ383 was deleted and replaced by the expression cassette of plasmid pJJ427, leaving most of the FAV8 vector sequence intact. The resultant plasmid, designated pJJ486, was deposited under the provisions of The Budapest Treaty with Australian Government Analytical Laboratories at 1 Suakin Street, Pymble, New South Wales 2073, Australia on Nov. 11, 1999 and assigned AGAL Accession No. NM99/08175.

The deposits referred to herein will be maintained under the terms of The Budapest Treaty and are provided merely as a convenience to those skilled in the art and not as an admission that any one or more of said deposits is required under 35 U.S.C. §112.

To produce recombinant FAV expressing ChIFN-γ, each of the three plasmids pJJ464, pJJ677, and pJJ486, containing the expressible ChIFN-γ encoding region, was transfected with SpeI-digested FAV viral genomic DNA. The recombinant FAVs were plaque-purified and characterized by Southern blotting and PCR using standard procedures.

b) Transcriptional Mapping

To confirm expression of IFN-γ from recombinant FAV, mRNA was isolated from infected cell cultures at 6 hr and 20 hr post-infection with either wild-type FAV8 or recombinant FAV8 comprising the IFN-γ coding region produced as described supra. The mRNA was purified using Qiagen Direct mRNA Maxi kit, and transferred directly to nylon membranes using the Ambion Northern Max-Gly kit. Fragments derived from the right-hand end of the FAV8 genome were probed, using the protein-coding region of the ChIFN-γ cDNA, radiolabelled with $^{32}P$, as a probe. This analysis confirmed the presence of ChIFN-γ transcripts in the recombinant FAV only.

Figure 9:
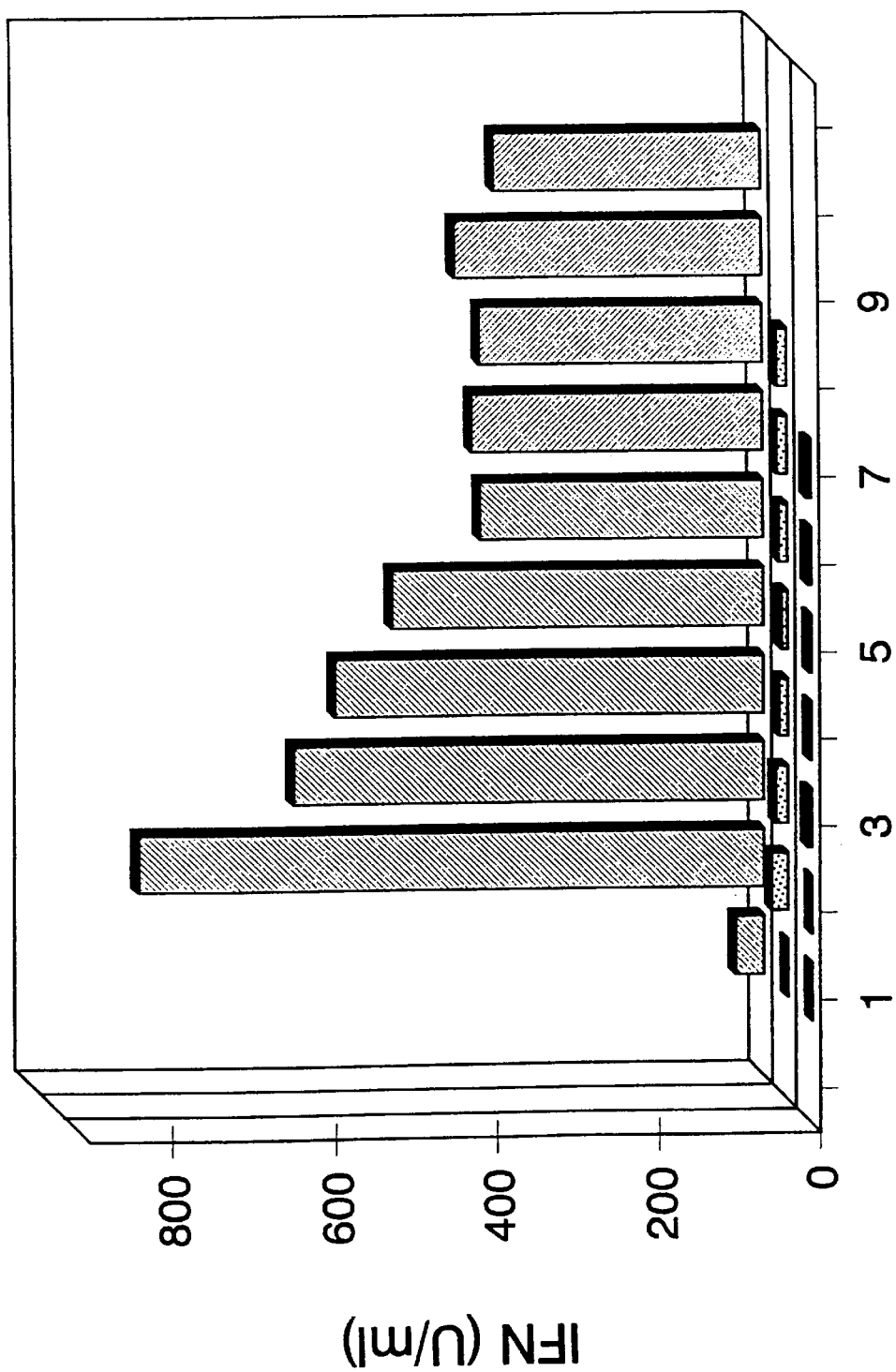
FIG. 9 is a graphical representation of the ChIFN-γ activity of CK cells infected with recombinant FAV8 expressing ChIFN-γ derived from plasmid pJJ464, at 1 day, 3 days, 5 days, 7 days and 9 days post-infection (hatched bars). The activity of a negative control sample infected with FAV8 lacking the ChIFN-γ-encoding expression cassette is also indicated (■). The activity of CK cells infected with recombinant FAV8 expressing ChIFN-γ derived from plasmid pJJ464, following incubation with an antibody that blocks ChIFN-γ activity is also indicated (stippled bars). Data indicate that effective amounts of authentic avian IFN-γ are produced by CK cells infected with rFAV expressing IFN-γ under the control of the FAV MLP.

To confirm these results, mRNA was also used as a substrate for RT-PCR employing the Promega Reverse Transcription System, employing primers that were specific to ChIFN-γ. This analysis confirmed the presence of ChIFN-γ transcripts in recombinant FAV-ChIFNγ-infected cells at 20 hr post-infection. The amplified product was also confirmed as ChIFN-γ, by subsequent sequence determination.

c) Biological Activity of Recombinant ChIFN-γ Produced in Recombinant FAV-ChIFNγ-Infected Cells The biological activity of rChIFN-γ was determined using the nitrite release assay. Two-fold serial dilutions of test supernatants from cultures of CK cells that were infected with either wild-type FAV8 or with r FAV-ChIFNγ were made in duplicate wells of 96 well plates. HD11 cells were added to each well and the plates incubated at 37° C. After 24 hr, 50 μl of culture supernatant was added to 100 μl of Griess Reagent and the absorbance determined at 540 nm. Duplicate cultures were also incubated in the presence or absence of 1% (v/V) rabbit anti-ChIFN-γ serum, which blocks ChIFN-γ, but not Type I molecules. The results (FIG. 9) indicate that rChIFN-γ is expressed and is biologically-active.

EXAMPLE 5

Recombinant Avian IFN-γ Induces Cell Surface Expression of Cla

1. Expression of Class II Molecules

Data presented in U.S. Ser. No. 08/765,381 show that HD11 cells cultured in the presence of recombinant or native ChIFN-γ for 48 hr showed enhanced levels of cell surface expression of Class II molecules relative to cells grown in media alone (88% and 52% increase in expression, respectively). In contrast, the presence of another macrophage stimulator, LPS, induced only an 8% increase in Class II expression.

Here we demonstrate that avian IFN-γ induces expression of the MHC Class II antigen Cla on the surface of HD11 cells. HD11 cells were cultured for 24 hr in the presence of various preparations of recombinant ChIFN-γ and then analyzed for the cell surface expression of MHC class II antigen (Cla). Approximately 15% of HD11 cells constitutively express Cla, however this proportion increases in a dose-dependent manner, following exposure to recombinant ChIFN-γ (FIG. 10). Recombinant ChIFN-γ expressed by insect cells using a baculovirus expression system, and recombinant IFN-γ produced by COS cells and E. coli as described supra, showed similar dose-response curves (FIG. 10A), and, for both types of protein preparation, the dose response for nitrite secretion is equivalent to that seen for induction of Cla expression (FIGS. 10B–10C).

EXAMPLE 6

Antibodies that Bind to Avian IFN-γ Polypeptides a) Polyclonal Antibodies

Rabbit antisera was raised against purified recombinant ChIFN-γ protein. Rabbits were immunized three times with 400 μg of protein and sera was collected 10 days after the final injection. Specific reactivity of the sera to ChIFN-γ was confirmed using immune and pre-immune sera in Western blots and in assays measuring the ability to inhibit the release of nitrite by HD11 cells. Sera from each rabbit recognised recombinant ChIFN-γ as shown by Western blots (FIG. 11). Some of these rabbit sera also inhibit the biological function of native and recombinant ChIFN-γ in vitro but did not block the function of ChIFN-β (FIG. 12).

Furthermore, protein G-purified rabbit anti-recombinant ChIFN-γ antibodies also inhibit the function of recombinant ChIFN-γ (FIG. 13).

b) Monoclonal Antibodies (Mabs)

Balb/C mice were immunized three times with E. coli-derived, poly-HIS tagged ChIFN-γ, as follows:

(i) ChIFN-γ (10 ug) in Freund's complete adjuvant, was injected sub-cutaneously (s/c);

(ii) ChIFN-γ (10 ug) in Freund's incomplete adjuvant, was injected intra-peritoneally (i/p); and (ii) ChIFN-γ (10 ug) in PBS, was injected intra-peritoneally (i/p).

Hybridomas were generated by fusion of spleen cells and SP2/0 myeloma cells. Mabs were screened for their ability to bind to ChIFN-γ-coated ELISA plates. Antibody isotypes were determined using anti-IgG1, anti-G2a, anti-G2b, anti-M, anti-κ and anti-λ antibodies. Mab Ig was purified by protein G chromatography. The specific reactivities of various monoclonal antibodies to ChIFN-γ was determined using ELISA (Table 1). The ability of the various monoclonal antibodies to block recombinant ChIFN-γ-induced nitrite secretion by HD11 macrophages was also determined (Table 1). Data presented in Table 1 further indicates the relative utilities of the various monoclonal antibodies to detect ChIFN-γ in western blots.

TABLE 1

Characteristics of anti-ChIFN-γ Mabs

| Mab Clone | Isotype | ELISA Titre (IgG) | Inhibition in HD11 bioassay COS cells | Inhibition in HD11 bioassay CK cells | Inhibition in HD11 bioassay E. coli | Relative activity in western blots |
|---|---|---|---|---|---|---|
| 13.1 | M | $2 \times 10^5$ | —[a] | — | — | ++++ |
| 80.9 | G1 | $5 \times 10^5$ | 200[b] | 200 | 1200 | — |
| 149.1 | G1 | $1 \times 10^5$ | >[c] | >[c] | >[c] | — |
| 68.6 | G1 | $1 \times 10^5$ | >[c] | >[c] | >[c] | — |
| 85.6 | G2a | $2 \times 10^5$ | 50 | 100 | 160 | — |
| 31.9 | G2a | $1 \times 10^6$ | — | — | — | +++ |

TABLE 1-continued

Characteristics of anti-ChIFN-γ Mabs

| Mab Clone | Isotype | ELISA Titre (IgG) | Inhibition in HD11 bioassay COS cells | Inhibition in HD11 bioassay CK cells | Inhibition in HD11 bioassay E. coli | Relative activity in western blots |
|---|---|---|---|---|---|---|
| 9.1 | G2b | $1 \times 10^5$ | — | — | — | +++ |
| 19.1 | G2b | $6 \times 10^4$ | — | — | — | + |

[a]Non inhibitory at 100 ug/ml
[b]Concentration of Ig (ng/ml) giving 50% inhibition of activity in HD11 assay.
[c]>20 ug/ml Ig required to give 50% inhibition of activity in HD11 assay.

FIG. 14A shows that the Mabs listed in Table 1 differ in their ability to block the biological activity of COS-derived ChIFN-γ in the HD11 nitrite assay. As shown in FIG. 14B, Mab 80.9 was able to block the activity of recombinant ChIFN-γ derived from either *E. coli* or COS cells, as well as native ChIFN-γ derived from Con A-activated chicken T cells, and from chicken fibroblasts (CK cells) infected with recombinant FAV expressing ChIFN-γ produced as described supra. The dose inhibition curves for Mab 80.9 were indistinguishable for all sources of ChIFN-γ.

Competition ELISAs were performed, in which biotinylated Mab 80.9 was mixed with various concentrations of different anti-ChIFN-γ Mabs prior to their addition to plates coated with ChIFN-γ, to determine the affinity of Mab 80.9 for ChIFN-γ relative to other Mabs. As shown in FIG. 14C, some Mabs were able to block the binding of Mab 80.9 to recombinant ChIFN-γ, whereas other were not, indicating that they seem to recognise different determinants of the ChIFN-γ molecule.

EXAMPLE 7

Enhancement of Immune Reactions Using Recombinant Avian IFN-γ Polypeptides

1. ChIFN-γ as an Adjuvant

Four Groups (n=10) of 3-week old SPF chickens were injected intramuscularly (i/m) with either 0.2 or 0.02 ml of sheep red blood cells (SRBC). One group at each dose was also injected intra-peritoneally with 500 Units of recombinant ChIFN-γ the day before and on the day of immunization. Birds were bled weekly and haemaglutination titres of the sera were determined.

Chickens were injected with SRBC (with or without recombinant ChIFN-γ) and weekly haemaglutination (HA) titres of the sera were determined. Results are shown in FIG. 15. Treatment with recombinant ChIFN-γ resulted in a higher mean HA titre, a prolonged antibody response and increased the effectiveness of the low dose of antigen. This indicates that recombinant ChIFN-γ is an effective adjuvant.

2. Effect of Recombinant ChIFN-γ on Infection with IBDV in vivo

One group (n=10) of three-week old SPF chickens was injected intraperitoneally with 500 Units of recombinant ChIFN-γ on 2 consecutive days and another group of control birds (n=10) was injected with diluent alone. Both groups of birds were infected intra-ocularly with infectious Bursal Disease Virus (IBDV). Birds were sacrificed 7 days later and the bursa and whole body weights were determined.

Birds injected with recombinant ChIFN-γ displayed an enhanced ratio of body:bursa weight from a mean of 1.36 to 1.51 (FIG. 16), indicating that recombinant ChIFN-γ was effective in reducing virus growth in vivo.

The effect of recombinant ChIFN-γ to protect CEFs from infection with IBDV in vitro was also measured. CEFs were prepared as described for the CEF interferon assay and recombinant ChIFN-γ and IBDV were added to the cultures together. Cell survival was measured 3 days later on a scale of 0 to 4, where 0 represents the level of cell survival observed in the presence IBDV and the absence of IFN (<5% cell survival) and 4 represents the level of cell survival observed in the absence of IBDV (>90% cell survival). As shown in FIG. 17, recombinant ChIFN-γ was effective in protecting CEFs from infection with IBDV in vitro.

In conclusion, recombinant ChIFN-γ has been shown to effective in the prevention of infection by IBDV both in vivo and in vitro.

EXAMPLE 8

Growth-Promoting Effects of Avian IFN-γ

1. Enhancement of Growth Performance in Healthy Birds a) Use of Isolated Recombinant ChIFN-γ Protein One group (n=10) of one-day old SPF chickens was injected intraperitoneally with 500 Units of recombinant ChIFN-γ on 2 consecutive days and another group of control birds was injected with diluent alone. Birds were weighed over a 12 day period. Birds injected with recombinant ChIFN-γ displayed enhanced weight gain (FIGS. 18 and 19). The increase in body weight was from 5.8 to 9.0% (Table 2). These data indicate that recombinant ChIFN-γ was effective in enhancing growth performance.

TABLE 2

Effect of recombinant ChIFN-γ on weight gain in broilers.

| Day | Body weight (g)[a] rChIFN-γ[b] | Body weight (g)[a] Control[c] | % Increase |
|---|---|---|---|
| 3 | 154.0 ± 18 | 143.5 ± 24 | 7.3 |
| 4 | 204.9 ± 23 | 188.2 ± 35 | 9.0 |
| 5 | 235.4 ± 26 | 217.0 ± 40 | 8.5 |
| 6 | 262.3 ± 28 | 244.3 ± 47 | 7.4 |
| 7 | 290.1 ± 30 | 269.5 ± 49 | 7.6 |
| 10 | 390.8 ± 39 | 360.1 ± 62 | 8.6 |
| 12 | 475.6 ± 43 | 449.5 ± 75 | 5.8 |

[a]Mean weight of chickens (n = 10) ± standard deviation.
[b]Birds injected i/p with 500 U of recombinant ChIFN-γ on days 0 and 1.
[c]Birds injected intra peritoneal with diluent on days 0 and 1.

b) Use of Recombinant FAV to Deliver rChIFN-γ

Commercial broiler chickens at 1 day, 3 days, 6 days, or 10 days post-hatching, were infected by eye-drop with rFAV-ChIFN-γ produced from plasmid pJJ464, as described supra. Birds were housed in positive pressure isolators and maintained on a constant feed regime. Birds were weighed weekly for a period of 7 weeks. All treated birds receiving rFAV-ChIFN-γ showed increased weight gains which were significantly different from control untreated birds in paired t-tests carried out at 34 days and 42 days post-treatment (Table 3). As shown in Table 3, the most significant weight gains were observed in birds infected at 3 days or later post-hatching with recombinant FAV expressing ChIFN-γ, compared to uninfected birds. Less-significant differences were observed between birds that had been infected at different ages post-hatching. Similar effects are observed using rFAV derived from plasmid pJJ486.

TABLE 3

Significance of weight gains in commercial broilers infected with rFAV expressing ChIFN-γ

| Treatments compared in t-test | p-value (34 days) | p-value (42 days) |
|---|---|---|
| untreated birds vs. birds infected day 1 | <0.001 | >0.05 |
| untreated birds vs. birds infected day 3 | <0.002 | <0.05 |
| untreated birds vs. birds infected day 6 | <0.001 | <0.05 |
| birds infected day 1 vs. birds infected day 3 | >0.2 | >0.2 |
| birds infected day 1 vs. birds infected day 6 | >0.2 | >0.2 |

2. Reduction of Weight Loss in Birds During Infection with *E. acervulina* a) Use of Isolated ChIFN-γ Protein

One group (n=10) of one-day old SPF chickens was injected intraperitoneally with 500 Units of recombinant ChIFN-γ on 2 consecutive days (day 0 and day 1) and another group of control birds was injected with diluent alone. All birds were infected with $5\times10^5$ oocytes on day 1 and then weighed over a 12 day period.

Birds injected with recombinant ChIFN-γ displayed enhanced weight gain (FIGS. 20A and 20B). Infection with coccidiosis normally results in weight loss between day 4 and 6 of infection. Treatment with ChIFN-γ reduced the weight loss (FIG. 20C) and enhanced the rate of weight gain following natural recovery from infection (FIG. 20D). Treatment with ChIFN-γ resulted in a 7.3 to 12.5% increase in weight (Tables 4 and 5; and FIG. 21). This indicates that recombinant ChIFN-γ was effective in reducing the effect of coccidiosis on growth performance.

TABLE 4

Effect of rChlFN-γ on weight gain in commercial broilers following infection with *E. acervulina.*

| | Body weight (g)[a] | | |
|---|---|---|---|
| Day | rChlFN-γ[b] | Control[c] | % Increase |
| 4 | 198.7 ± 26 | 185.1 ± 30 | 7.3 |
| 5 | 195.2 ± 26 | 176.8 ± 29 | 10.2 |
| 6 | 202.2 ± 23 | 185.4 ± 31 | 9.1 |
| 8 | 248.4 ± 35 | 220.9 ± 42 | 12.5 |
| 11 | 353.6 ± 52 | 315.6 ± 56 | 12.0 |

[a]Mean weight of chickens (n = 10) ± standard deviation
[b]Birds injected i/p with 500 U rChlFN-γ on days 0 and 1, and $5\times10^5$ oocysts on day 1.
[c]Birds injected i/p with diluent on days 0 and 1, and $5\times10^5$ oocysts on day 1.

TABLE 5

Effect of rChlFN-y on weight gain in commercial broilers following infection with *E. acervulina.*

| | Body weight (g) | | |
|---|---|---|---|
| Day | rChlFN-γ[b] | Control[c] | Increase (g)[d] |
| 1–4 | 52.0[a] | 52.1 | −0.1 |
| 4–5 | −3.5 | −8.3 | 4.8 |
| 5–6 | 7.0 | 8.6 | −1.6 |
| 6–8 | 46.2 | 35.5 | 10.7 |
| 8–11 | 105.2 | 94.7 | 10.5 |
| 1–11 | 206.9 | 182.6 | 24.3 |

[a]Mean weight gain (n = 10) ± standard deviation between the indicated days
[b]Birds injected i/p with 500 U rChlFN-γ on days 0 and 1 and $5\times10^5$ oocysts day 1.
[c]Birds injected i/peritoneal with diluent on days 0 and 1 and $5\times10^5$ oocysts day 1.
[d]Increase in body weight due to recombinant ChlFN-γ.

b) Use of Recombinant FAV to Deliver rChIFN-γ

Commercial broiler chickens at 1 day or 6 days post-hatching were infected by eye-drop with rFAV-ChIFN-γ produced from plasmid pJJ464, as described supra. At 7 days post-hatch, birds were challenged with 5,000 sporulated oocysts of *E. acervulina.* A control group remained unchallenged. Birds were housed in positive pressure isolators and maintained on a constant feed regime. Birds were weighed daily post-challenge. All treated birds receiving rFAV-ChIFN-γ showed increased weight gains compared to controls that were not treated with ChIFN-γ, and those birds maintained these weight gains under coccidiosis challenge, compared to birds that were not treated with ChIFN-γ. Similar effects are observed using rFAV derived from plasmid pJJ486.

EXAMPLE 9

Pharmacokinetics of ChIFN-γ in vivo

1. Measurement of Serum ChIFN-γ Levels

ChIFN-γ samples were injected into 4 week old birds via i/v, i/p, i/m or s/c routes. Blood sample were taken by wing bleeds at various times and serum was tested in ELISA or bioassay.

2. Clearance of Wild-Type rChIFN-γ

ChIFN-γ derived from *E. coli* (FIG. 4) was injected either intra-venously (i/v), sub-cutaneously (s/c) or intra-peritoneally (i/p). Blood samples were taken over time and serum ChIFN-γ levels were measured by ELISA as described supra.

Data are presented in FIG. 22. Following i/v injection, the level of ChIFN-γ reached peak serum levels within 1–3 minutes, and thereafter declined rapidly with about 90% clearance within 30 min. The initial $t_{1/2}$ for ChIFN-γ was approximately 10 min, a value similar to that reported in several studies on mammalian IFN-γ. The remaining ChIFN-γ was cleared at a slower rate and persisted in the circulation over several hours. After 24 h about 0.3–1.0% of the initial levels was still detectable. Following s/c and i/p injection (FIG. 22), or i/m injection (data not shown), ChIFN-γ appeared more slowly in the serum, reaching peak levels by 1–7 hr post-injection. These routes of injection resulted in lower maximum serum levels compared to i/v injection, however serum levels of ChIFN-γ were sustained for longer periods (FIGS. 3 and 22).

2. Clearance of Modified rChIFN-γ

In an attempt to improve the half-life of avian IFN-γ administered to birds, *E coli*-produced ChIFN-γ was modified using two different forms of methoxypolyethylene glycol (PEG) as described by Kita et al. (1990), namely p-nitrophenyl-PEG (NC-PEG) and cyanic chloride-PEG (CC-PEG). Briefly, ChIFN-γ was dialyzed against 10 mM sodium phosphate (pH 8.4) and reacted with various molar excesses of NC-PEG or CC-PEG for 24 hr at room temperature followed by the addition of amino caproic acid. Successful coupling of PEG was confirmed by increased molecular weight of ChIFN-γ, as measured by SDS page electrophoresis.

Treatment of ChIFN-γ by CC-PEG at 5- to 50-fold molar excesses resulted in the coupling of two PEG molecules per molecule of ChIFN-γ (data not shown). Modification of ChIFN-γ by CC-PEG did not reduce its biological activity as measured by the HD11 bioassay (FIG. 23) or ELISA (FIG. 24) Similar results were obtained following treatment with NC-PEG (FIG. 25).

PEG modification of ChIFN-γ reduced its rate of clearance from the serum following i/v injection (FIG. 26) and i/p injection (FIG. 27), thereby allowing prolonged persistence of biologically active ChIFN-γ.

EXAMPLE 10

Synergy Between Avian IFN-γ and Type II IFNs

ChIFN-γ shows synergy with ChIFN-α and ChIFN-β in both the CEF and nitrite assays. CEFs were cultured in the presence of ChIFN-γ that had been serially diluted in a limiting amount of recombinant ChIFN-α. The combination of the two IFNs was up to 5 times more effective than either type of IFN alone (FIG. 28A). A similar level of synergy was shown in the nitrite assay (FIG. 28B). Native ChIFN-β was also able to synergise with ChIFN-γ (FIG. 28C).

REFERENCES

1. Amann and Brosius (1985). *Gene* 40, 183.

2. Ausubel, F. M. et al. (1987) In Current Protocols in Molecular Biology, Wiley Interscience (ISBN 047140338).

3. Beug, H. et al (1979). *Cell* 18, 375–390.

4. Dalton, D. K., et al. (1993). *Science* 259, 1739–1742.

5. Digby, M. R., et al. (1995) *J. Interferon Cyt. Res.* 15, 939–945.

6. Dijkmans, R. et al. (1990) *Vet. Immunol Immunopathol* 26, 319–332.

7. Ding, A. H., et al. (1988). *J. Immunol.* 141, 2407–2412.

8. Fast, D. J. et al (1993). *J. Interferon Res.* 13, 271–277.

9. Huang, S. et al (1993). *Science* 259, 1742–1745.

10. Johnson, D. C., et al. (1988) *Virology* 164, 1–14.

11. Landolfo, S., and Forni, G. (1988) *J. Immunol.*, 141, 2831–2836.

12. Kaiser, P., et al. (1998) *J. Interferon Cytokine Res.*, 18, 711–720.

13. Kita, Y., et al. (1990) *Drug Design Delivery*, 6, 157–167.

14. Lambrecht, B., et al. (1999) *Vet. Imm. Immunopathol.*, in press.

15. Lillehoj, H. S. et al (1992) *Poult. Sci. Rev.* 4, 67–85.

16. Lowenthal, J. W. et al (1993) Immunol. *Cell Biol.* 72, 115–122.

17. Lowenthal, J. W. et al (1995a) In: *Adv. Avian Immunol. Res.* (Eds, Davison T. F., et al.) Carfax, Oxford. pp179–186.

18. Lowenthal, J. W., et al (1995b) *J. Interferon Cyt. Res.* 15, 933–938.

19. Lowenthal, J. W., et al (1997) *J. Interferon Cytokine Res.*, 17, 551–558.

20. Lowenthal, J. W., et al (1999) *J. Interferon Cytokine Res.*, in press.

21. Prowse, S. J. et al. (1989) *Avian Pathol.* 18, 619–630

22. Pusztai, R. et al. (1986). *Acta Virol.*, 30, 131–136.

23. Rose, M. E., et al. (1991) *Infection Immun.*, 59, 580–586.

24. Sambrook, J. et al (1989). In: Molecular Cloning: A Laboratory Manual, Cold Spring Harbor Laboratory Press.

25. Schultz, U. et al (1995). *Eur. J. Immunol.* 25, 847–851.

26. Sekellick, M. J. and Marcus, P. I. (1986). *Methods Enzymol.* 119, 115–125.

27. Sekellick, M. J. et al (1994). *J. Interferon Res.* 14, 71–79.

28. Shimatake and Rosenberg (1981) *Nature* 292, 128

29. Snapper, C. M., et al. (1987) *Science*, 236, 944–947

30. Steeg, P. S., et al. (1982) *J. Exp. Med.*, 156, 1780–1793.

31. Studier and Moffat (1986) *J. Mol. Biol.* 189, 113

32. Sung, Y. J. et al (1991). *J. Leukocyte Biol.* 50, 49–56.

33. Thacore, H. R. et al (1985). *Interferon Res.* 5, 279–288.

34. Thompson et al., (1994) *Nucl. Acids Res.* 22, 4673–4680.

35. Von Bulow, V. et al (1984). *Avian Pathol.* 13, 621–637.

36. Weiler, H. and Von Bulow, V. (1987). *Avian Pathol.* 16, 439–452.

37. Weissmann, C., and Weber, H. (1986). *Prog. Nucleic Acid Res.* 33, 251–300.

38. Wheelock, E. F. (1965) *Science*, 141, 30–311.

We claim:

1. A method of enhancing the growth performance of a healthy or diseased bird, said method comprising administering to said bird an avian IFN-γ cytokine polypeptide for a time and under conditions sufficient to induce weight gain in said healthy or diseased bird or to prevent weight loss in said diseased bird, wherein said avian IFN-γ cytokine polypeptide is selected from the group consisting of:
   (a) a polypeptide encoded by DNA present in an avian DNA library, wherein said DNA hybridizes under conditions of at least moderate stringency with a probe having a sequence complementary to at least 50 contiguous nucleotides of SEQ ID NO: 1; and
   (b) a polypeptide encoded by a nucleotide sequence that is degenerate with a DNA molecule according to (a).

2. The method according to claim 1, wherein the avian IFN-γ cytokine polypeptide is administered by a method comprising administering to the bird nucleic acid encoding said avian IFN-γ cytokine polypeptide.

3. The method according to claim 2, wherein the nucleic acid is in an attenuated live viral vector and in a form suitable for expressing the avian IFN-γ cytokine polypeptide in a bird.

4. The method according to claim 3 wherein the viral vector is fowl adenovirus vector.

5. The method according to claim 2, wherein the nucleic acid is in a non-replicating viral vector and in a form suitable for expressing the avian IFN-γ cytokine polypeptide in a bird.

6. The method according to claim 2, wherein the nucleic acid is in a plasmid vector and in a form suitable for expressing the avian IFN-γ cytokine polypeptide in a bird.

* * * * *

SEQUENCE LISTING

<160> NUMBER OF SEQ ID NOS: 10

<210> SEQ ID NO 1
<211> LENGTH: 1079
<212> TYPE: DNA
<213> ORGANISM: Gallus sp. (chicken)
<220> FEATURE:
<221> NAME/KEY: CDS
<222> LOCATION: (134)..(625)
<221> NAME/KEY: mat_peptide
<222> LOCATION: (191)..(625)
<221> NAME/KEY: 3'UTR
<222> LOCATION: (626)..(1079)
<221> NAME/KEY: 5'UTR
<222> LOCATION: (1)..(133)

<400> SEQUENCE: 1

```
ggatccacta gtaacggccg ccagtgtggt ggaattcaga agacataact attagaagct      60
gaagctcact gagcttatat ctgacatctc ccagaagcta tctgagcatt tgaactgagc     120
catcaccaag aag atg act tgc cag act tac aac ttg ttt gtt ctg tct        169
            Met Thr Cys Gln Thr Tyr Asn Leu Phe Val Leu Ser
                -15                 -10 gtc atc atg att tat tat gga cat act gca agt agt cta aat ctt gtt       217
Val Ile Met Ile Tyr Tyr Gly His Thr Ala Ser Ser Leu Asn Leu Val
        -5              -1   1               5 caa ctt caa gat gat ata gac aaa ctg aaa gct gac ttt aac tca agt       265
Gln Leu Gln Asp Asp Ile Asp Lys Leu Lys Ala Asp Phe Asn Ser Ser
 10              15                  20                  25 cat tca gat gta gct gac ggt gga cct att att gta gag aaa ctg aag       313
His Ser Asp Val Ala Asp Gly Gly Pro Ile Ile Val Glu Lys Leu Lys
             30                  35                  40 aac tgg aca gag aga aat gag aaa agg atc ata ctg agc cag att gtt       361
Asn Trp Thr Glu Arg Asn Glu Lys Arg Ile Ile Leu Ser Gln Ile Val
                 45                  50                  55 tcg atg tac ttg gaa atg ctt gaa aac act gac aag tca aag ccg cac       409
Ser Met Tyr Leu Glu Met Leu Glu Asn Thr Asp Lys Ser Lys Pro His
         60                  65                  70 atc aaa cac ata tct gag gag ctc tat act ctg aaa aac aac ctt cct       457
Ile Lys His Ile Ser Glu Glu Leu Tyr Thr Leu Lys Asn Asn Leu Pro
 75                  80                  85 gat ggc gtg aag aag gtg aaa gat atc atg gac ctg gcc aag ctc ccg       505
Asp Gly Val Lys Lys Val Lys Asp Ile Met Asp Leu Ala Lys Leu Pro
 90                  95                 100                 105 atg aac gac ttg aga atc cag cgc aaa gcc gcg aat gaa ctc ttc agc       553
Met Asn Asp Leu Arg Ile Gln Arg Lys Ala Ala Asn Glu Leu Phe Ser
                110                 115                 120 atc tta cag aag ctg gtg gat cct ccg agt ttc aaa agg aaa agg agc       601
Ile Leu Gln Lys Leu Val Asp Pro Pro Ser Phe Lys Arg Lys Arg Ser
            125                 130                 135 cag tct cag agg aga tgc aat tgc taatggcatc ttatgacctc ctgtgctcaa      655
Gln Ser Gln Arg Arg Cys Asn Cys
        140                 145 ctatttaaa ttttacaatg cacaattttt atgttgtgat tttttaactg agtttatata      715
catttattta ttaatattta agtattttaa ataattattt atattaaaaa aaaccaggc      775 aaacaatgaa agtatttata cctcctactg ctgtgtaaga aacggattgt ggtcttaaaa     835
tactgtctat ctgttgtgtg tgggttgact gaaataccg aatgaggtgg atgtttacca      895
gtttctgtgt gggaaatact gaattggagg tggatctgta ctcaagaaaa cccactcatc     955
```

```
ccggtcagtc tagtatttct aaatccaaat caaggagtgg cttgtttaaa gggaaaaaat    1015
gtgagcactc tctgactggg tcttagagat tttactgatg gtttggcatg actaagaatt    1075
tagg                                                                1079
```

<210> SEQ ID NO 2
<211> LENGTH: 164
<212> TYPE: PRT
<213> ORGANISM: Gallus sp. (chicken)

<400> SEQUENCE: 2

```
Met Thr Cys Gln Thr Tyr Asn Leu Phe Val Leu Ser Val Ile Met Ile
            -15                 -10                  -5

Tyr Tyr Gly His Thr Ala Ser Ser Leu Asn Leu Val Gln Leu Gln Asp
         -1   1               5                  10

Asp Ile Asp Lys Leu Lys Ala Asp Phe Asn Ser Ser His Ser Asp Val
             15                  20                  25

Ala Asp Gly Gly Pro Ile Ile Val Glu Lys Leu Lys Asn Trp Thr Glu
 30                  35                  40                  45

Arg Asn Glu Lys Arg Ile Ile Leu Ser Gln Ile Val Ser Met Tyr Leu
                 50                  55                  60

Glu Met Leu Glu Asn Thr Asp Lys Ser Lys Pro His Ile Lys His Ile
                 65                  70                  75

Ser Glu Glu Leu Tyr Thr Leu Lys Asn Asn Leu Pro Asp Gly Val Lys
             80                  85                  90

Lys Val Lys Asp Ile Met Asp Leu Ala Lys Leu Pro Met Asn Asp Leu
         95                 100                 105

Arg Ile Gln Arg Lys Ala Ala Asn Glu Leu Phe Ser Ile Leu Gln Lys
110                 115                 120                 125

Leu Val Asp Pro Pro Ser Phe Lys Arg Lys Ser Gln Ser Gln Arg
                130                 135                 140

Arg Cys Asn Cys
            145
```

<210> SEQ ID NO 3
<211> LENGTH: 164
<212> TYPE: PRT
<213> ORGANISM: duck

<400> SEQUENCE: 3

```
Met Thr Cys Gln Thr Tyr Cys Leu Phe Val Leu Ser Val Ile Met Ile
  1               5                  10                  15

Tyr Phe Gly Cys Ser Gly Ser Ala Leu Phe Leu Gly Gln Leu Gln Asn
                 20                  25                  30

Asp Ile Asp Lys Leu Lys Ala Asp Phe Asn Ala Ser Asn Ser Asp Val
             35                  40                  45

Ala Asp Gly Asn Pro Val Phe Ile Glu Lys Val Lys Asn Trp Thr Glu
 50                  55                  60

Arg Asn Glu Lys Arg Ile Ile Leu Ser Gln Ile Val Thr Leu Tyr Leu
 65                  70                  75                  80

Glu Met Leu Lys Lys Thr Asp Met Ser Lys Pro His Ile Lys Asn Leu
                 85                  90                  95

Ser Glu Gln Leu Asn Thr Leu Arg Asn Thr Leu Ser Asn Asp Tyr Lys
                100                 105                 110

Lys Phe Arg Asp Leu Val Glu Leu Ser Asn Leu Gln Leu Thr Gly Leu
            115                 120                 125
```

Lys Ile Gln Arg Lys Ala Val Ser Glu Leu Phe Ser Val Leu Gln Lys
            130                 135                 140

Leu Val Glu Thr Ser Thr Ser Lys Arg Lys Arg Ser Gln Ser Pro Lys
145                 150                 155                 160

Arg Cys Arg Cys

<210> SEQ ID NO 4
<211> LENGTH: 164
<212> TYPE: PRT
<213> ORGANISM: turkey

<400> SEQUENCE: 4

Met Thr Cys Gln Thr Tyr Asn Leu Phe Val Leu Ser Val Ile Met Ile
1               5                   10                  15

Tyr Tyr Gly His Thr Ala Ser Ser Leu Asn Leu Val Gln Leu Gln Asp
                20                  25                  30

Asp Ile Asp Lys Leu Lys Ala Asp Phe Asn Ser Ser His Ser Asp Val
            35                  40                  45

Ala Asp Gly Gly Pro Ile Ile Val Glu Lys Leu Lys Asn Trp Thr Glu
        50                  55                  60

Arg Asn Glu Lys Arg Ile Ile Leu Ser Gln Ile Val Ser Met Tyr Leu
65                  70                  75                  80

Glu Met Leu Glu Asn Thr Asp Lys Ser Lys Pro His Ile Lys His Ile
                85                  90                  95

Ser Glu Glu Leu Tyr Thr Leu Lys Asn Asn Leu Pro Asp Gly Val Lys
            100                 105                 110

Lys Val Lys Asp Ile Met Asp Leu Ala Lys Leu Gln Met Asn Asp Leu
        115                 120                 125

Arg Ile Gln Arg Lys Ala Ala Asn Glu Leu Phe Ser Ile Leu Gln Lys
            130                 135                 140

Leu Val Asp Pro Pro Ser Ser Lys Arg Lys Arg Ser His Pro Gln Arg
145                 150                 155                 160

Arg Cys Asn Cys

<210> SEQ ID NO 5
<211> LENGTH: 164
<212> TYPE: PRT
<213> ORGANISM: pheasant

<400> SEQUENCE: 5

Met Thr Cys Gln Thr Tyr Asn Leu Phe Val Leu Ser Val Ile Met Ile
1               5                   10                  15

Tyr Tyr Gly His Thr Ala Ser Ser Leu Asn Leu Val Gln Leu Gln Asp
                20                  25                  30

Asp Ile Asp Lys Leu Lys Ala Asp Phe Asn Ser Ser His Ser Asp Val
            35                  40                  45

Ala Asp Gly Gly Pro Ile Ile Val Glu Lys Leu Lys Asn Trp Thr Glu
        50                  55                  60

Arg Asn Glu Lys Arg Ile Ile Leu Ser Gln Ile Val Ser Met Tyr Leu
65                  70                  75                  80

Glu Met Leu Glu Asn Thr Asp Lys Ser Lys Pro His Ile Lys His Ile
                85                  90                  95

Ser Glu Glu Leu Tyr Thr Leu Lys Asn Asn Leu Pro Asp Gly Val Lys
            100                 105                 110

Lys Val Lys Asp Ile Met Asp Leu Ala Lys Leu Arg Met Asn Asp Leu
        115                 120                 125

Arg Ile Gln Arg Lys Ala Ala Asn Glu Leu Phe Ser Val Leu Gln Lys
    130                 135                 140

Leu Val Asp Pro Pro Ser Ser Lys Arg Lys Arg Ser Gln Ser Gln Arg
145                 150                 155                 160

Lys Cys Asn Cys

<210> SEQ ID NO 6
<211> LENGTH: 164
<212> TYPE: PRT
<213> ORGANISM: guinea fowl

<400> SEQUENCE: 6

Met Thr Cys Gln Thr Tyr Asn Leu Phe Val Leu Ser Val Ile Met Ile
1               5                   10                  15

Tyr Tyr Gly His Thr Ala Ser Ser Leu Asn Leu Val Gln Leu Gln Asp
                20                  25                  30

Asp Ile Asp Lys Leu Lys Ala Asp Phe Asn Ser Ser His Ser Asp Val
            35                  40                  45

Ala Asp Gly Gly Pro Ile Phe Ile Glu Lys Leu Lys Asn Trp Thr Gly
        50                  55                  60

Ser Asn Glu Lys Arg Ile Ile Leu Ser Gln Ile Val Ser Met Tyr Leu
65                  70                  75                  80

Glu Met Phe Glu Asn Thr Asp Gln Ser Lys Pro His Ile Lys His Ile
                85                  90                  95

Ser Glu Glu Leu Cys Thr Leu Arg Asp Ser Leu Ser Asp Gly Val Lys
            100                 105                 110

Lys Val Lys Asp Leu Met Asp Leu Ala Lys Leu Leu Met Thr Asp Leu
        115                 120                 125

Arg Ile Gln Arg Lys Ala Ala Asn Glu Leu Phe Ile Val Leu Gln Lys
    130                 135                 140

Leu Val Asp Pro Pro Ser Leu Lys Arg Lys Arg Asn Gln Pro Gln Arg
145                 150                 155                 160

Arg Cys Asn Cys

<210> SEQ ID NO 7
<211> LENGTH: 164
<212> TYPE: PRT
<213> ORGANISM: Japanese quail

<400> SEQUENCE: 7

Met Thr Cys Gln Thr Tyr Asn Leu Phe Val Leu Ser Val Ile Met Ile
1               5                   10                  15

Tyr Tyr Gly His Thr Ala Ser Ser Leu Asn Leu Val Gln Leu Gln Asp
                20                  25                  30

Asp Ile Asp Lys Leu Lys Ala Asp Phe Asn Ser Ser His Ser Asp Val
            35                  40                  45

Ala Asp Gly Gly Pro Ile Ile Val Glu Lys Leu Lys Asn Trp Thr Glu
        50                  55                  60

Arg Asn Glu Lys Arg Ile Ile Leu Ser Gln Ile Val Ser Met Tyr Leu
65                  70                  75                  80

Glu Met Leu Glu Asn Thr Asp Lys Ser Lys Pro His Ile Lys His Ile
                85                  90                  95

Ser Glu Glu Leu Tyr Thr Leu Lys Asn Asn Leu Asn Asp Gly Thr Lys
            100                 105                 110

Lys Val Lys Asp Ile Met Asp Leu Ala Lys Leu Gln Met Asn Asp Leu

-continued

```
                115                 120                 125
Arg Ile His Arg Lys Ala Ala Asn Asp Leu Phe Ser Val Leu Gln Lys
    130                 135                 140
Leu Val Asp Pro Pro Ser Ser Lys Arg Lys Arg Ser Gln Cys Leu Arg
145                 150                 155                 160
Arg Cys Ser Cys

<210> SEQ ID NO 8
<211> LENGTH: 19056
<212> TYPE: DNA
<213> ORGANISM: fowl adenovirus serotype 8 (FAV8)
<220> FEATURE:
<223> OTHER INFORMATION: Description of Artificial Sequence:
      oligonucleotide used to amplify mature interferon coding sequence.

<400> SEQUENCE: 8
agacctcgtc ttcgccacgg tcaaggagaa gatcggctgg cggcggttcg tggaagctat      60
ccaacggtac gtggctgacg cctacggtgc tttcctgaca ctcaatgcgg aaaccgcacc     120 cgtcggggt gacgaagata acgccgtcag tgtgctcatt gacactttag gcgaagaaag      180
ggctatttta gcagcttatc gggtggcgga aaagctatta gcgataagc cgctgccaaa      240 cgacggcgag aacaatgggt ccgaaaatcc cgggacgcc gcgcatactt ttgcggagag      300
tcccgaatcg gacgaggacg tacaaaaggc gtccgccgag agctctcccg acacaccagc    360
tcgagacttt accgcggaag ccgtaaccgt gtacatcgac tcggacggcg gttgcgagga    420
cagcagcgaa gaagatcagg aggaagagga ggaggacgat gaagaagaag acgaagaaga    480
agaagacgaa gaggaggagg aggaagagga ggaggaggga gacgacggaa cacccgagtc    540
taccccttct accgtcatcg aagcggcgaa tctctcgccg gtcggcaccg acgaaaagca    600
cggggaaccc gacggcgagc ccgatgatgg tgacaatgac gacggagagg acgagggaag    660
aaattctgac gaggatagcg gatactattg gggggatgac accccctgg aattggttcg     720 cgatcgcggg acaggcgatc acggtgagcc agatagcacc gctccttccg acggtcctgg    780
ggaagctccg tcggccgacg gggtagacga ggagcaggag caagacgaac aagagggaga    840
gaccgccgtc cccgccgcca ccgctcagcc cgctttcgac aaatgcctcc aacggcaagc    900
catgatgctc accggcgctt tgaaagacgc cttacccgag caggaacgcg acgtgcccct    960
ctgcgtcgat agcgtgcaat accagctcga gcgctacatc tttaacccg atatgcgtgt    1020 cccctccggaa taccgcgaag tgcgctttaa cttctatccg cccttcatgc gcccccaaagc    1080 gatcgcgaac taccacatttt cgccgtcac ggcgcccatt ccggcaagtt gcaaagccaa      1140
ccgcagcggg agccagctct tagaagcttg tcgcgacatg aaagtgttca agcgcttacc    1200
tcgttggcgc ctcaacgtcc aatccgacga cgggctcggg gacgaagtgg tacctgtaac    1260
agagctgaca gatgccaaat tagtccctct caaggacgac atctcgcggt tgcagtgggc    1320
taaaatgcgc ggtgaacaca tccgcttttt tagctaccct tccctgcaca tgcctcccaa    1380
gatctcacgt atgctcatgg agtgtctgct ccaacccttc gcaaacgaaa acgacaaggc    1440
ggaacaggtc gcccccctgcg tgagcgaaga ggaaatgcgt tttattgtag atccggagca    1500
gagaatgaga ggcgaggaac tctacaaggc catgctcaaa aggagggccg tcgttaccat    1560
ggccgtgcgg tacaccgctt tgctcgagct catggaacgc gtcttccgag agccttcctc    1620
cgtcaaaaaa gcccaagaag tgctccatca cacccttcat cacggcttcg tggcccaagt    1680
gcgcgaaacg gccaaagtga acctgagcaa ctacgccacc taccacggcg tcacctacaa    1740
```

-continued

```
cgacccgctc aacaactgca cgtcagccaa gcttttcgaa ggcagggaca aggaggatta    1800
cgtgctcgac accgtctacc ttttcttggt cctcaattgg caaaccgcga tgggtatgtg    1860
gcagcaagcc atcgatgata ccaccctgga catctacgcg aaagccttta cgcgccagcg    1920
acgcgccatt tacggcctcg gaagcgtcac cgaggtcagc aaggccatcg tcgacatcct    1980
gatggacggg gacaggctca cggaggaaat gcggaaagcc ctccccaact tcgtgacgca    2040
gagccagatc tccgattttc ggcactttgt caccgaaagg tcgaacgtcc cctccatggc    2100
cgccccgttc tacccctccg atttcgtccc gttggctttc cggcaaagcg ccctctgct    2160 ctgggaccag gtctacctcc tccagatcgc cttttcctc accaaccacg aggatacct    2220 gtgggaaccg cccgagagcg aagcggaggt gccgcagcac cgcacttact gcccctgcaa    2280
tctctgcagc ccgcaccgca tgccggcgga taacgtcgct ctgcacaacg aagtgctcgc    2340
catcggcact ttcgagattc gcagcgccga aggcaaatct ttcaggctca cgcccgaact    2400
ctgggccaac gcctatctcg ataaattcgt gcccgaggac ttccatcctt tcaccgtgtt    2460
ccactttccc gaaaaccgct cttccttcac caaaaatcac accggttgcg tcacggaaag    2520
tccggaaatc ctctctctga ttcgtcagat ccaggcctcc agggaggagt ttctcctccc    2580
cgagcaaggg gctctacaaa gacccgcaga ccggcgaaac gctcaccact tcggtcgggg    2640
cagagaaccg tcctggagcc tccggcggag cgcctctacc gcccgctgcc gccagtacct    2700
gcggaggagc tcgagcgccg ccgaaacctc ctagggctct acggtctgcc tgccctgctg    2760
cagacccgga ctcccagagc gactacgggg aagctgctct cgcgtccaac tacggccgat    2820
atggctcaga ggatgctgga cgagaaaatc agagttaccg aagaccctcc ggaacccgag    2880
aacgccgttc ccttccctac ggacgcccgg ttcgtggggg ttcgcccgtg cggaggacct    2940
gaagtgagcg aatcagacgg agaaacgtta gaagccggac accgagagat ctgagtacca    3000
tctcggagag gaggaggacc tcgaagagat ggagaaagag aatatcccac cgcggccctc    3060
ctcgctgcct ctggacggga cgcggaaccg caagcgccgc tccgcatcct cgcccgggaa    3120
ggagctgaag aggcctccga tccgaaagag agccaaatcc gataaagacg cggagaccgc    3180
gcccgcgtcc aaaaagcgcc gtcctcgagg taactataga agctgggtca ggcaccgcgt    3240
ggcgatctgc caagcgctcc gcgacgccgt tttcgaccga aggctggcgg ccgaaatcct    3300
aaagagagcg cgcggtatct tcgtaccgcc caccgtattg ggctactacg cccgcaaact    3360
cctagaactt cccgacgaag atcactgatc gtcggctttt tctttctcct ttccttctta    3420
gcggctcccg ctaccgcctc tgacacgctc cctccgcctc tcccgccgaa aaaacgcccc    3480
aaaaatacgc cgcggaccga ctcgtccttc gaattggtcc ctcccgaggt cgcagacttg    3540
aaagccaaca tcctcgacgt gctcgtcgaa atcgaaaata tcgccaaaaa cgacccttca    3600
cggcgcgttt ccatccgcaa ccgcacccgg gaaagcatca ctcggcagtt acactacgtc    3660
aaggacgagc aaaaactcac caagcttaag gcagatgcgg aaaaaatcct gcacctgtgg    3720
aaatcccttt cctaatcccg cttcttttat agcgctacag accgcgtgac tgagcccgcg    3780
gcaacatcat gaacctcctc gaagccactc ctaccgagta cgtgtggaaa tacaaccccc    3840
tctccgggat tccgccggc gcgcaacaga attacgcgagc gaccataaac tgggtggtgc    3900
ccggaggtaa cagtttcgct tacgcggcgg acgagataag acggcacacc ctaagccctg    3960
ccgccacccg cgcgatcacc gaacgtttcg aagctgagtc agaccagcaa cccttcgcca    4020
acgcccggga aaccgcctac atcaccgcca acgtgctgga ctctggcttt ccaaagtccg    4080
ccgtgtaccc cgtggaccct tccggagttc aacgggttca gctctcgggc ggcgccgagg    4140
```

-continued

```
gccggatgca actcgcgggt ggcctcaccg aaggtcgagt gcaactttcg ggaggtgtcc      4200
taggacacgt cgtgcctcct gggggggagaa gacgcgccgg cgggcgtccg ccgcgatggt      4260
gtgggaccgc tctcgcggga aacgggcttc ccgaggacgc cgaagtggtt tcggatacct      4320
acaagtactt cctccgcacc cagggaccca gccaagtcgt gcaagaaccc ggcgtgtact      4380
cgcggaggca gttcatgacc accttcctgc cggccgtggt gccccgacct ttcagcagtc      4440
ccaatccgcg cgactttccc gcgcagtaca gcgccatcta caaaggcacc aacgcgtacg      4500
aggacgtatt ttgggactgg tgaagtccct cttcgcggct tacccgttgc tgacggtgct      4560
ctgtttcgca ataaagttct tccaattcag cctcgctgaa cggttcccgc tcgttattg       4620 tcacgcgttc gcctccgtcg ctcaccacgc gcgcgcgaaa ccgtcttttg atccaaaaga      4680
cgtaaccggg gtttaggggt tgcgcaaacc tcacgatcgc ctggtcgttg actttcaacc      4740
aatatttttt aggagcctgc gactccgtct ccgacatggc gacctcgact cctcacgcct      4800
tctcctttgg ccaaatcggc tcccgaaaac gccctgcggg tggcgatggc gagcgagacg      4860
cctccaaagt gccgaaaatg cagaccccg ctccgagcgc gaccgccaac ggaaatgacg       4920
agctggacct ggtctacccc ttttggctcc aaaacggctc taccggagga ggcggcggcg      4980
gcggttccgg tggaaacccg tccctcaacc cgccgttttt ggaccccaac ggaccccctgg     5040 ccgtccaaaa cagcctcctg aaggtcaata ccgcagcccc catcaccgtc accaataagg      5100
ccctgacact cgcctatgaa ccggagagtc tcgagctcac taaccaacag caactggcgg      5160
tcaaaatcga ccccgaagga cctctgaaag ccacgaccga gggaatacag ctgtcggtcg      5220
accctacgac gttggaggtt gatgacgtcg actgggagtt aaccgtgaaa ctcgaccccg      5280 atggcccct ggattcctca gccgcaggaa tcacggtccg agtcgatgag accttgctca       5340
tcgaagatgc tggatccgga cagggcaaag aactcggagt caatctcaac cccacgggac      5400
cgattacggc cgacgaacag ggcctggact tagaaataga caaccagaca ctcaaggtca      5460
acagtgtcac cggcgggggc gtcctagctg tacaactcaa atcccaaggt ggacttaccg      5520
tacagactga cggtatccaa gtgaacactc aaaacagcat caccgttact aacggagctc      5580
tggacgtgaa agtagccgcc aacgaccctt tggaatcaac cgacaccggg ctcacactta      5640
attatgaccc cggagacttc acagttaatg cgggcacgtt gagcattatt agggacccgg      5700
ctctcgtagc caatgcgtac ctcacatccg gcgcctccac ccttcagcaa tttacagcta      5760
agagtgaaaa ttccagtcaa ttttctttcc catgcgcata ctatctgcaa cagtggcttt      5820
ccgatgggtt gattttttagc tccctctatc tgaagctcga caggcacagt tcacgaacat      5880
accaacgggt gaaaattatc agaacgccaa gtactttacc ttctggggttg gagcgggcac      5940 ttcatttaat ctttctaccc ttacccaacc cactattaca cccaacacca cacaatggaa      6000
tgcattcgca cctgctcttg attactcagg tgctcctccc ttcatctacg acgcgtcttc      6060
cgtagttaca attttatttg aacccaccag tggtcgactg gaaagctatc tccccgtcct      6120
taccgataac tggagccaaa caacctacaa ccccggcacc atcaccctgt gtgtaagaac      6180
ggtaagggtt caattgagat cgcaagggac cttcagcact ctagtctgtt acaacttccg      6240
ctgtcagaac gcgggcattt ttaacagcaa cgctacaacg ggaaccatga ccctgggtcc      6300
tatcttctgt agttatcctg ccttgagcac cgccaacgct ccttaattca ataaaaaatg      6360
atccacacaa tatgaaggtc tactgtgatt ttttattaaa gcagccatac taattctcct      6420
ggatacccat cagtctgtcc cactctccgc gttgccagta gtacaggcag ttcacggcgt      6480
```

-continued

| | |
|---|---|
| ccacgtacca cgattcgctc accagaaaga cccgctgctc gggaaaatcc accatcattc | 6540 |
| tgcggatgta gtgacaaggg agcgcccca tctggccgag cgtggccacc gcttccacga | 6600 |
| acacaccggt gttgtgcgga gggacataga tgatcatgcc cagaactcct ccgcgggcgc | 6660 |
| ggcgcagaag acgggataaa attcggtaaa catgacagag gcccacgccg ctacgaagta | 6720 |
| cacccctcc agactaggt cgccttccag cctgctccaa aggtacacgg agagaccact | 6780 |
| gctgtcgggt tgactgcaca cggccatcgg cacgcgtctc atctcgaatc cgtggcagtg | 6840 |
| acaccgctcc ggaatcatct cgaattcttc caaacataga aactggtgcg cgtggacggc | 6900 |
| cggcacgaaa cgcaaatctc cttccctgc tcccaccgcg ggttgatgtt ccctatgtc | 6960 |
| ttcgccccat aacctctgag cggccatgat ctacacctgg gattcttcgc gctctatctc | 7020 |
| agtatacacg tgttccacag agccgccgta gacctcttcc tcgtcgctac ctgccggtgg | 7080 |
| cgctctcagc aacgacagtt ccagtggtgt cggcggcgt ggaacagaag gaggcggtga | 7140 |
| acgggtatcc gagcgggagt cgtaaaacgg attgctgctc acagtccaat tgggggaacg | 7200 |
| agcgggaaac tgagacaggg aacgcagcca ggagaaccga cgtgatggct cgcggttatt | 7260 |
| aggcaatggt gggggtaaag cagaacaccg gcgacggata ctccaacggt gtcctcggat | 7320 |
| gctcttgagg acctcccgca atgattctcc gccactgcgc gatcagcaat acaaacgcga | 7380 |
| tcgtggctag aagagtgcaa cagccaaaca tcataaacac gtagggaacg gcatgtaaat | 7440 |
| attgactgag gaagagataa ctggcggcca ccgcaccgca gtgaatgact cccacggtca | 7500 |
| cagccagaag cagcagaagg catgcctctc tgcggcgccg gcggatccgc acctatcaat | 7560 |
| agaaaaaagg ggactttcta tcaccctcca cgcgtgcccg gcgcttggac atgcaattcc | 7620 |
| gcaaatagga caactgagct atagtggcta ggggcaaggc ctgtctaaga gggcatccgg | 7680 |
| ggcaagaagc ttcggggtga tggtcgcagt acgtgccgtg aacatgcagt acccattctt | 7740 |
| ctacatccac aaacgtggcg gtacgggaag cggaatgtag cataacccc gcgacaccat | 7800 |
| gctccagcaa gcggggtcgg ccatctcttt cagcatggat cgggtcatca gaggctgggt | 7860 |
| cacgggactg cccttcccgc aagttttaag aatgacggtc gctaccacat tggtgcgaca | 7920 |
| cgcacccaga tagagaacgg gatatttcaa aaaggcagg tgctcaggca cgaccgtctg | 7980 |
| ggaaacctca taacataatg attgaagagc caaccgaaag gcaacaccgg tctctagaac | 8040 |
| gagtcccgta tctacaaaca gaaagtcggt tttgttttg cgaaccatcc attcccgatg | 8100 |
| tttctctatc agaggttccc gcgctacgaa cagacgcctc gaaaccgctc gcaggatctc | 8160 |
| ctcctttcc gcgggtgata agacaaccg agactgcagt ctcagtatga cgttcaacag | 8220 |
| aacgcacggt cccgtcttga gtctgagata cttcgaacac ctgcagctca ctaccgtata | 8280 |
| cagggactcg tgccacgagt aatgctgggg tttatcgaag agactaatgg aggctacgga | 8340 |
| acggctcgtg tgatactcca tcatgcgttc cgctgcttct tgggacggac cctgtctgac | 8400 |
| caggatgctg aaccatatgg ctccgcattc gttttgatag ccgcaaccgc gggtaacggc | 8460 |
| aaccacctcc tacacgaaag aaaggggcgc cttaagttac tcaaggaaac cgcccgggaa | 8520 |
| aaatcggggc aatgaaaagc tatcactcac cgaatcagaa cacagaggca tgatgcgtaa | 8580 |
| ctaagacagc tcttttattg atcaggtacc gtcacctgta aagatacaca cattaaacga | 8640 |
| tacggtaaga gtcaccgcgg taacaccgac atcggtagtg gcagaatata tagagcacga | 8700 |
| ctgctgtcgt gaacagagca gctacgacac cacccgtaac aatcgcgagg cgcgcggcat | 8760 |
| cgtcttccca aaattcacgg atcagagagt agaactctcc tccgagctga ggagacgtag | 8820 |
| ggaaggatcc cgtagaccca ttgctacttt tttccgtcgg atagcggtag agaccaacac | 8880 |

```
agctaccata gccaaaaaca caagccccac aaccgttaaa aaaagagttc cggtagatgc    8940
acccgaggcc gctactcgag agccctcgtc tatggctcgc aaggcgacgg cttgaaccgg    9000
ttcggtttcg tttagctgga cggtcactac ctcctcttct gacgcggttt ccgaagtgct    9060
ccaaaaatcg cttgaactcg gtgtagctgc tgagaaattc caggtcgaaa cggtcgatgc    9120
ggagtctgtc gatgtagagt tcaaagacgc agtaggttcg gcgggaact ccacagaaac     9180 gggttccagt gggcttaccg ttaccttcaa ttttataact tcaaattcaa gaaagaattc    9240
cagttcgaat acgtcggcat taaagaaggt gacggtaaat tctttcttca ttctgtccaa    9300
ttggaagaca cactgcgcag ctgtctgaca cacgtcccag aaactgtaca gtttatgggt    9360
ccccgaagaa tccgtaagtt ggatactcgt cagccgaaaa ggagacttgc taagatctac    9420
cttgagtcca tgtcccactt tcacttctac atcagccagc tggatcggaa tcatagctat    9480
cgaggcatct ctatccgcca ggcaaccaga ctgaggagga cactgactt gagatccgcc     9540 gttcggattt aacatcgtgc gataactcat taggggaat cgctccttgg ttaccatgca     9600
gtagtgcgca ggccgaccga acggatctct tgtagggtta cagtgcatgg tacgcacaca    9660
ccctccagtc attactttac ggtcctttat cgagggagcg cttgacgaat cctgatagaa    9720
tccctgtggt gtgatcacgt acaccaggta gatacttgca gaaggattcc agtgacggat    9780
ccacaacacc tcttctgcaa gctcggtgta acccaccgcg gtaagtacat catacctccc    9840
ataccgaagt gtttgctcac tgtaacctcc gatgaacatt cgactcccac tagaagctac    9900
tactatgatc atgatcggag ttacaaagtc ctgcttgagt acgggtgagt acgtaatctc    9960
agtcatgtag ctaatgctaa tatgattgaa gtagctagcg tatctgtaat ctcgactcat   10020 agtatacca ttccaagtgc tccggacagg acccactttg aaaccctcat taagcaagtg    10080
aaacatgggt aacccagttc tcacatccaa agtctttaga aacttcggta ctatcaatct   10140
atgaaaacag ccgcttttac tccacgtatc cctccatgag aattcttcgc agaccgtctg   10200
tccccataca ctttctgcac acactcttcc cgaccatccc ccatgaatcc cacaaccctct  10260 accgccctta tcctccaaca tgatatcctc agaagccgta taccctcctg taatccacga   10320
cccttccgtt ttcaggactg ccacgtaatc cgcatcattt ttatctaagc ctccggtaac   10380
aaacgtgggc tctaacccga ctattctggt acaccgtcta tccccagaaa tatatgtcca   10440
ctgtctgcag atagtagagc aagcgtgagc gccggcagaa tgtcctatac agtgtaacct   10500
tttcgaatgt ggtatgtccg acagaaactt cccgaaatca acatacagac cgtcatagtc   10560
gtagtacagg ttccagtcca ccaggagcag cgcgactgca ggcgtcatat tctgatggac   10620
acgcaacacc tgtctaaaac tttgatagcc catgtaatac cccggtataa gcacaatgat   10680
atcggtcttg ccggctaaag cactgtgcaa tcgatggtag acaccgtact ggtacgtcac   10740
gtcgtgaaat ttcggcacac ccccgtgagc tccataccg gtaatcttcg atggcggtcg    10800
gctcaatctt ccaacgcctc tcggagcatc aagtttaga gaatccggtc tcgccacgca    10860
tgaccgattg cccgaatcgg gacatgcaac tgccgatttc gcacgaaa gcacggaggc     10920 tccgaagagc accccgacca actgaaacag aacgcatgat ttagacccac tcccgacaga   10980
ggattaacgc gacccaatca agggatatca aaaagaatc cttaccgcgg agagattcat    11040
agaccgaaga gttgagagcg ctcctgtttc tctgaagatc tctcacccg actgtgacag    11100 atccacaaag cagcactcaa tttatactgt caaatggtta atgtttaatg ctagaaaagc   11160
gctgacaccc agtaaatatt tacttagttt gcagttccac tgtttcctta ttgccatgac   11220
```

```
tggacaaaaa ccacagataa gatgttccat tcaagggaac ccgatgttcc ctcgataact    11280
tcccggtaca aagtccaaaa atagaactag gtgctttata aatactaaga gtcgactcct    11340
tggtgtttca gaagaacaca gacgatctac aaacaggatg aacctcggaa gactcaacac    11400
cgccggtaag aacatcttaa tttttacttt gtatgatttt caattctgaa aaacacgttt    11460
cctggttcgt gcacgtacgc ggaaacgaag ttcgaaaaat cagagttgga attttccagc    11520
tatggttaac tattaactat atgacgtcac ttagttaatt attaacgata taagtaaat     11580 gattaactcg ggctagttaa tgattaacta tacctggtta atgattaact gacttagtta    11640
atgattaact agaagttaat gattaactag aagttaatga ttaactagaa gttaatgatt    11700
aatctattac gtcactcgtt atatattaac tagtgacgtc actcgttata cattaaccca    11760
ttacgtcact cgttatacat taactagtga cgtcatgagt aaatcattaa ccttcatgca    11820
tatgcatgag gagctactga atatgcatga gagcctcata catatgcatg gaacttatgc    11880
atattcacga cactcatgca tatgcatgca ttggttaaag agtaacccta tgactcagtg    11940
tgtatgttta cgttgcctag caacgttaat gatttacctg ctgacgtggc agctccgcct    12000 ccagtaaat catttacctg aactttgttc tttatgttta ttcaccatgg caacgctacc     12060
atatatggac atccgactcc gcctcccccg ttatacatta acgatggcgt gataggcgga    12120
gctctccccc attggctctc aatgacgtag ttcaggttaa ccataagcca gaaccgccta    12180
tataggtaga gcaggtagac ccggaacacc attcccatcc ggacctccat agagtgcgga    12240
cctctacggg ctctccatac cggtaaatat tttattccat ttaatccaat cgaataaatc    12300
aataatcaac tcaatgctgt gattctgcct caaattcaat ggtgattttc tttaataaaa    12360
agcccacccc ccttggcacc cccctgtaca cccccctgta caggcgacca cccccctatgg   12420 acacccccct gtacaggcga ccacccccta tggacacccc cctgtacagg cgaccacccc    12480
ctatggacac ccccctgtac accccctgt acaggcgacc accccctatg acacccccc     12540 tgtacaggcg accacccccct atggacaccc cctgtacac cccctgtac attttctccc    12600 ataggctaca atggaatact gccccctagt gtctcctgct gtatgggacc cctatgatgt    12660
gggcgccatt acctttgcca ctatggagct ccttcacgag ggggcgccat tgaaattggg    12720
agaccgcata gagagcctag ccaatggggt gctttggaat ccggatatcc ccgtccaact    12780
cttcaactgc ctttccattc gctcatgggg atcacatggg aagcgcgtca tgtaccgtgg    12840
ccacacctac cggatgtacc acgcccagtt acgggtccga agctccgccc ccgttactag    12900
gaaacaggcc ggaagcctgc tcctcagcct atcacagaag ctcctctgtt tcgccgcccg    12960
ctttaatacc catcccctcg tgatgcaatt ggggtgga tctaacccta tgggcctacc     13020
tgtatatacc aagagggccc tccagatggc gctacagagt atgcgggtgc gcattgcccc    13080
tgacggccag aagtgcgc caccggagat aggcaagacc tgtacggtga agcccctcaa     13140
gaccccggag accctccagc aggggtcttt cagtaccacc gatttaaaaa agacacttcc    13200
agattgggct tttcgccgac ttttaacca accccctat atttgtggat ggaagattgg     13260
caccgcgcca gaagggcgg agagttggat cgttacgctc caccccagc cttcgactcc     13320 gccccccaca gggaccaaga ctccgcccac tctgcaggac cttgcccggc tgggcgtggt    13380
cgagcaatgc ctcaagatga ggaggcgtgg cctggaccgc aggcaccacc cctatgctca    13440
ataaaccaat cagattccag tacttggctc ctcctatttg tgggcgggac tttgcacgcc    13500
tcttagcggc gccccctggc ggccgagggc cgccactgca cccctgtcgg acttagtctc    13560
tggcgcgggg ccggtcaatc attaacccga cggccggcac gggcgccccc tggcggcggg    13620
```

```
cgcccgccac tgcaccctgc gcctcttagc ggcgccccct ggcggccgag ggccgccact   13680
gcacccctgt cggacttagt ctctggcgcg gggccggtca atcattaacc cgacggccgg   13740
cacgggcgcc ccctggcggc gggcgcccgc cactgcaccc tgcgcctctt agcggcgccc   13800
cctggcggcc gagggccgcc actgcacccc tgtcggactt agtctctggc gcggggccgg   13860
tcaatcatta acccgacggc cggcacgggc gccccctggc ggcgggcgcc cgccactgca   13920
ccctgcgcct cttagcggcg ccccctggcg gccgagggcc gccactgcac ccctgtcgga   13980
cttagtctct ggcgcgggc cggtcaatca ttaacccgac ggccggcacg ggcgcccct   14040 ggcggcgggc gcccgccact gcaccctgcg cctcttagcg gcgccccctg gcggccgagg   14100
gccgccactg caccctgtc ggacttagtc tctggcgcgg ggccggtcaa tcattaaccc   14160
gacggccggc acgggcgccc ctggcggcg ggcgcccgcc actgcaccct gcgcctctta   14220
gcggcgcccc ctggcggccg agggccgcca ctgcacccct gtcggactta gtctctggcg   14280
cggggccggt caatcattaa cccgacggcc ggcacgggcg cccctggcg gcgggcgccc   14340 gccactgcac cctgcgcctc ttagcggcgc ccctggcgg ccgagggccg ccactgcacc   14400
cctgtcggac ttagtctctg gcgcgggcc ggtcaatcat taacccgacg gccggcacgg   14460 gcgcccctg gcggcgggcg cccgccactg caccctgcgc ctcttagcgg cgccccctgg   14520
cggccgaggg ccgccactgc accctgtcg gacttagtct ctggtgcggg cccgagtcac   14580
ggatggagta gtttccttg cggccagcag agggcatacc tttattctca gctcgcaagt   14640
ctcaatagat acacacctca tcggtgtaca gcgtgtccgc gtagcgcagc cccgtgcacc   14700
tcacccaacc acctatatcg cgaacggctc cggtactcac tatgtatttc ccgacgcgat   14760
agttcggatc attgcaccac ttattcaagt acattctaaa ccattgccct tcggggactt   14820
ggcgctgata aaacattcc ctgaagtacc gtttcaccgc gcgagaacac ttatacaagt   14880
atctgtcccg caggttgaac atggttaagc acagaagcaa ggtcatgtgg caggaacaag   14940
aaccgccagg ctgcaacccc acgcagtatc ccatcggatg accgatctcc gagttcgcct   15000
cctcgtggaa cgggtaccat agctgcttca cgtcttgaac cagcttccag aacactgcat   15060
cgtgcataca ccacggcggc acggcaactc cgaagatcac gtacagtggc atgttccgga   15120
tacatctacg acacaggtac tgtgacacct tgcgcgtacg cgaaaaggga acccgaccct   15180
cccccgtaac gctccactta cggacagccg gcgatgcgca ctgcgaacga aaataaaatc   15240
tgcgccgttg tgcgctccag gcggaaacag gggaatatat aagccaactc ttatcttat   15300 tgttgccacg cccgacacta tccagatttc gagacctgct gacaccaccg gaacacgcga   15360
cctcgccctc tctttatcat ccatacgccc aggtgactca gtcaaatccc ttatataaag   15420
accgttttta cctgaccgct tccacgtaca caaggcggca catgaaagca ccatgctgcg   15480
ccccgtatcc gccatcgcgt tcctctcgtg cctatgtctc acgcggaccg cgcaacaggt   15540
cggtaagtcc tttaatctta cgacccactc caacctcact gtgcacccgc agaccaaagg   15600
aacctcaaag caagagtggc ggctaggcg cgataccaag attgcgatgt gggagaaagg   15660
ctacgggtac agctacccgt cgggacccttt aaaggccgc gtagaaatga acgagaccag   15720
tgtcaccttt tttgacctcc gtcccaacga ttctgccata ctgacttact tctccgaaga   15780
tagctccggc acggagagtg aatatccgta cgccatcagc gtaagaggtg agcccttccc   15840
tacctttgtt ccattccgcc catcgagcac ctcagccgac accacacatt ttcagatccc   15900
ctccgccctc ccattctacg gctgatgact aacaattccc gtccgcggac cgagagccgc   15960
```

-continued

```
atgagcttgc agtgcatcgc gctcgataac gatagttcca ttacgtacgc ctggtacact   16020
gacaccttag agagcgggga caacatccga gaagtaaccg tccgaacgga ttctgaggta   16080
gcagttacct gtcggatatc ggatggacat tccaccaatt ccgcgactct cgtcgtgccg   16140
ctaaaccgag gtcagtaata tcccctccct caccgcaaca gatccgcaca gtcaggatcc   16200
caggctttca cgatcctttc cccactcctt tagaacctgc cgctccctac ggcgcggata   16260
tgactacggt gttcctggcc atcttagccc ttattcttct aaccgtcatc ggcggctacg   16320
ccctcagaaa gctgtgtatg cgaaacgagc gcgttttat ttgtaacccg tacagagaat   16380
gttttggcgg tcatctctag gacaaataaa cttctacttg aaatgagttt attttccccc   16440
ctgcctgttt gtgatgggaa atgatcggtg ctgcttatgg accgagatag atggaaggga   16500
cgggggcatt caaatttcta ggtccaggga cataaaaaag agatcaaatt tacatctccg   16560
gtaaagatca cctctataac cccgctgtga atcccagcac tcccttccga tacgcaaact   16620
gactagcagt tcctgtgtat agacaaacgg aatcctggtg tacagacaaa cggaatcctg   16680
agttcccaac gcattcattt atttgaatat ttacacattt acacactgta cacggtcatt   16740
cgatttcatt gccaacagaa agactaatcg atgtccccctt tcagtatgtg gactgtgaca   16800
gcagggtctt cgctcacttc actgtccgtg tcatcctctg tacgcccaca cagcatcgcc   16860
cgatagtgaa agctgacact cagcatggag aaccaaacag cagggagcaa tgtgagaggc   16920
agccaacaca gggaaacttt tttcttctcc cttcagaccc cctcccgtcg agacattgtg   16980
atggactact ggtacttcgc cctgatgttc ccaggtagga acgaccgtaa gggtgaacct   17040
ctgaacgctg ttctgcatca ggtcccgtgt cacttgatac atgccggaat ccgcgccact   17100
taagttcttg atagtcacgc agttctcgga tctgttatac gacagcctcc cttgatacgc   17160
cccgtagacc atcggctcct tcagcgcctg gtagtcctgc agcacgaact tgcgcacggc   17220
gcccgcatcc accgcggtca cttcccattc tctgatctga aaactctcgg tagaaccgca   17280
cagagtcaca gcgtcccgtt cgttagccac gacccgggat acgttctcca ttttcaccgt   17340
accgttctcg ggaagcccg acacggtgaa atatacagtc tcgggcttgg aacccaccgc   17400
gaatgattgt gatagccagc acccgttatt agctttgatt gcttcgacat gcattgaatt   17460
acaggatgaa tttagccgcg ccctcgtcat atagcccaga tccagcccct ctttgatcga   17520
aggaatcacg aaagccactt tctgccatct gttacagacc ttccccggag cgtggtacca   17580
tagcagcagc gtgaaatcag cgcatctgcc cgtagtcaga gtcacctcct tacggcccct   17640
cacggcggca ccggagacgg tggcagacaa gcagaggacg gcggcacaca gcaggagcga   17700
gccatgactg cggagtccga gccgagcggt gtgctgctcg atcctccgct acctttttat   17760
gcaccaccca cctttattgt cggtcacaca ttaattcgcc ccgtcagcaa acacgtgagt   17820
aacgtatgcc gttgttctga tcggtcagca ccgcgcccgc gacgtttgaa cgaagacgta   17880
cggtgacttc cgcataggga gctataagga agtcagttag gaaaaatcga tcctcgacac   17940
accccacgga aacgctgacc taggcgaaac ctatcaggta aaacattcac tatacgcacc   18000
acgcgttgaa taaacagtta acccatacgg ggtatatatt ctaccccgac tgcagtcagc   18060
gatcaggacg cgtccacaga gagatccgtg cgcgaccgcc tgtccgggct cctctagaat   18120
caagaattcc ataaccatgc aggtaagaac tcctttctct tcctcctatt tgatccgagc   18180 cttttttac gctactcaac cgcaaccgt ttcttccacc acagttactg ctccttctat   18240
gcctttgccc tctgatgggc agcggaacac tagcacccct cgtctcggta gacaactcct   18300
actccgtgtt cggatccggc aaaccccac tttctacctc gaatccgcc accaccgcct   18360
```

```
actccgaaac cgcggttccc gaaaactctt accccatcc gaagccacca cgccctgcga    18420
cgacttgctg gaagaggact gctggttcgc ggagagcagc gcggactacg cacccatacc    18480
ctggaacacc aaagagaata cgtccgtggt tatcccggca caggtagccg tctcgccatc    18540
gcagtccact actcccctg cggtcatgct cggcatcgca cagaaagccg taaaccgcgg     18600
agcctccagc aaggatcaca cgtcccatat cgccacgggc gttaccgtag ccggaatagt    18660
catactcatt gccctcgtca tcatagcctt ccgtacaaag gttaaggaac cgcgcccaac    18720
ccgctccatc tacctgggcg tgcctccccc tgacgttaga ccttaccgta taatagagca    18780
ataaagattt ggccgccaca tcgcacaaga atctttccgt gtcctgtgtc tgtctcggcg    18840
ccgtccgcgg gaaaaggtta acgcggaatc tatttccctg cggatttccg tatccgtcag    18900
ttcctgggcg tcgccgaaaa tgctcacgga agacacgccc atgcgggcgt ggctaaccga    18960
tgattcgaaa aacgattcgc gagcgccctc tgccggcggc ggcgggaata gggggtgtgg    19020
ggggagtgta ttttaagtag atatatatag atgatg                              19056
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:
      oligonucleotide used to amplify mature interferon coding sequence.

<400> SEQUENCE: 9
actagatctc atactgcaag tctaaat                                         27

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      oligonucleotide used to amplify coding sequence for mature
      interferon.

<400> SEQUENCE: 10
actaagcttt tagcaattgc atctcctctg                                      30